US012575827B2

(12) United States Patent
Rotem et al.

(10) Patent No.: US 12,575,827 B2
(45) Date of Patent: Mar. 17, 2026

(54) SUTURING SYSTEMS AND COMPONENTS THEREOF

(71) Applicant: NOVELRAD LTD., M.P. Hefer (IL)

(72) Inventors: Shachar Rotem, M.P. Hefer (IL);
Netanel Sharabani, Rishpon (IL); Ori Goldor, Amikam (IL)

(73) Assignee: NOVELRAD LTD., M.P. Hefer (IL)

( * ) Notice: Subject to any disclaimer, the term of this patent is extended or adjusted under 35 U.S.C. 154(b) by 415 days.

(21) Appl. No.: 17/773,849

(22) PCT Filed: Dec. 7, 2020

(86) PCT No.: PCT/IB2020/061610
§ 371 (c)(1),
(2) Date: May 3, 2022

(87) PCT Pub. No.: WO2021/111429
PCT Pub. Date: Jun. 10, 2021

(65) Prior Publication Data
US 2022/0354485 A1     Nov. 10, 2022

Related U.S. Application Data

(60) Provisional application No. 62/943,861, filed on Dec. 5, 2019.

(51) Int. Cl.
*A61B 17/06*     (2006.01)
*A61B 17/04*     (2006.01)
*A61B 17/00*     (2006.01)

(52) U.S. Cl.
CPC ...... *A61B 17/0491* (2013.01); *A61B 17/0469* (2013.01); *A61B 2017/00367* (2013.01); *A61B 2017/0609* (2013.01)

(58) Field of Classification Search
CPC .. A61B 17/0491; A61B 17/0469–0483; A61B 2017/047–048; A61B 2017/00367; A61B 2090/0807–0812
See application file for complete search history.

(56) References Cited

U.S. PATENT DOCUMENTS 4,440,171 A     4/1984  Nomoto et al.
5,389,103 A  *  2/1995  Melzer ............... A61B 17/0469
                                                 606/147

(Continued)

FOREIGN PATENT DOCUMENTS

CN         114206230 A      3/2022
EP           2083702 B1     8/2009
(Continued)

OTHER PUBLICATIONS

Japanese Office Action for JP2022500474 Mailed on Apr. 3, 2024.
Japanese Office Action for JP2022-522842 Mailed on May 28, 2024.

*Primary Examiner* — Brooke Labranche
*Assistant Examiner* — Jonathan A Hollm
(74) *Attorney, Agent, or Firm* — The Roy Gross Law Firm, LLC; Roy D. Gross

(57)                    ABSTRACT
A drive mechanism for operating a suturing mechanism includes a user input displaceable through a range of motion and a linkage mechanically associated with the user input and with a shuttle transmitter of the suturing mechanism. The linkage converts displacements of the user input unidirectionally or bidirectionally into a sequence of operations of the shuttle transmitter including sufficient to perform a sequence of operations of the suturing mechanism to perform successive bidirectional stitching, with the shuttle transmitter penetrating tissue alternately with and without a shuttle needle attached.

20 Claims, 41 Drawing Sheets

(56)                    References Cited

U.S. PATENT DOCUMENTS

| | | | | |
|---|---|---|---|---|
| 5,478,351 | A * | 12/1995 | Meade | A61B 17/2909 |
| | | | | 606/174 |
| 5,613,974 | A | 3/1997 | Andreas et al. | |
| 5,814,054 | A | 9/1998 | Kortenbach et al. | |
| 6,051,006 | A | 4/2000 | Shluzas et al. | |
| 6,077,276 | A | 6/2000 | Kontos | |
| 6,136,010 | A | 10/2000 | Modesitt et al. | |
| 6,245,079 | B1 | 6/2001 | Nobles et al. | |
| 6,355,050 | B1 | 3/2002 | Andreas et al. | |
| 6,746,457 | B2 | 6/2004 | Dana et al. | |
| 6,964,668 | B2 | 11/2005 | Modesitt et al. | |
| 7,094,246 | B2 | 8/2006 | Anderson et al. | |
| 7,211,093 | B2 | 5/2007 | Sauer et al. | |
| 7,354,443 | B2 | 4/2008 | Moll et al. | |
| 7,449,024 | B2 | 11/2008 | Stafford | |
| 7,618,425 | B2 | 11/2009 | Yamamoto et al. | |
| 8,137,364 | B2 | 3/2012 | Zung et al. | |
| 8,287,556 | B2 | 10/2012 | Gilkey et al. | |
| 8,313,498 | B2 | 11/2012 | Pantages et al. | |
| 8,454,631 | B2 | 6/2013 | Viola et al. | |
| 8,628,545 | B2 | 1/2014 | Cabrera et al. | |
| 8,641,728 | B2 * | 2/2014 | Stokes | A61B 17/00234 |
| | | | | 606/139 |
| 8,709,020 | B2 | 4/2014 | Nobles | |
| 8,821,518 | B2 | 9/2014 | Saliman et al. | |
| 8,870,917 | B2 | 10/2014 | Walters | |
| 9,265,488 | B2 | 2/2016 | Galligan et al. | |
| 9,398,907 | B2 | 7/2016 | Nobles et al. | |
| 9,775,603 | B2 | 10/2017 | Kasahara et al. | |
| 10,076,323 | B2 * | 9/2018 | Smith | A61B 17/0469 |
| 10,182,804 | B2 | 1/2019 | Walters et al. | |
| 2003/0025023 | A1 * | 2/2003 | Rosenfeld | A61B 17/06123 |
| | | | | 242/395 |
| 2005/0154403 | A1 | 7/2005 | Sauer et al. | |
| 2007/0276413 | A1 | 11/2007 | Nobles | |
| 2009/0005793 | A1 | 1/2009 | Pantages et al. | |
| 2009/0105752 | A1 | 4/2009 | Shonteff et al. | |
| 2010/0130990 | A1 * | 5/2010 | Saliman | A61B 17/0469 |
| | | | | 606/145 |
| 2010/0152751 | A1 | 6/2010 | Meade | |
| 2011/0022063 | A1 | 1/2011 | McClurg et al. | |
| 2011/0028998 | A1 | 2/2011 | Adams | |
| 2012/0116366 | A1 * | 5/2012 | Houser | H01M 10/425 |
| | | | | 606/1 |
| 2012/0277768 | A1 * | 11/2012 | Viola | A61B 17/0469 |
| | | | | 606/145 |
| 2013/0245646 | A1 | 9/2013 | Lane et al. | |
| 2014/0249552 | A1 * | 9/2014 | Tang | A61B 17/0057 |
| | | | | 606/145 |
| 2015/0230790 | A1 | 8/2015 | Hashimoto | |
| 2016/0066916 | A1 * | 3/2016 | Overmyer | G06F 1/3287 |
| | | | | 227/176.1 |
| 2018/0235604 | A1 | 8/2018 | Comee et al. | |
| 2019/0142402 | A1 | 5/2019 | Larzon et al. | |
| 2019/0282226 | A1 | 9/2019 | Epstein et al. | |

FOREIGN PATENT DOCUMENTS

| | | |
|---|---|---|
| EP | 2230987 B1 | 2/2013 |
| JP | 2001-524864 A | 12/2001 |
| JP | 2003305046 A | 10/2003 |
| JP | 2013525083 A | 6/2016 |
| WO | 2018156603 A1 | 8/2018 |
| WO | 2020057513 A1 | 3/2020 |
| WO | 2021111429 A1 | 6/2021 |

* cited by examiner

Through type shuttle needle and needle transmitter module with striping member

Male type shuttle needle and needle transmitter module with ejector member

Female type shuttle needle and needle transmitter module with striping member

Striping member 204

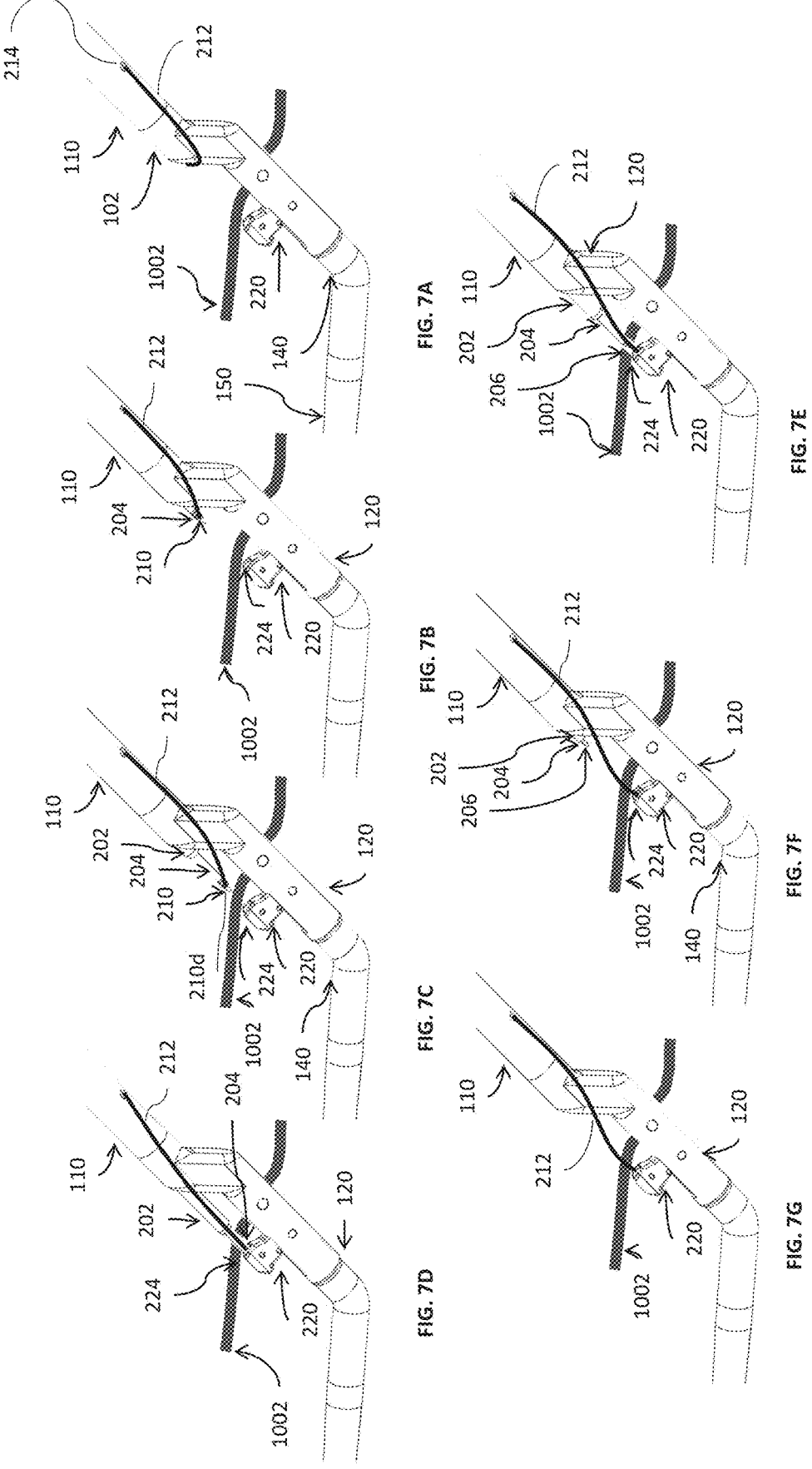

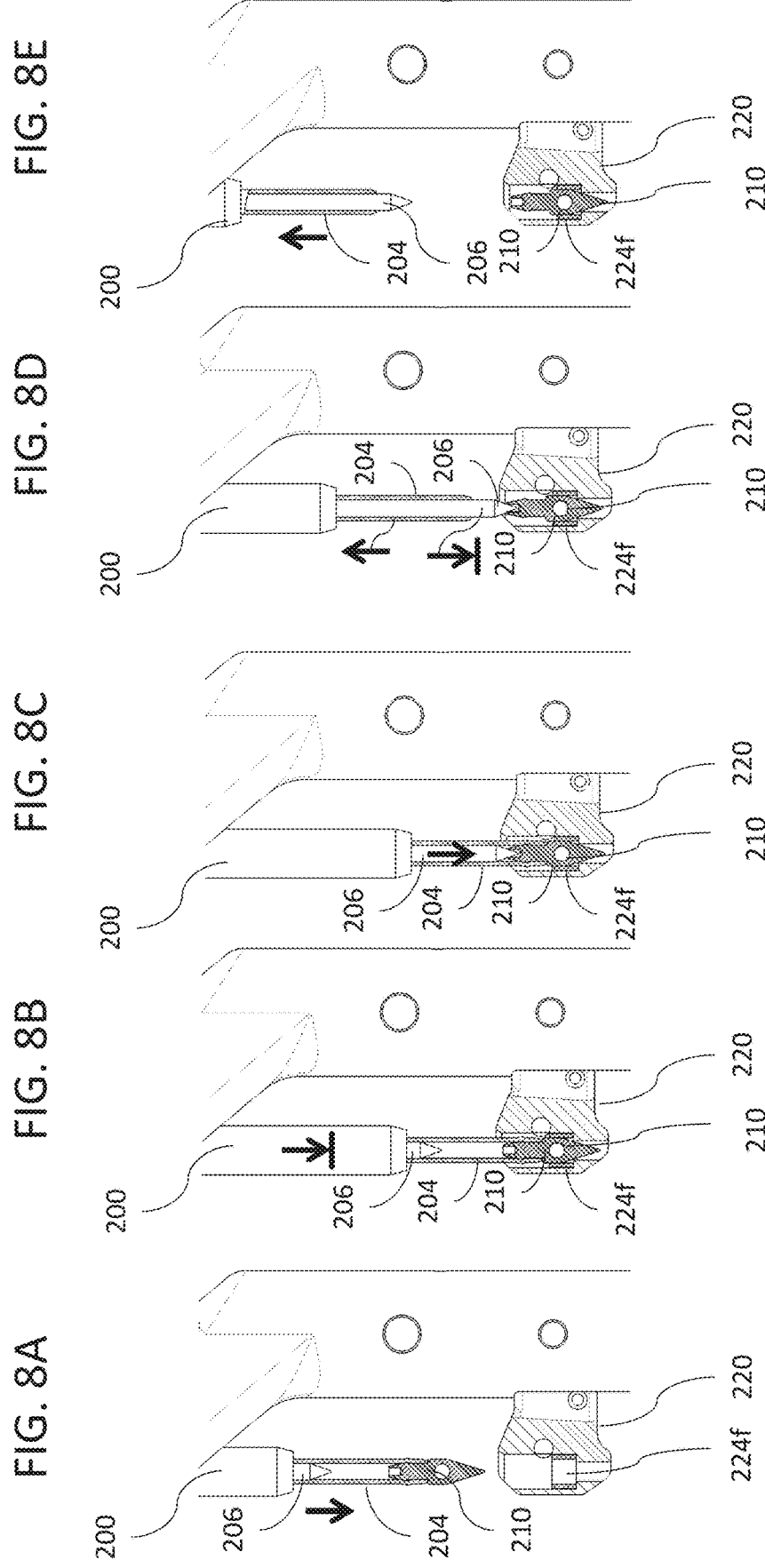

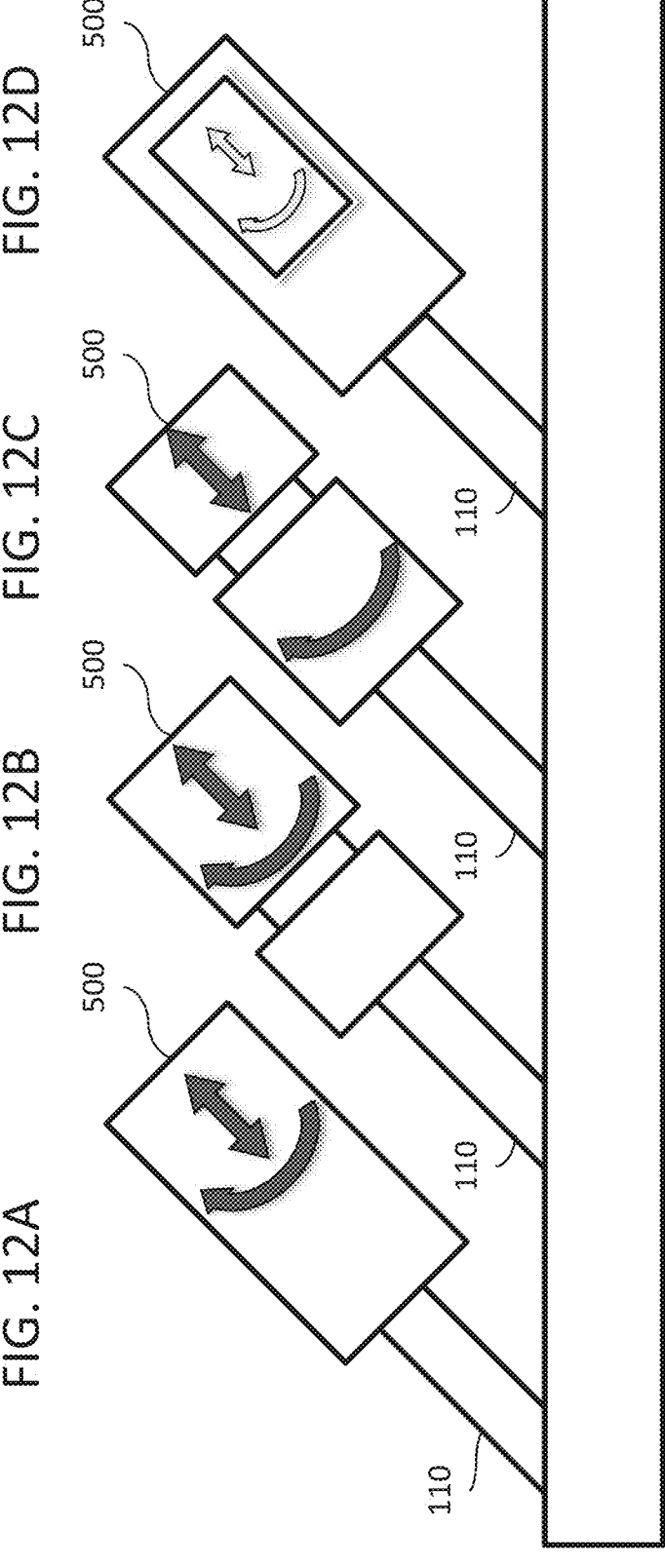

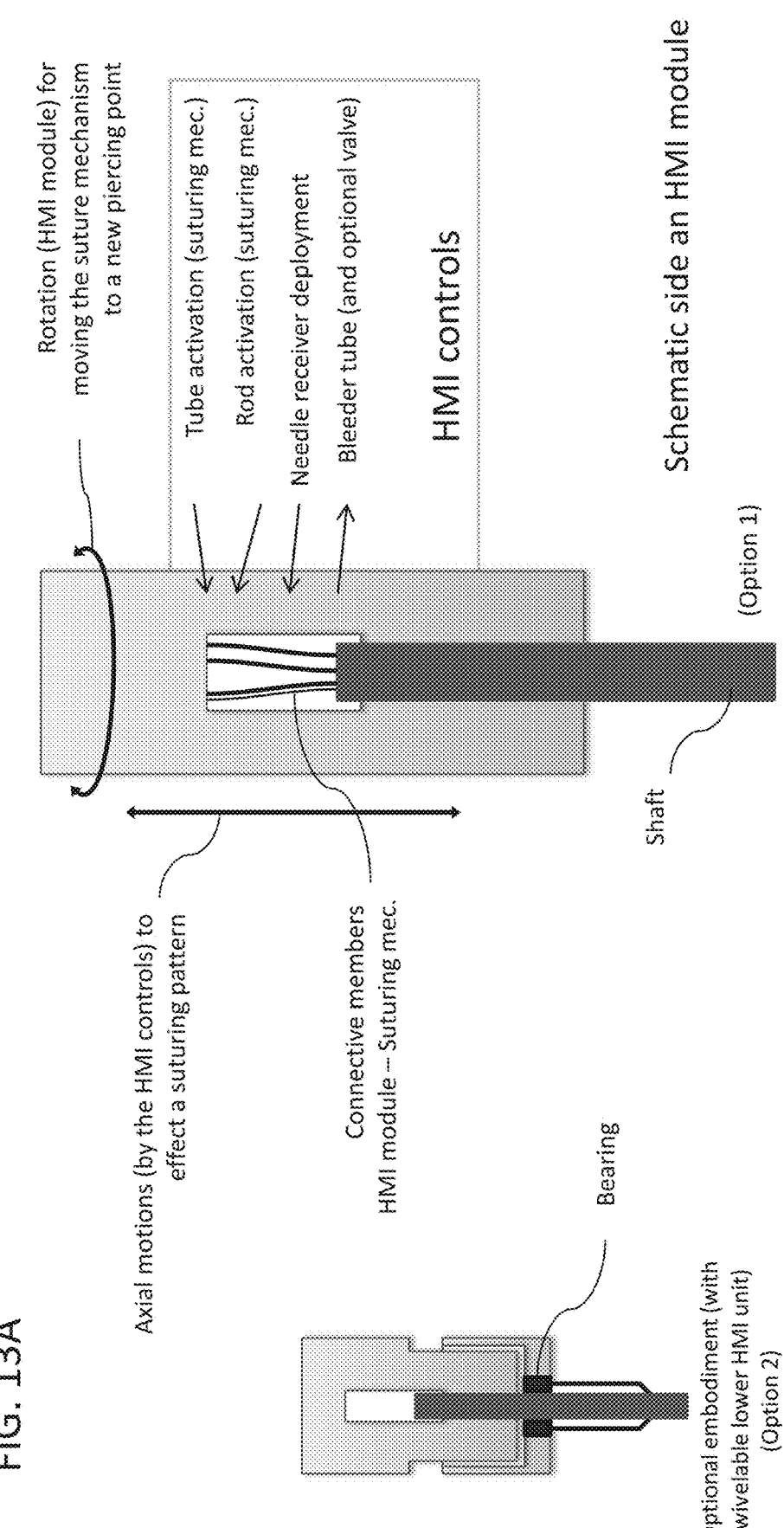

Rotation (HMI module) for moving the suture mechanism to a new piercing point

Tube activation (suturing mec.)
Rod activation (suturing mec.)
Needle receiver deployment
Bleeder tube (and optional valve)

HMI controls

Schematic side an HMI module (Option 1)

Shaft

Axial motions (by the HMI controls) to effect a suturing pattern

Connective members HMI module — Suturing mec.

Bearing

Optional embodiment (with swivelable lower HMI unit) (Option 2)

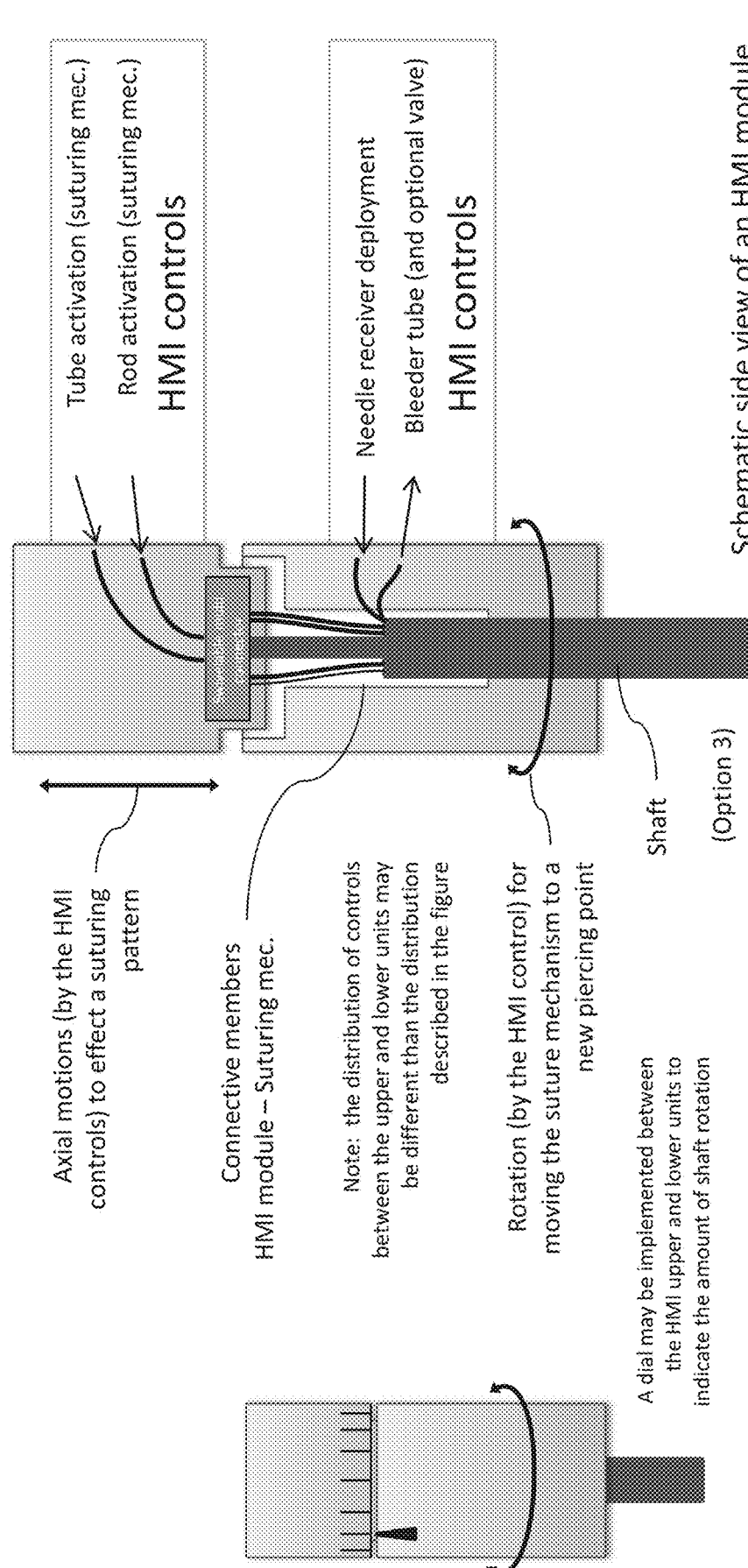

Tube activation (suturing mec.)

Rod activation (suturing mec.)

HMI controls

Needle receiver deployment

Bleeder tube (and optional valve)

HMI controls

Schematic side view of an HMI module

Axial motions (by the HMI controls) to effect a suturing pattern

Connective members

HMI module – Suturing mec.

Note: the distribution of controls between the upper and lower units may be different than the distribution described in the figure Rotation (by the HMI control) for moving the suture mechanism to a new piercing point Shaft (Option 3)

A dial may be implemented between the HMI upper and lower units to indicate the amount of shaft rotation

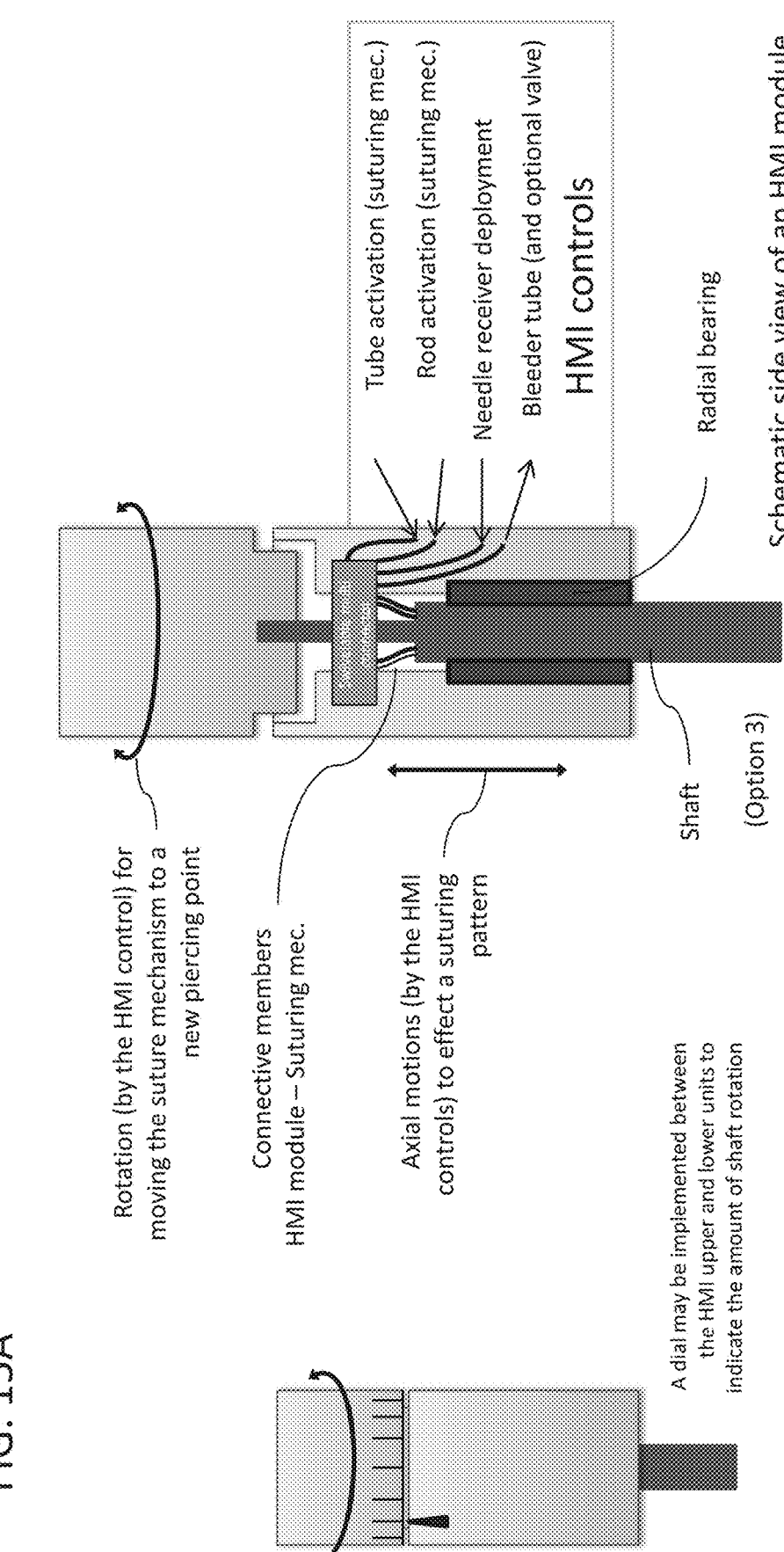

Tube activation (suturing mec.)

Rod activation (suturing mec.)

Needle receiver deployment

Bleeder tube (and optional valve)

HMI controls

Radial bearing

Schematic side view of an HMI module

Rotation (by the HMI control) for moving the suture mechanism to a new piercing point Connective members HMI module – Suturing mec.

Axial motions (by the HMI controls) to effect a suturing pattern

Shaft (Option 3)

A dial may be implemented between the HMI upper and lower units to indicate the amount of shaft rotation

Figures 16A, 16B:
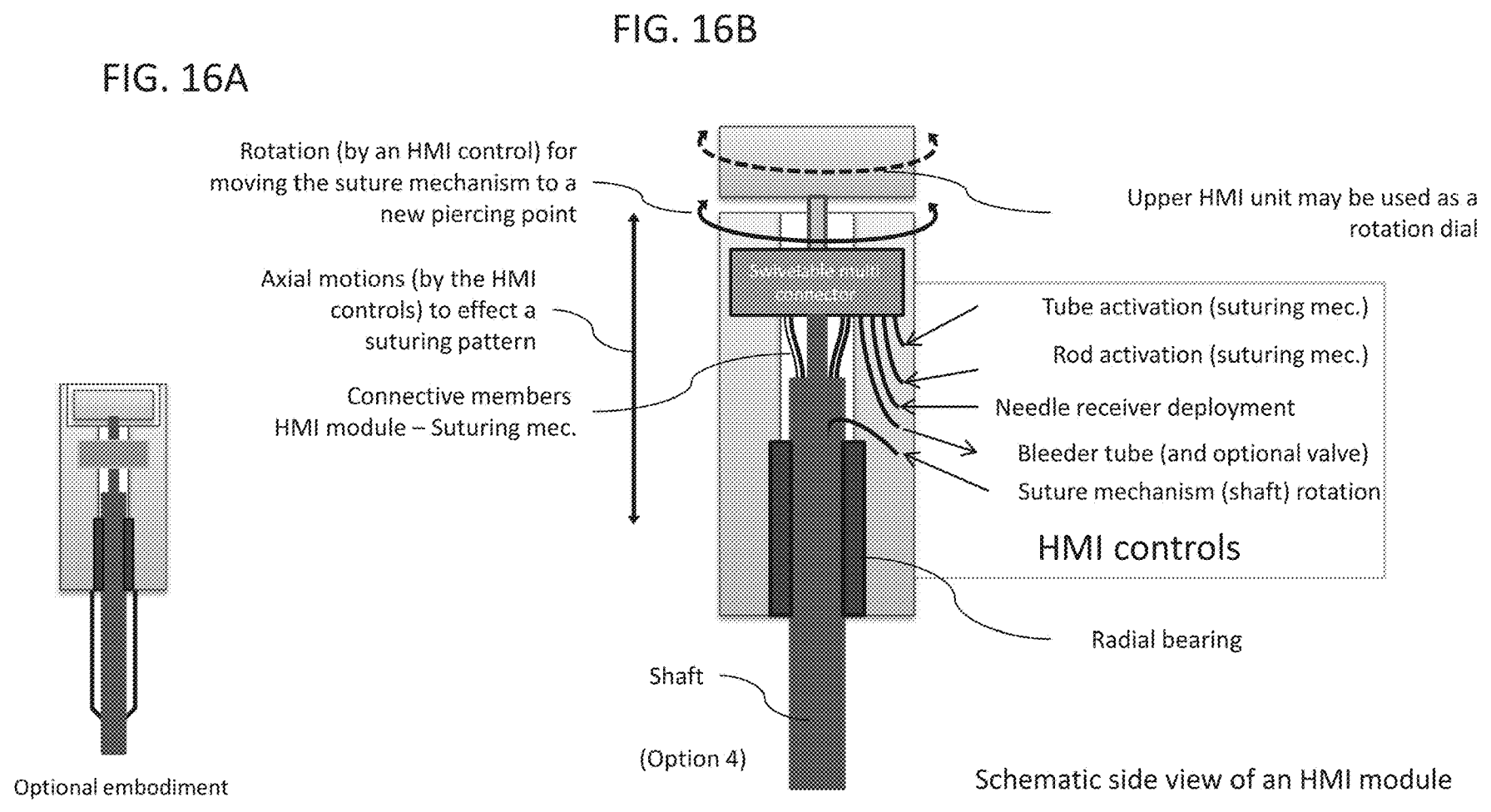

Rotation (by an HMI control) for moving the suture mechanism to a new piercing point Axial motions (by the HMI controls) to effect a suturing pattern Connective members HMI module – Suturing mec.

Upper HMI unit may be used as a rotation dial

Tube activation (suturing mec.)

Rod activation (suturing mec.)

Needle receiver deployment

Bleeder tube (and optional valve)

Suture mechanism (shaft) rotation

HMI controls

Radial bearing

Shaft (Option 4)

Schematic side view of an HMI module

Optional embodiment

749

747

731

750
751
748
746
752

735

745

749
746
748
736

206

734

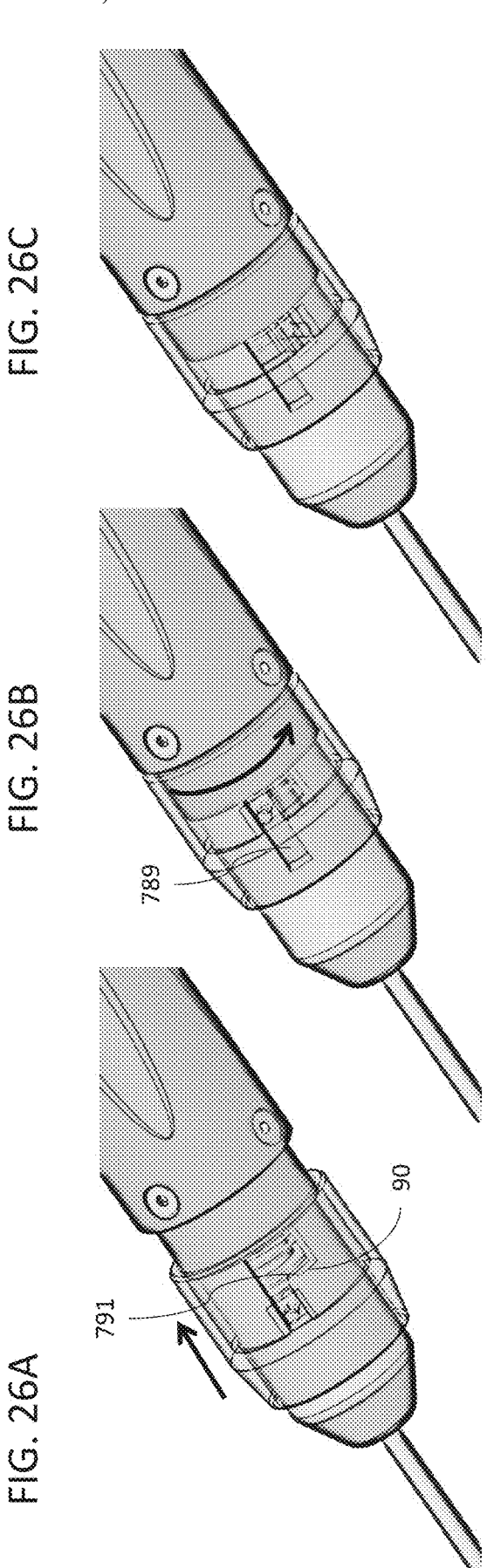

Dial hand poisoned on first piercing point before the local suturing cycle ended Dial hand poisoned on first piercing point after local suturing cycle has ended Dial hand poisoned on second piercing point before the local suturing cycle ended Dial hand poisoned on sixth (last) piercing point after local suturing cycle (and full suturing pattern) has ended Helical disk

822

820

823 click, click

825

820

821

824

Cross section view of a bobbin with teeth on its side wall circumference

SUTURING SYSTEMS AND COMPONENTS THEREOF

FIELD AND BACKGROUND OF THE INVENTION

The present invention relates to suturing systems and, in particular, suturing systems for suturing applications, such as closing incisions, joining tissues, or regions of tissue, and/or modifying the shape of tissue.

Suturing is a common surgical technique for closing incisions, joining tissues, or regions of tissue, and/or modifying the shape of tissue. Suturing in the context of a minimally-invasive procedure or otherwise in small and confined surgical spaces presents particular challenges, requiring a high skill level of the surgeon. In the specific context of vascular closure devices, certain dedicated tools are currently available to facilitate suturing. However, these devices have various limitations, and are typically unable to provide continuous bidirectional stitching to-and-fro through a thickness of tissue.

SUMMARY OF THE INVENTION

The present invention relates to a suturing system, and components thereof.

According to the teachings of an embodiment of the present invention there is provided, a drive mechanism for operating a suturing mechanism, the suturing mechanism having a shuttle for holding a suture, motion of the shuttle being controlled by a shuttle transmitter that is displaceable along a longitudinal axis between a withdrawn position and a penetrating position, the shuttle transmitter being reconfigurable between a shuttle holding state and a shuttle releasing state, the drive mechanism comprising: (a) a user input displaceable through a range of motion; and (b) a linkage mechanically associated with the user input and with the shuttle transmitter, the linkage configured to convert displacements of the user input unidirectionally or bidirectionally into a sequence of operations of the shuttle transmitter including: (i) axial displacement of the shuttle transmitter from the withdrawn position to the penetrating position so as to penetrate the material at a first location; (ii) reconfiguration of the shuttle transmitter from the shuttle holding state to the shuttle releasing state; and (iii) axial displacement of the shuttle transmitter from the penetrating position to the withdrawn position so as to withdraw from the material leaving a first suture stitch at the first location; and, after repositioning of the shuttle transmitter and the shuttle aligned at a second location: (iv) axial displacement of the shuttle transmitter from the withdrawn position to the penetrating position so as to penetrate the material at the second location; (v) reconfiguration of the shuttle transmitter from the shuttle releasing state to the shuttle holding state so as to hold the shuttle; and (vi) axial displacement of the shuttle transmitter from the penetrating position to the withdrawn position so as to withdraw the shuttle from the material forming a second suture stitch at the second location.

According to a further feature of an embodiment of the present invention, the reconfiguration of the shuttle transmitter from the shuttle holding state to the shuttle releasing state generates a tissue penetrating configuration of the shuttle transmitter without the shuttle, and wherein the reconfiguration of the shuttle transmitter from the shuttle releasing state to the shuttle holding state generates a tissue penetrating configuration of the shuttle transmitter together with the shuttle.

According to a further feature of an embodiment of the present invention, the repositioning of the shuttle transmitter is also performed by the linkage driven by displacements of the user input unidirectionally or bidirectionally.

According to a further feature of an embodiment of the present invention, the linkage is configured to convert further displacements of the user input unidirectionally or bidirectionally into repetition of the sequence of operations of the shuttle transmitter when aligned with a third and a fourth location so as to form a running stitch suture in the material.

According to a further feature of an embodiment of the present invention, the user input is manually displaceable in a first direction, and is spring-biased to return in a reverse direction when released.

According to a further feature of an embodiment of the present invention, the shuttle transmitter comprises a shuttle holder and a shuttle ejector, and wherein reconfiguration of the shuttle transmitter between the shuttle holding state and the shuttle releasing state is effected by axial motion of the shuttle ejector relative to the shuttle holder.

According to a further feature of an embodiment of the present invention, the linkage includes a first transmission defining a first timing profile for motion of the shuttle holder as a function of displacement of the user input and a second transmission defining a second timing profile for motion of the shuttle ejector as a function of displacement of the user input.

According to a further feature of an embodiment of the present invention, the second timing profile defines motion of the shuttle ejector as a function of displacement of the user input over two cycles of displacement of the shuttle transmitter from the withdrawn position to the penetrating position and back to the withdrawn position, wherein the motion over a first of the two cycles is non-identical to the motion over a second of the two cycles.

According to a further feature of an embodiment of the present invention, the shuttle ejector and the shuttle holder are mounted on a common slide, and wherein the linkage includes a first transmission defining a first timing profile for motion of the slide as a function of displacement of the user input and a second transmission defining a second timing profile for motion of the shuttle ejector and/or the shuttle holder as a function of displacement of the slide.

According to a further feature of an embodiment of the present invention, the second timing profile defines motion of the shuttle ejector and/or the shuttle holder as a function of displacement of the user input over two cycles of displacement of the shuttle transmitter from the withdrawn position to the penetrating position and back to the withdrawn position, wherein the motion over a first of the two cycles is non-identical to the motion over a second of the two cycles.

According to a further feature of an embodiment of the present invention, the suturing device is a minimally-invasive suturing device including an elongated body for percutaneous insertion, and wherein the user input and the linkage are implemented as part of a handle associated with a proximal end of the elongated body.

According to a further feature of an embodiment of the present invention, the suturing device further comprises a shuttle receiver for receiving the shuttle on the second side of the material, the shuttle receiver being retractable to a retracted position relative to the elongated body and selectively deployable to a deployed position for receiving the shuttle, the drive mechanism further comprising a manually-operated actuator linked to the shuttle receiver for deploying the shuttle receiver from the retracted position to the deployed position, the actuator being associated with the handle at a location distal to the user input.

According to a further feature of an embodiment of the present invention, the elongated body is rotatable about its longitudinal axis relative to the handle for performing stitches in successive angular positions about the elongated body, and wherein the handle further comprises a mechanical indicator linked to the elongated body and configured to provide a visual indication of a current rotational position of the elongated body relative to the handle.

According to a further feature of an embodiment of the present invention, the mechanical indicator is additionally associated with the linkage and configured to provide a visual indication when the passing of the suture through the material has been completed at the current rotational position.

According to a further feature of an embodiment of the present invention, there is also provided a suture feeder associated with the handle for feeding suture along the elongated body to the shuttle, wherein the suture feeder is configured to provide tactile and/or audible feedback to a user as the suture is dispensed.

According to a further feature of an embodiment of the present invention, the elongated body is rotatable about its longitudinal axis relative to the handle for performing stitches in successive angular positions about the elongated body, further comprising a bleeder tube extending from a bleeder inlet along the elongated body to an outlet associated with the handle, wherein the bleeder tube includes an unsupported loop of tube located to accommodate relative rotation between the elongated body and the handle.

According to a further feature of an embodiment of the present invention, there is also provided a pinch valve associated with the handle and deployed to selectively obstruct the bleeder tube.

According to a further feature of an embodiment of the present invention, there is also provided: (a) a shuttle receiver for receiving the shuttle on the second side of the material; (b) a depresser associated with the shuttle transmitter, the depresser at least partially encompassing the shuttle transmitter and deployable to press the material between the depresser and the shuttle receiver; and (c) at least one sensor associated with the depresser and generating an output indicative of a thickness of the material between the depresser and the shuttle receiver.

According to a further feature of an embodiment of the present invention, the user input includes a first part of a magnetic snap and wherein the handle includes a second part of the magnetic snap, the first and second parts of the magnetic snap being deployed such that, when the user input reaches a fully-displaced position, the first and second parts of the magnetic snap close together abruptly to generate tactile and/or audible feedback.

According to a further feature of an embodiment of the present invention, the user input is resiliently biased to return from the fully-displaced position to an initial position, and wherein the magnetic snap has a retention force which is insufficient to retain the user input in the fully-displaced position against the resilient bias.

According to a further feature of an embodiment of the present invention, the magnetic snap has a retention force sufficient to retain the user input in the fully-displaced position until positively displaced by the user back towards the initial position.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIGS. 7A-7G are diagrams of an operational sequence for shuttle (needle) insertion;

FIGS. 8A-8E are a sequence of schematic partial axial-cross-sectional views taken through the suturing mechanism showing the motion of components of the shuttle transmitter during a suture stitch sequence;

FIGS. 12A-12D are schematic representations of options for full or partial swivel connection between a device shaft and the HMI module;

FIGS. 13A, 13B, 14A, 14B, 15A, 15B, 16A and 16B are schematic axial cross-sectional views illustrating in more detail implementation options corresponding to FIGS. 12A-12D;

FIGS. 26A-26C are side views illustrating three positions of the actuator of FIG. 25;

FIGS. 32A and 32B are partial isometric views illustrating two possible deployments of a bleed tube relative to a shaft of the suturing device;

DESCRIPTION OF THE PREFERRED EMBODIMENTS

Figure 1A:
FIG. 1A is a schematic perspective view of a suturing system in accordance with an embodiment of the disclosed subject matter for vascular closure applications.

Before explaining at least one embodiment of the disclosed subject matter in detail, it is to be understood that the disclosed subject matter is not necessarily limited in its application to the details of construction and the arrangement of the components and/or methods set forth in the following description and/or illustrated in the drawings. The disclosed subject matter is capable of other embodiments or of being practiced or carried out in various ways.

Throughout this document, references to directions, such as proximal, distal, inward, outward, inner, outer, upper, lower, up, down, top, bottom, right, left, forward, backward, and the like, are made. These directional references, including their derivatives, are to typical orientations for the apparatus 100, shown in the drawing figures (FIGS.) and/or components thereof. They are exemplary only, and not limiting in any way, as they are for description and explanation purposes.

By way of introduction, aspects of the present invention relate to a system for suturing, particularly a system which includes a suturing mechanism as described in co-pending PCT patent application no. PCT/M2020/057513, which was unpublished on the effective filing date of this application, and which does not constitute prior art. The present invention relates to various aspects of a human-machine interface (HMI) particularly suited, although not necessarily limited, to use with a suturing mechanism such as that described in the aforementioned application, and variants thereof. In order to facilitate an understanding of certain aspects of the present invention, a brief description of the suturing mechanism itself is given here with reference to FIGS. 1A-10C, Further details of the suturing mechanism, and variant implementations thereof, may be found in the aforementioned application.

Before referring to the drawings, certain aspects of the present invention relate to a device and method for suturing a material or materials, for example, in vivo biological tissue as part of a surgical procedure. In general terms, the device and method employ a shuttle, typically in the form of a pointed shuttle needle, to hold a suture, and a shuttle transmitter to selectively hold and release the shuttle. The shuttle transmitter, when holding the shuttle, forms a first penetrating configuration, and after releasing the shuttle, presents a second penetrating configuration. At this second penetrating configuration the shuttle transmitter is typically configured to present a pointed, needle like, end.

The shuttle transmitter manipulates the shuttle from one side of the material, referred to arbitrarily as the proximal side, to perform passes of the suture from the proximal side to the distal side and from the distal side to the proximal side, thereby facilitating a wide range of running stitch patterns. Specifically, a pass from the proximal side to the distal side is performed by advancing the shuttle transmitter in the first penetrating configuration, i.e., while the shuttle is gripped, so that at least the shuttle penetrates the material at a first location, and then releasing the shuttle from the shuttle transmitter, preferably to be held temporarily by a shuttle receiver, and withdrawing the shuttle transmitter from the material without the shuttle. A pass of the suture from the distal side to the proximal side is performed by advancing the shuttle transmitter in the second penetrating configuration, i.e., without the shuttle, for collecting and retrieving the shuttle through the sutured material. The shuttle transmitter penetrates the material at a second location aligned with the shuttle that is temporarily retained in the shuttle receiver, engages and holds the shuttle, and withdraws the shuttle through the material at the second location. During each pass, the shuttle draws with it the suture such that the suture extends into the material at the first location and out of the material at the second location.

The shuttle needle transmitter thus serves as a "Push-Pull Mechanism" (PPM) for the corresponding shuttle needle to perform the following operations:

1. Push the needle through a sutured media.
2. Eject the Needle at the other side of the media or inside the media and retreat without it.
3. Be reconfigured to provide a penetrating end.
4. Re-penetrate the media to reengage/collect the needle and pull/retreat with the needle.

This process of passing the shuttle in alternating directions through the material can be repeated at a series of locations, and allows formation of a wide range of running-stitch suture configurations for a wide range of different applications.

In order to facilitate collection of the shuttle by the shuttle transmitter for a distal-to-proximal pass, both the shuttle and the shuttle transmitter are preferably displaced so as to be aligned with the material at the second location. The shuttle may advantageously be held, and displaced, while released from the shuttle transmitter, by a shuttle receiver which is configured to receive and retain the shuttle. Alignment of the shuttle transmitter and the shuttle receiver on opposite sides of the material to be sutured may be maintained by a bridging portion, which forms a mechanical interconnection between the shuttle transmitter and the shuttle receiver. Various non-limiting examples of each of these structures will be described in detail below.

Aspects of the present invention find a wide range of applications in both non-medical and medical fields. Within the medical field, aspects of the present invention are applicable to a wide range of procedures, whether external/superficial, shallow incisions, minimally invasive procedures, and conventional surgically procedures. By way of one non-limiting set of exemplary preferred implementations, the present invention will be illustrated herein primarily in the context of a vascular closure device. It will be appreciated that this example is only one of a large number of suitable applications for the technology, as will be clear to a person ordinarily skilled in the art. Brief reference will be made below to a number of other non-limiting examples of additional applications.

Turning now to the non-limiting example of FIG. 1A, this shows a suturing system 100 in accordance with an embodiment of the disclosed subject matter particularly adapted for vascular closure applications. The suturing apparatus 100 includes a suturing module 102, formed of an optional shaft 110, with proximal 110p and distal 110d ends, and a bridging portion 120 extending laterally from the distal end 110d of the shaft 110. The bridging portion 120 includes proximal 120p and distal 120d ends, and connects to the shaft 110 at the proximal end 120p. A handle 130 is at the proximal end 110p of the shaft 110, and is used to manipulate the components of the suturing module 102. A flexible connector 140 extends from the distal end 120d of the bridging portion 120, and an optional dilator 150 extends distally from the flexible connector 140. The bridging portion 120 is, for example, connected to the flexible connector 140, so as to be rotatable relative to the flexible connector 140.

Figure 1B:
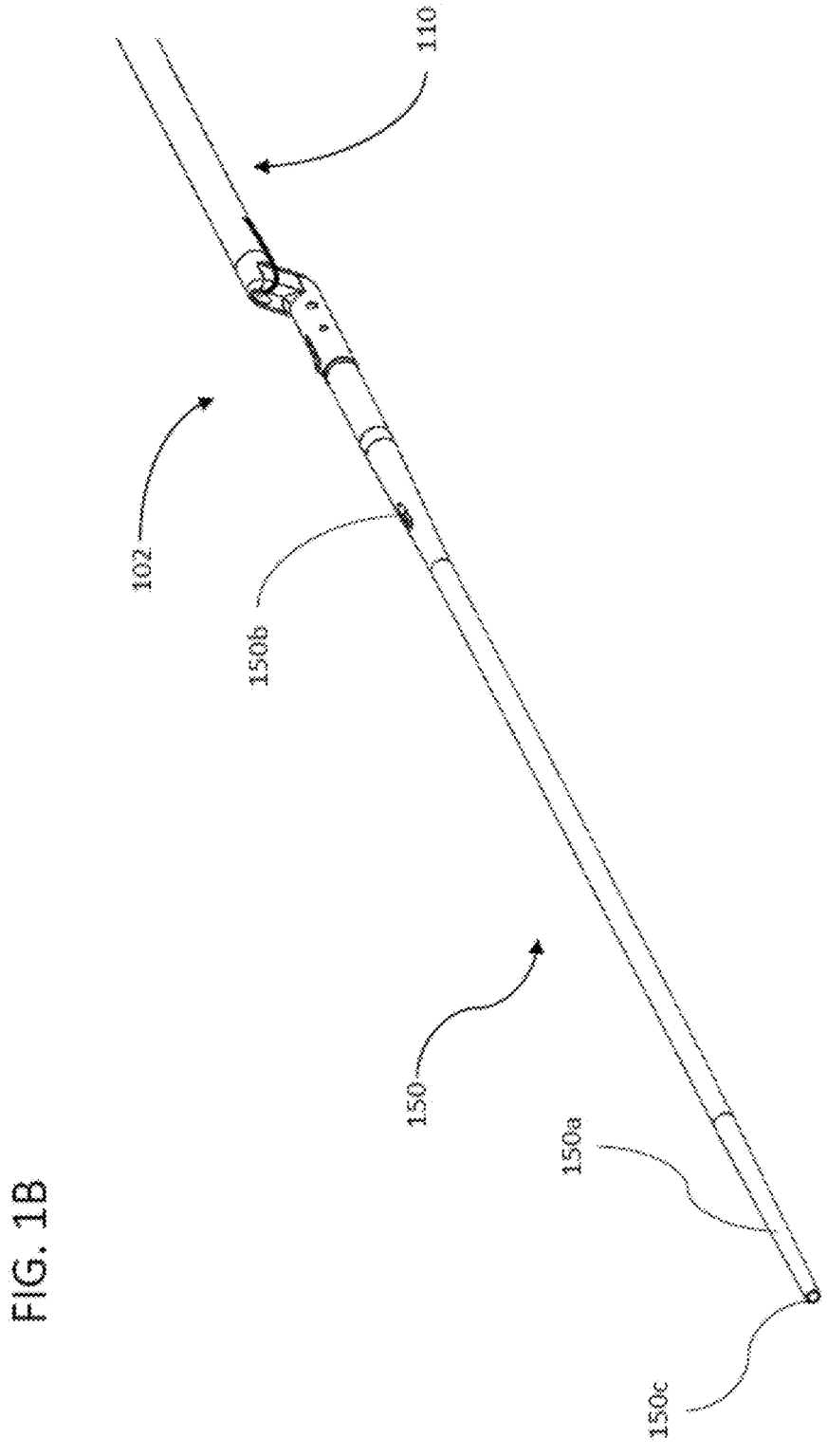
FIG. 1B is an enlarged perspective view of a distal portion of the suturing apparatus of FIG. 1A.

FIG. 1B is an enlarged view of the distal part of suturing apparatus 100, showing the suturing module 102 and an exemplary implementation of the dilator 150 employed for expanding a blood vessel during preparation for the suturing procedure and/or for another procedure to be performed via the vascular access point. The dilator 150 has a distal conical portion 150a which facilitates expansion of the blood vessel as inserted. An internal channel extends from a lateral entrance point 150b to an aperture at a hollow tip 150c of the dilator. This internal channel serves for over-the-wire insertion of the device, in a manner known in the art.

Figure 2A:
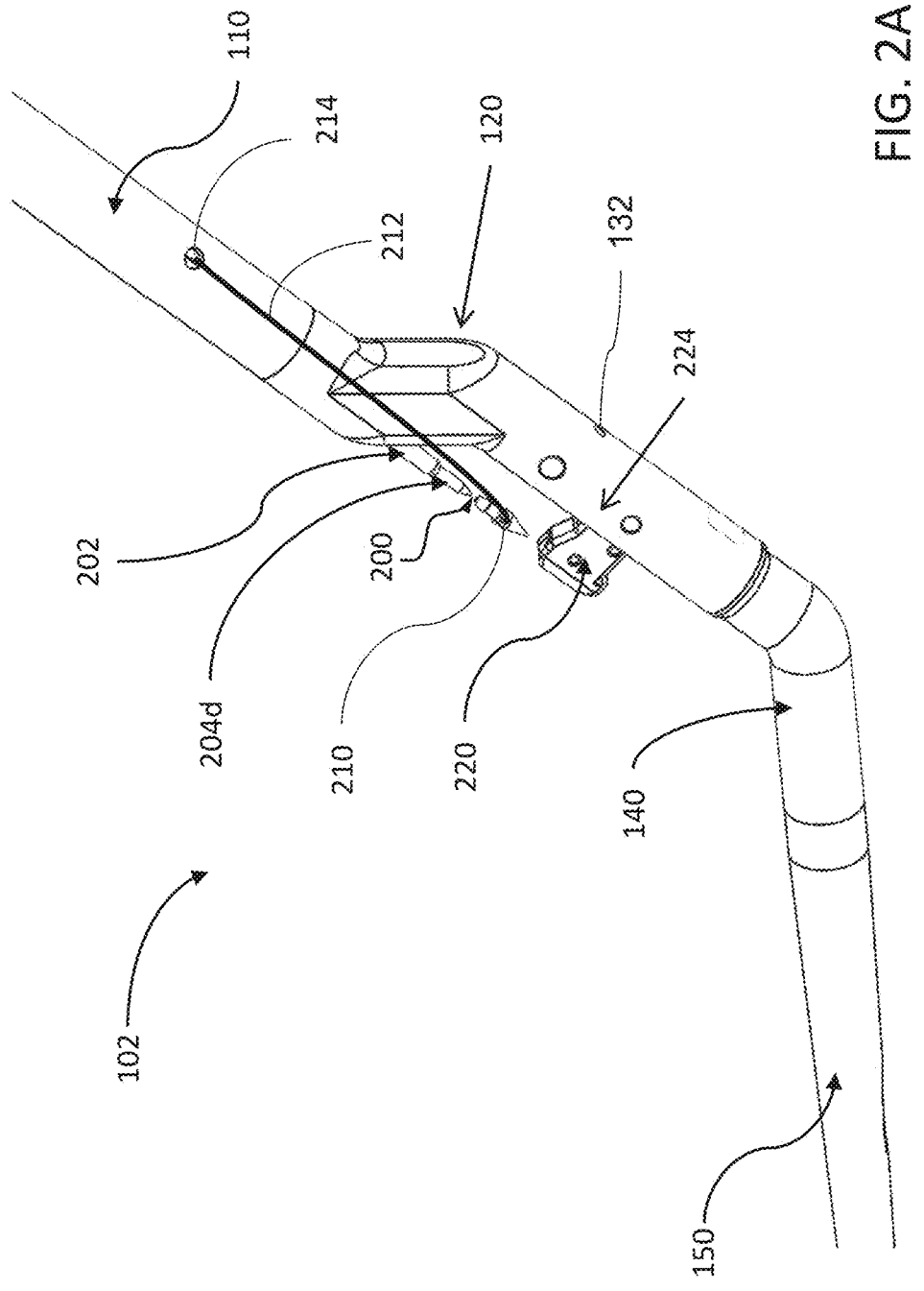
FIGS. 2A and 2B are perspective views of the suturing module of the suturing apparatus of FIG. 1A.
Figure 2B:
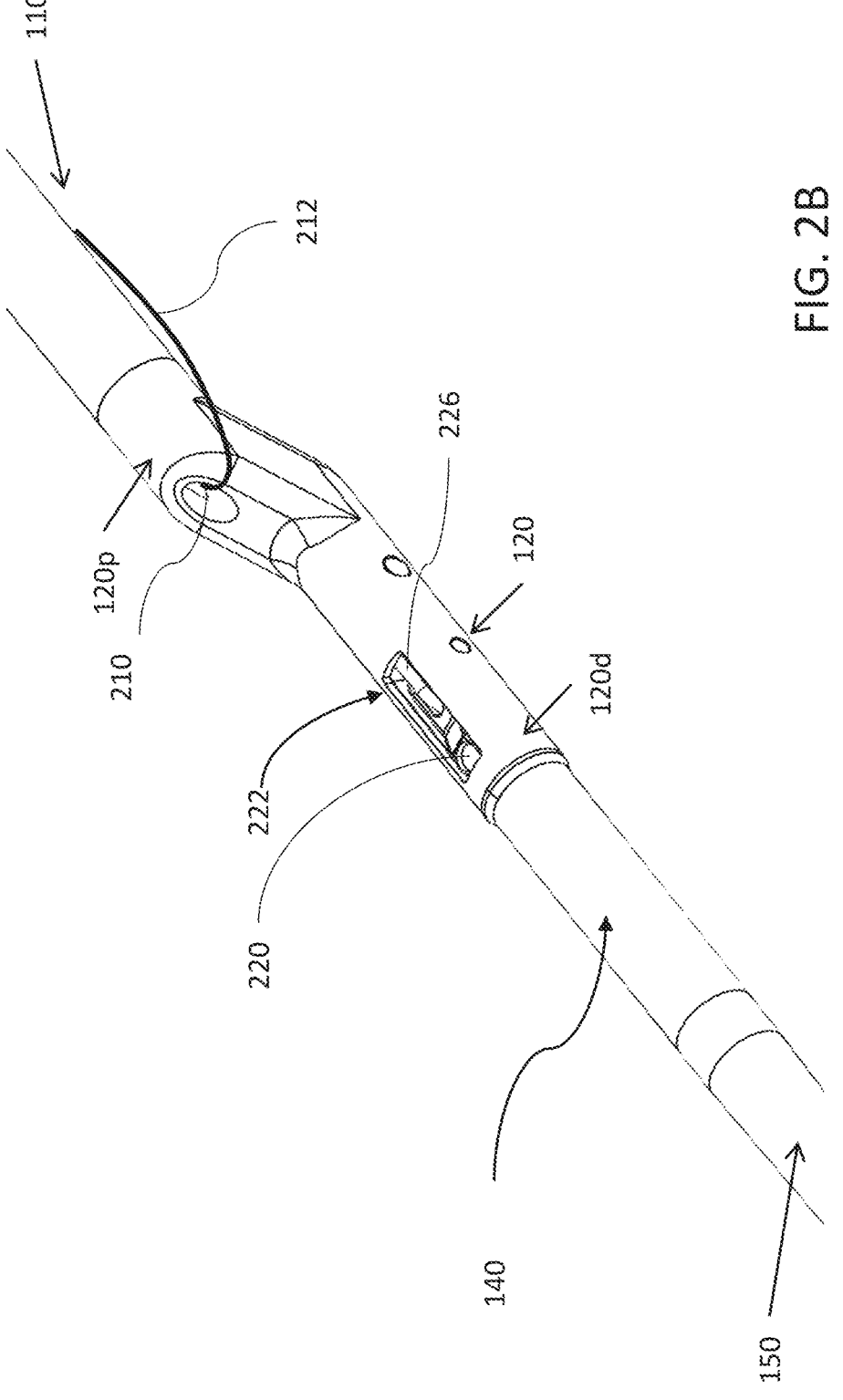
Figure 2C:
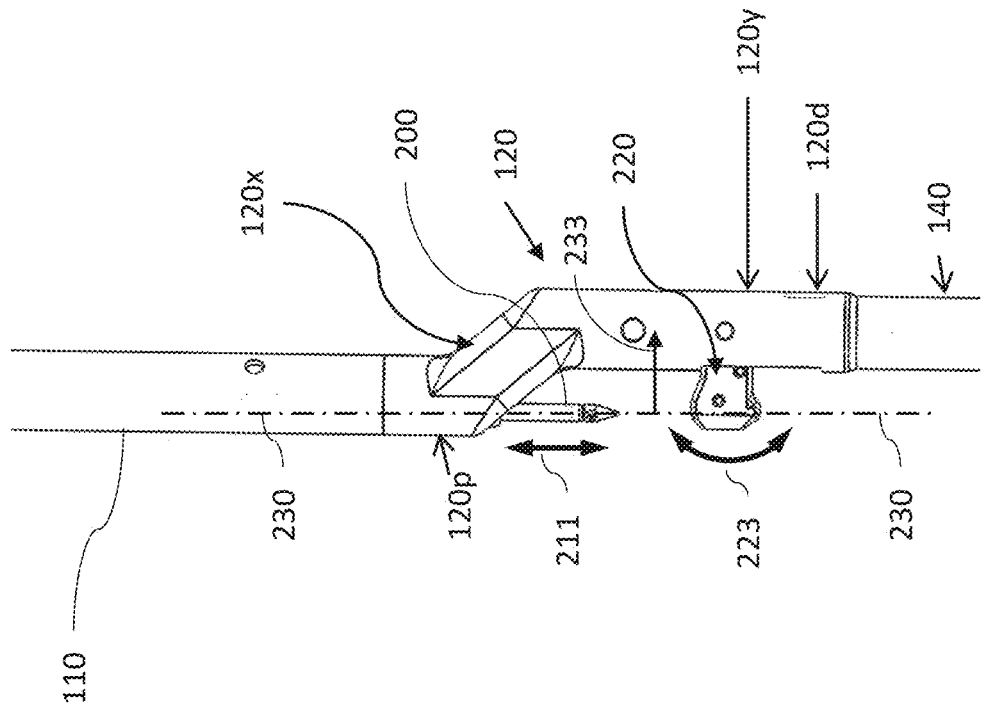
FIG. 2C is a side view of the suturing module of the suturing apparatus of FIG. 1A.

FIGS. 2A-2C, to which attention is also directed, show the suturing module 102 of the suturing apparatus 100 (FIG. 1A). The suturing module or suturing mechanism 102 (these terms used interchangeably herein) includes a shuttle transmitter 200, a shuttle, typically implemented as a shuttle needle 210 (optionally engaged with a suture 212 or suture filament), and a shuttle (needle) receiver 220. The suturing module 102 may be designed and configured to suture media much thicker than the length of the needle 210, as will become clear from the structure and function of the module as detailed below. The shaft 110 supports a shuttle or needle transmitter 200, which is movable proximally and distally within the shaft 110, with this movement controllable by the handle 130, as detailed herein below. The shuttle or needle transmitter 200 may be configured to push and pull the needle 210 through a sutured media (e.g., tissue).

The shuttle 210 is primarily exemplified herein in an implementation where the shuttle has a penetrating point and functions as a needle. Shuttle 210 is thus referred to interchangeably as a "shuttle needle 210", and in some cases simply "needle 210". Likewise, "shuttle transmitter 200" and "shuttle receiver 220" may alternatively be referred to as needle transmitter 200 and needle receiver 220, respectively. It should be noted however that the invention may also be implemented employing a shuttle without a penetrating point, for example as will be discussed below with reference to FIG. 9C, and that all features described herein are equally applicable to such embodiments unless explicitly stated otherwise.

Functionally, needle transmitter 200 includes a shuttle holder for holding the shuttle 210 and a shuttle releaser displaceable relative to the shuttle holder for releasing the shuttle 210 from the shuttle holder. In the non-limiting example illustrated here, as will be further described below with reference to FIG. 3C, the shuttle holder is implemented as a tubular element (e.g., a tube 204) which engages an external engagement surface of shuttle 210, while the releaser is implemented as a rod 206, displaceable internally within the tubular element. The term "tubular element" is used herein to refer to any hollow element which has a generally tube-like appearance, including but not limited to regular tubes of circular, polygonal or other cross-sectional shape, such tubes with a shaped internal contour for positive engagement and tubes with cut away slots or other features to increase flexibility or provide an engagement configuration. It should be noted that these implementations of the shuttle holder and the shuttle releaser are considered advantageous as being particularly simple and compact, but that substantially any holder arrangement for holding the shuttle 210, externally, internally or via any other suitable mechanical engagement, whether by friction, by mechanical engagement or any other form or retention, may be used. In each case, a corresponding releaser is provided. The releaser may be implemented either as an element which interacts with the holder to neutralize (release) a holding or gripping effect, or may interact directly with the shuttle to eject the shuttle through overcoming retention forces applied by the holder, or some combination of the above.

In the implementation illustrated here, the shuttle transmitter 200 includes a tube 204, and a rod 206, for example, arranged coaxially and, for example, axially displaceably, with respect to each other. The tube 204 is moveable proximally and distally in the shaft 110, with movement controlled, for example, by the handle 130, as detailed below. The rod 206 is moveable proximally and distally within and out of the tube 204, with the movement controlled, for example, by the handle 130, as detailed below.

The rod 206, in this example, includes a pointed tip 206a at its distal end 206d for piercing tissue in various applications detailed herein. The rod 206 also functions as an ejector (or "releaser") for a shuttle 210. The rod 206 ejects the needle 210 from the transmitter 200, for example, after the needle 210 has been transferred through the sutured media. Ejecting of needle 210 is implemented, for example, after the needle 210 is securely located inside (the pocket 224) of the needle receiver 220. The rod 206 may hold the needle 210 inside the receiver 220 while the needle transmitter 200 is disengaging, optionally retracting through the sutured media, preventing release of needle 210 from the needle receiver 220 during this process. Rod 206 may thus release shuttle needle 210 while it is stationary, due to the relative motion of rod 206 and tube 204. The rod 206 in this example has a sharp suture needle-like shape 206a, as its distal end. Before the needle transmitter 200 is activated, to pass through a sutured media, without the needle 210, for example, to engage the needle 210, located in the needle receiver 220, the ejector 206 is advanced relative to the distal end of tube 204 to provide the aforementioned second penetrating configuration. Additional applications for the rod 206 are detailed below.

At least a penetrating length 229 (FIG. 3B) of needle transmitter 200, typically including the rod (ejector member) 206 and tube 204, possibly with additional elements, typically have a cross-section not larger than the shuttle needle 210. The cross section may in certain applications have a dimension corresponding to a range of USP #4-0 or similar.

The distal end 204d of the tube 204, coupled with the pointed tip 206a of the rod 206, form a holder or engaging mechanism for a shuttle 210, shown being held or engaged by the tube 204. Additionally, the distal end 204d of the tube 204, coupled with the pointed tip 206a of the rod 206, form a releaser or ejector for the shuttle 210 (into a pocket 224 of a shuttle receiver 220), as part of a shuttle 210 ejection and insertion operation, as shown in FIGS. 7A-7G, as well as a mechanism for gripping and engaging the shuttle 210, to remove the shuttle 210 from the pocket 224, as part of a shuttle 210 reconnection and retraction operation, as shown in FIGS. 8A-8G.

Figure 4C:
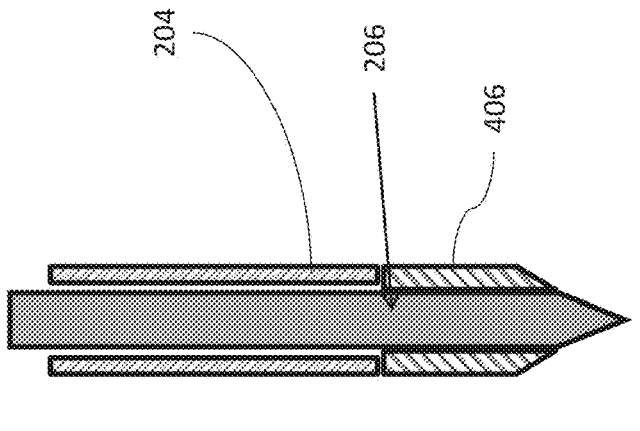
FIGS. 4A, 4B and 4C are diagrams of shuttles, including shuttle needles, for the suturing apparatus of FIG. 1A.

The shuttle 210 is, for example, a shuttle needle, as shown for example in FIGS. 4A and 4B, and detailed below, or a shuttle without its own penetrating point, as shown in FIG. 4C. The shuttle 210 receives and holds a suture 212, for example, extending from an opening (suture release aperture) 214 in the shaft 110, where it is fed along an internal lumen or otherwise stored in a suture feed volume. The opening 214 is, for example, located on the shaft 110 at the opposite side of the suturing line of action (230 FIG. 2C). As an alternative geometrical definition of this feature, the shuttle transmitter 200 and the shuttle receiver 220 are preferably aligned along a first axis 230, corresponding to the "suturing line of action". At least part of the bridging portion is offset from this first axis in a first direction 233. The suture release aperture 214 is preferably oriented to face away from the first axis and preferably opens towards the first direction. In other words, in intuitive terms, the suture release aperture is located on the "rear" of the device relative to the current suturing line of action, and is optimized for feeding the suture in a direction that is generally away from the current suturing line of action.

The shuttle transmitter 200, including the outer tube 202, tube 204, and rod 206, with the shuttle 210 attached, is preferably fully retractable into the shaft 110, as shown, for example, in FIG. 2B, as well as extendable from the shaft 110, as shown by the double headed arrow 211 of FIG. 2C. For medical applications, both the tube 204 and the rod 206 are typically made of surgical grade metals, including super elastic and shape memory alloys and materials such as Nitinol, although other metal and non-metallic materials may also be used.

The bridging portion 120 supports a receiver 220, also known as a shuttle receiver, these terms used interchangeably herein, which is, for example, pivotally mounted in a slot 222 of the bridging portion 120, to be retractable into (FIG. 2B) and out of the (FIGS. 2A and 2C) slot 222, as shown by the double headed curved arrow 223 of FIG. 2C. The receiver 220 includes a pocket 224, for receiving the shuttle 210, for example, in a frictional or snap-lock engagement. The frictional engagement is such that the shuttle 210 can be placed into the pocket 224 and held therein, as well as removed from the pocket 222 by the shuttle transmitter 200. The deployment of the receiver 220 is controlled by an actuator 226, which is, for example, a wire which behaves in a spring-like manner, preferably pre-shaped to return to a deflected form when advanced so as to bias the receiver 220 towards a retracted position, inside the slot 222 of the bridging portion 120, and operative to move the receiver 220 to an extended position, projecting outside of the slot 222 of the bridging portion 120 when actuator 226 is pulled. The actuator 226 is, for example, controlled by manipulating the handle 130, as detailed below. The actuator 226 may be made of surgical grade metals, including super elastic and shape memory alloys and materials such as Nitinol.

The bridging portion 120 also preferably includes an opening or port 227a for a bleeder tube 228. The bleeder tube extends to the shaft 110, and a port 227b, through which blood can be detected. Based on blood being detected, the user can determine that the bridging portion is inside the tissue, for example, the vessel, at the proper surgical site (location).

Also, as shown in FIG. 2C, the bridging portion 120 includes a deflected portion 120x at the proximal end 120p, that generates a lateral offset from the axis of suturing motion 230 in direction 233 for the continuation of bridging portion 120, implemented here as a linear portion 120y. This construction results in a linear line of suturing with a predefined offset between the suture line of action 230 and the center line of the rotation member.

Figures 3A, 3B:
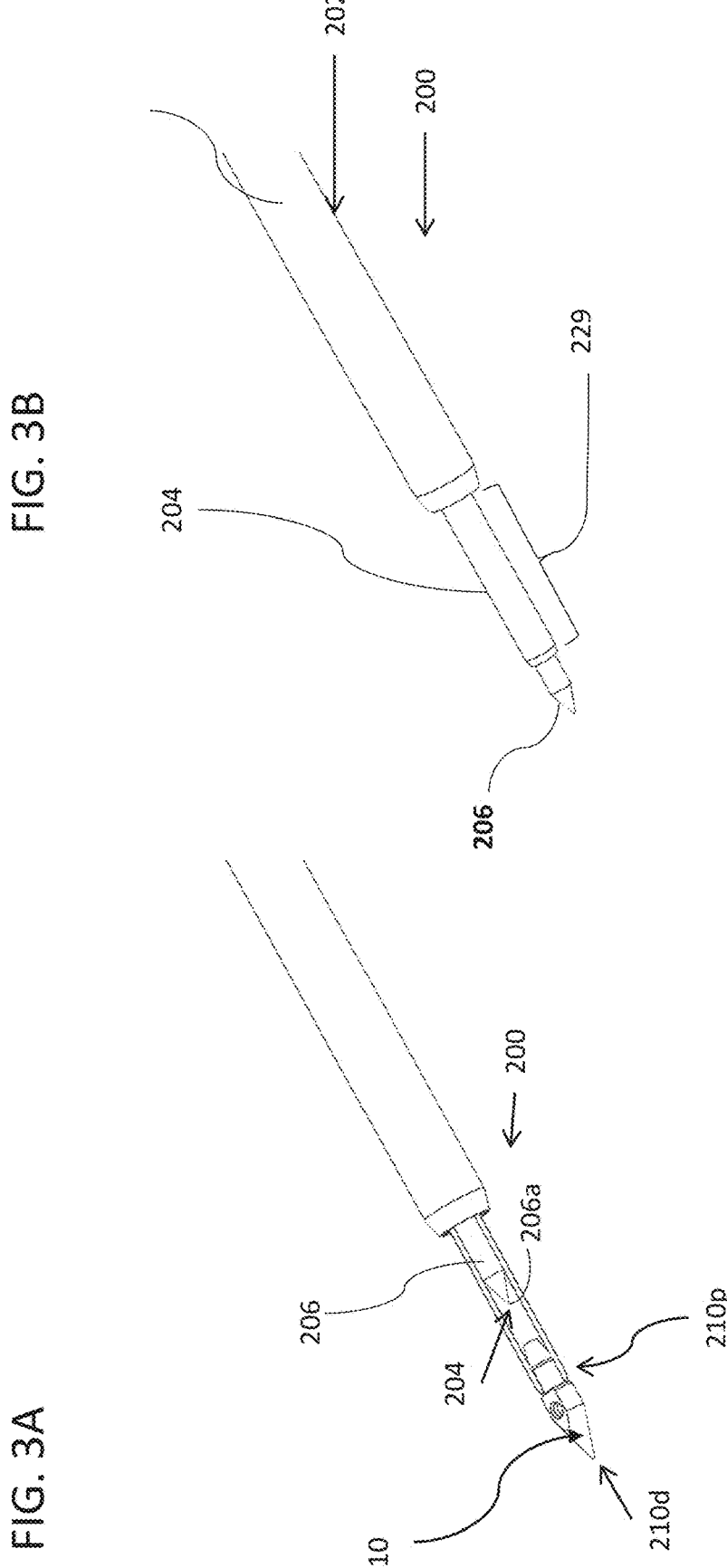
FIGS. 3A, 3B, and 3C are side views of a needle transmitter module of the apparatus of FIG. 1A.
Figure 3C:
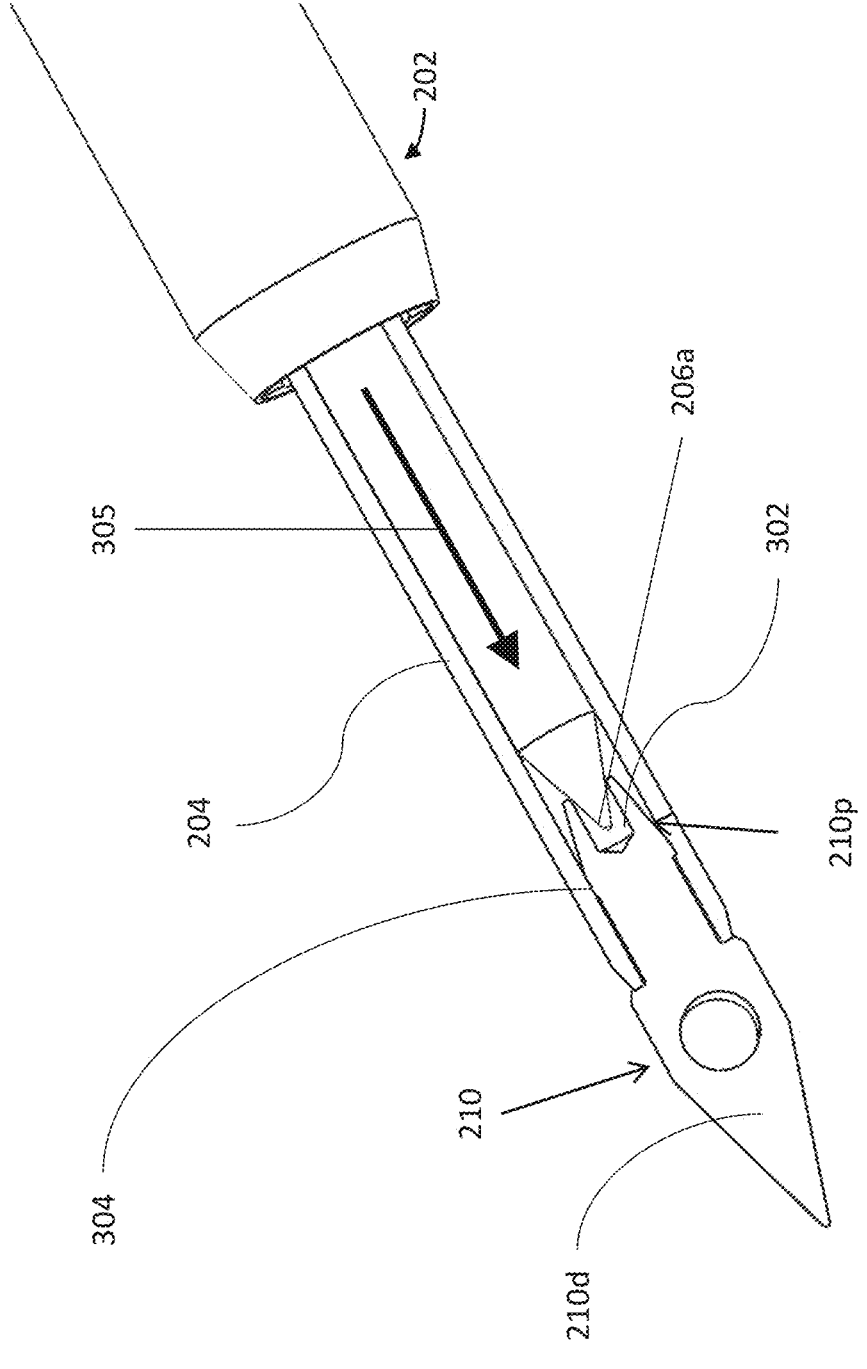

Attention is also directed to FIGS. 3A-3C, which show an embodiment of the shuttle transmitter 200. As shown in FIG. 3A, the outer tube 202 supports the tube 204. The tube 204 is, for example, made of a super elastic alloy, such as Nitinol, and grips the shuttle 210, to engage the shuttle 210, for example, a shuttle needle. The rod 206 is moved distally into contact with the shuttle needle 210, such that its distal pointed tip 206a seats in a recess 302 of the shuttle needle 210, as shown in FIG. 3C. Further distal motion from this position results in the rod 206 functioning as an ejector or releaser, for releasing the shuttle needle 210.

FIG. 3B shows the tube 204, for example, extending from the outer tube 202 to a length typically longer than the sutured media thickness, thereby defining a penetrating length of shuttle transmitter 200 as represented by the square bracket 229. It will be noted that it is primarily this penetrating length which defines the thickness of material (e.g., tissue) which can be sutured using suturing module 102. Accordingly, this penetrating length 229 is typically chosen to be longer than a length of shuttle needle 210, and in certain preferred cases at least twice as long, more preferably at least three times longer, and in many cases, more than 5 times, the length of the shuttle needle. Certain implementations of the present invention are thus able to effect bidirectional suturing through a material having a thickness greater than the length of shuttle needle 210.

The elongated portion of tube 204, designated by numeral 229, together with the overall suture mechanism construction having a parallel line of action relative to the bridge portion described in FIG. 2C provides flexible, axial, position of the suturing device relative to the sutured media. This allows suturing of an access hole in a blood vessel or any suture material thinner than 229, even if the material is thicker than the length of the shuttle needle which is passed back-and-forth (hence the term "shuttle").

FIG. 3C shows a shuttle needle 210 being gripped or engaged by the shuttle transmitter 200, prior to being ejected into a shuttle receiver 220. In this embodiment, the shuttle needle 210 includes an oversize diameter portion 304 at its proximal end 210p, the oversized diameter portion 304 being of a larger diameter than the diameter of the tube 204. With the tube 204 preferably being made of Nitinol, the distal movement (as indicated by the arrow 305) of the rod 206, with its tip 206a, seated in the recess 302 of the shuttle needle 210, pushes the shuttle needle 210 distally, such that the oversize diameter portion 304 of the shuttle needle 210, pushes the tube 204 outward, deforming the tube 204, creating engagement forces that allow the pull of the shuttle needle 210 during suturing.

Figure 4B:
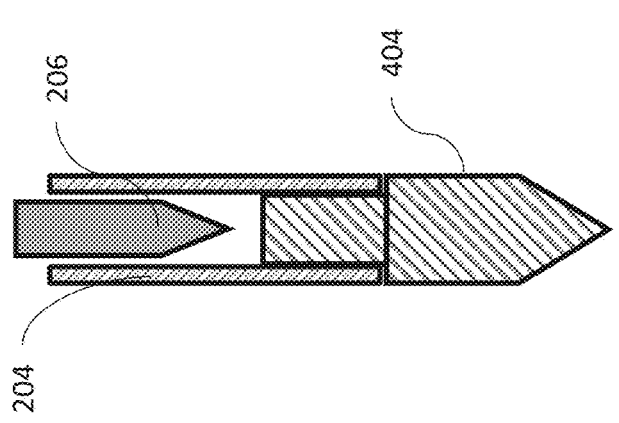
Figure 4A:
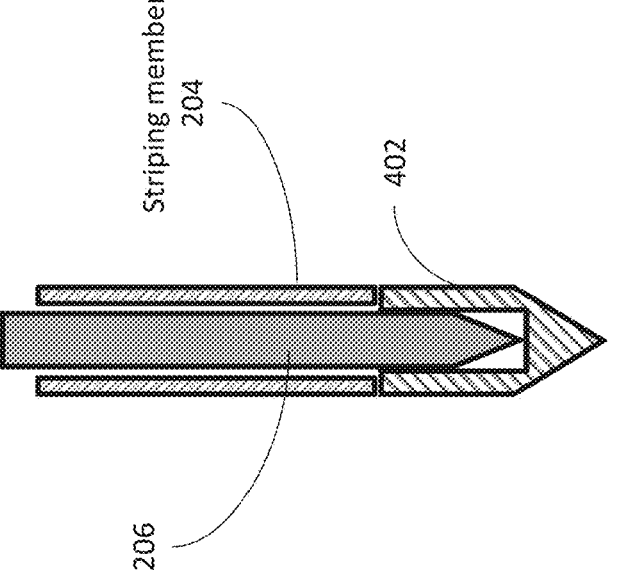

FIGS. 4A-4C show general examples of shuttles 210 (for example, as shown in FIG. 2A). FIGS. 4A and 4B show shuttles in the form of needles (shuttle needles) 402, 404, while FIG. 4C shows a shuttle 406. For example, in FIG. 4A, the shuttle needle 402 is a female-type, as it is frictionally engaged by the rod 206, the rod movable within the tube 204. For example, in FIG. 4B, the shuttle needle 404 is a male-type, as it is frictionally engaged by tube 204, and pushed distally by the rod 206, when disengagement is of the shuttle needle 404 is desired.

In each case of a shuttle needle with a piercing tip, it should be noted that the piercing tip may have any form suitable for piercing the corresponding material to be sutured, and is not limited to a conical tip. Alternative forms include various forms with bevels and/or sharpened ridges, with three-fold, four-fold or other symmetry, or with asymmetric tips.

In FIG. 4C the shuttle 406 includes an open central core 408, through which the piercing tip 206a of the rod 206 extends through, in order to function as the piercing tip for the shuttle 406. The rod 206 is of a diameter at least equal to and typically greater than the diameter of the core 408, to frictionally engage the shuttle 406. When release of the shuttle 406 from engagement with the rod 206 is desired, the tube 204 is moved distally, pushing the shuttle 406 off of the rod 206, or, the rod 206 is moved proximally, such that the contact between the shuttle 406 and the tube 204, allows the shuttle 406 to be freed from the engagement of the rod, or combinations of both of the aforementioned movements.

In each of the options of FIGS. 4A-4C, the needle transmitter may be configured to present a needle like pointed end without the presence of the shuttle or shuttle needle.

In many cases, the suture 212 emerges laterally from a medial region of the shuttle, particularly when it is desired to provide a distal penetrating tip and a proximal portion to be gripped by the shuttle holder.

Figures 5A, 5B:
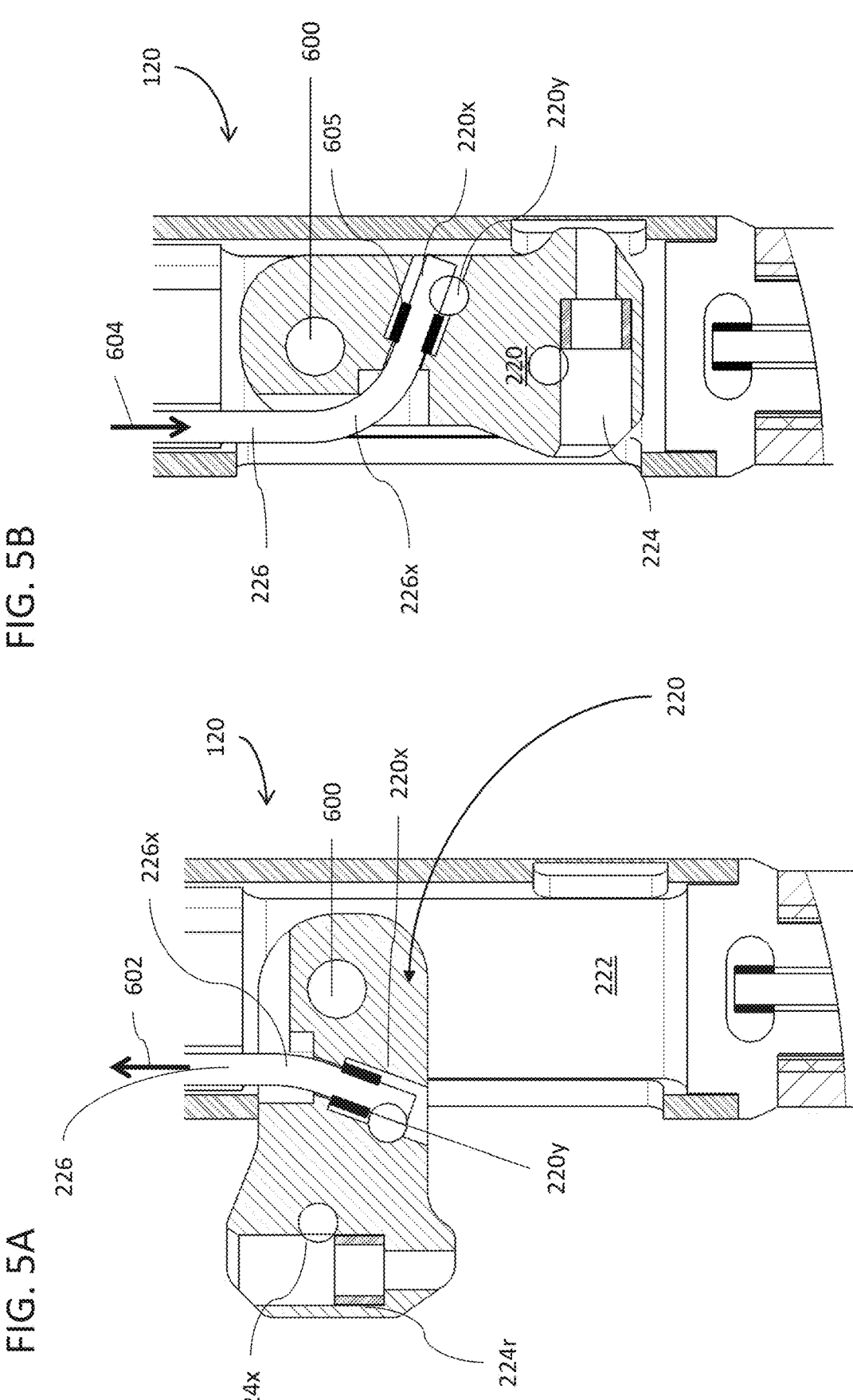
FIGS. 5A, and 5B are cross sectional views of a shuttle receiver and actuation mechanism for the suturing apparatus of FIG. 1A.

FIGS. 5A and 5B show an exemplary implementation of the receiver (shuttle receiver) 220 in detail. The receiver 220 is attached to the bridging portion 120 by a pin 600 or other structure which defines a hinge axis, or otherwise guides the deployment and retraction motion of receiver 220, which allows for rotational movement of the receiver 220. The receiver 220 is moved rotationally, by an actuator 226, which moves the receiver between a deployed or extended position, shown in FIG. 5A and a non-deployed or retracted position, as shown in FIG. 5B. When the actuator 226 is pulled proximally (as per the arrow 602), the receiver 220 moves outward, into the deployed or extended position (FIG. 5A) for receiving and engaging a shuttle 210, and when pushed distally (as per the arrow 604), moves the receiver 220 into the slot 222 (FIG. 5B) (the non-deployed or retracted position). The actuator 226 is, for example, made of a shape memory alloy, such as Nitinol, and preferably includes a preshaped bend 226x, which acts as a spring, to retract the receiver 220 into the slot 222 to its retracted position. The actuator 226 attaches to a channel 220x in the receiver 220, by one or more of welds, adhesives or mechanical fasteners, such as crimps 605. Additionally, or alternatively, a lock pin 220y holds the actuator 226 in place.

The end of the receiver 220 which extends out of the slot 222, includes a pocket 224 for receiving and engaging the shuttle 210, for example, any of the shuttle needles 210 to 201-7 detailed above. The pocket 224 is typically of a shape corresponding to that of the shuttle 210. In the example illustrated here, a flexible element 224r in the form or a ring or tube is positioned and configured to receive and engage the shuttle when pushed into the pocket, and also to allow extraction of the shuttle by the shuttle transmitter 200, as described herein. In the implementation illustrated here, flexible element 224r is retained by a lock pin 224x extending transversely across at least part of receiver 220.

Figure 6:
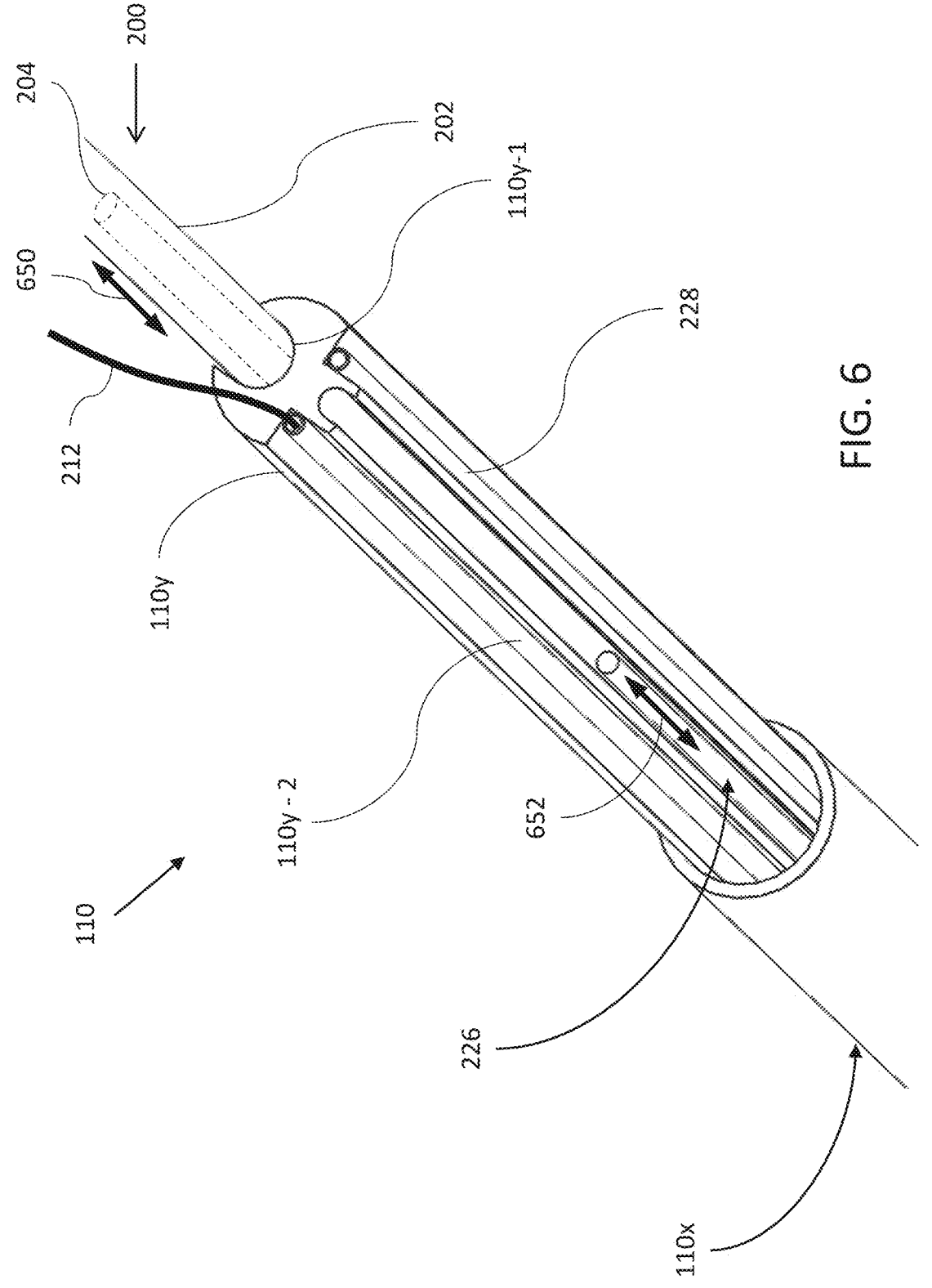
FIG. 6 is a cut away view of the shaft of the suturing apparatus of FIG. 1A.

FIG. 6 shows an exemplary implementation of the shaft 110. In this example, the shaft 110 includes a shaft envelope 110x which supports a shaft insert 110y, which may be implemented as a multi-lumen tube which accommodates a suture conveyor lumen and a bleeder tube. The shaft insert 110y includes a channel 110y-1 which supports the shuttle transmitter 200 by supporting the outer tube 202 so as to be moveable proximally and distally (as indicated by the double headed arrow 650), as is the actuator 226, moveable proximally and distally (as per the double headed arrow 652) along the shaft insert 110y. A suture tubal conveyer 110y-2 facilitates a suture 212 passing therethrough. The bleeder tube 228 is also supported by the shaft insert 110y.

According to certain particularly preferred implementations of the present invention implemented, for example, in the context of a vascular closure device, the device is advantageously integrated with a dilator 150, which serves to dilate the access site into the blood vessel for the shaft 110 and bridging portion 120. The dilator 150 as illustrated here is a tubular structure joined the to a flexible connector 140. The dilator 150, when inserted into a blood vessel, is aligned with the direction of the blood vessel, and is typically at approximately 45 degrees to the longitudinal axis of the suturing device. A rotatable connection is preferably provided at one or both ends of the flexible connector 140 to facilitate rotation of the suturing device to form a circular suture pattern while the dilator remains aligned with the blood vessel and typically does not rotate. The flexible connector 140 should however transfer axial forces from the bridging portion 120 to pull or push the dilator 150 during insertion into and removal from the blood vessel. At the same time, for example, preferably after the dilator 150 is positioned in the blood vessel, the flexible member 140, allows the rotation of the bridging portion 120 around its line of action, for example, without rotation of the dilator 150.

The surfaces of the bridging portion 120, flexible connector 140, and dilator 150 are, in this example, flush with each other, to have a smooth tubal surface. The connection of the dilator 150 to the suturing module 102 is implemented via the flexible connector 140, which, for example, allows the dilator 150 to align itself within the blood vessel, typically at approximately 45 degrees to the bridging portion 120. The flexible connector 140, for example, transfers axial forces from the bridging portion 120 to push or pull the dilator 150 into the blood vessel. When the dilator 150 and bridging portion 120 are placed into the vessel, the flexible connector 140 preferably allows rotation of the suturing module 102 about the dilator 150, without rotation of the dilator 150.

Operation: Suturing Process

1. Shuttle PUSH—First and Subsequent Odd-Numbered Suture Stitches

Attention is directed to FIGS. 7A-7G, which show the shuttle insertion (distal transmission, or "push") process. In describing this shuttle insertion process, which is the first part of the suturing operation, to make a stitch, reference is made to the elements in drawing FIGS. 1A-6, with the descriptions of the elements provided above.

FIG. 7A is the first subprocess of the shuttle insertion and suture insertion process. The suture 212 is joined to the shuttle needle 210, and the shuttle transmitter 200 is retracted into the shaft 110, as shown in FIG. 2B. A portion of the bridging portion 120 has been inserted into the tissue, for example, a blood vessel 1002, this portion including, for example, at least the shuttle receiver 220 and the port 227a for the bleeder tube 228. Should blood exit the port 227b of the bleeder tube 228 in the shaft 110, the position of the bridging portion 120 in the vessel 1002 can be confirmed. The shuttle receiver 220 is deployed or in the extended position, to receive the shuttle needle 210. The bridging portion 120, flexible joint 140 and dilator 150 have been inserted into the vessel 1002 by conventional insertion procedures.

FIG. 7B and FIG. 8A show the next subprocess, where the shuttle needle 210 (with the suture 212), as engaged on the shuttle transmitter 200, e.g., the tube 204 (and the rod 206) is advanced distally toward the shuttle receiver 220.

The shuttle needle 210 continues to be advanced by distal movement of at least the tube 204, such that the pointed tip at the distal end 210d of the shuttle needle 210 contacts the tissue, as shown in FIG. 7C, ultimately piercing and penetrating the tissue, e.g., the blood vessel wall 1002, as shown in FIG. 7D. Additionally, in FIG. 7D, the shuttle needle 210 enters the pocket 224 of the shuttle receiver 220, with distal movement of the shuttle needle 210 continuing until the tip at the distal end 210d, seats in the small diameter section 224c of the pocket 224, acting as a "stopper" for distal movement of the shuttle needle 210. The shuttle needle 210 has now been engaged in the pocket 224 of the shuttle receiver 220, for example, by frictional forces. This corresponds to the state of FIG. 8B. At this point, the shuttle is released by the shuttle transmitter. In the example illustrated here, this is achieved by advancing rod 206 until it engages the proximal portion of the shuttle needle 210 (FIG. 8C) and then withdrawing tube 204 while rod 206 presses distally to hold the shuttle needle 210 in the pocket (FIG. 8D). The shuttle transmitter 200 can then be withdrawn, leaving the shuttle needle in the shuttle receiver pocket. It will be noted that this description applies to a particular non-limiting implementation of the holder and the releaser of shuttle transmitter 200. The corresponding stages according to the alternative implementations will be clear to a person ordinarily skilled in the art.

The tube 204 and rod 206 continue to be retracted proximally, out of the vessel 1002 and tissue, as shown in FIG. 7F, until fully retracted into the outer tube 202 and the shaft 110, as shown in FIG. 8G. As shown in FIGS. 7E, 7F and 7G, the shuttle needle 210 holding the suture 212 is engaged (held or gripped) in the pocket 224 of the shuttle (needle) receiver 220, by frictional forces, as described above.

2. Shuttle PULL—Second and Subsequent Even-Numbered Suture Stitches

Attention is directed to FIGS. 9A-9G, which show the shuttle retraction (proximal transmission, or "pull") process. The corresponding operation of the rod 206 and tube 204 may be understood as corresponding to the states of FIGS. 8A-8E in reverse order. In describing this shuttle retraction process, which is the second part of the suturing operation, to make a stitch, reference is made to the elements in drawing FIGS. 1A-6, with the descriptions of the elements provided above.

Figures 9A, 9B, 9C, 9D, 9E, 9F, 9G:
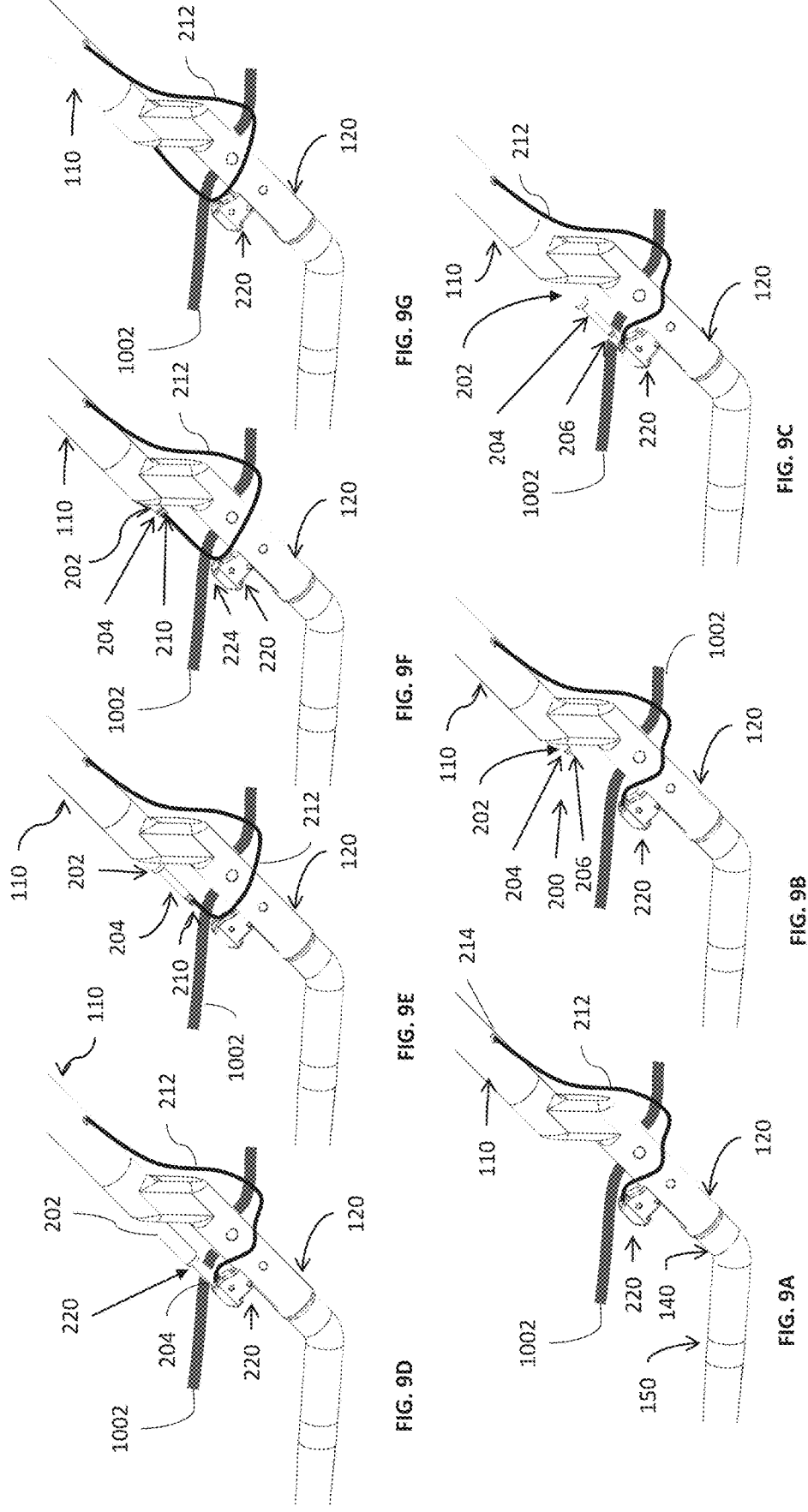
FIGS. 9A-9G are diagrams of an operational sequence for shuttle (needle) retraction.

In FIG. 9A, the suture 212 has been let out of the shaft 110 and the bridging portion 120 and the shaft 110 have been rotated (from the position shown in FIG. 7G), such that the shuttle transmitter 200 and the outer tube 202, tube 204 and rod 206, are aligned with the pocket 224 of the shuttle receiver 220, which is engaging (holding or gripping) the shuttle needle 210, holding the suture 212.

The shuttle transmitter 200, i.e., the outer tube 202, tube 204 and rod 206, are now retracted, by being moved distally out of the shaft 110, as shown in FIG. 9B. The distal movement continues as the piercing tip 206a of the rod 206 pierces the tissue and the vessel 1002, with the tube 204 also moving distally, following the rod 206, as shown in FIG. 9C.

As shown in FIG. 9D, the rod 206 and tube 204 enter the pocket 224 and the rod 204 contacts the shuttle needle 210 at the recess 302, while the tube 204 frictionally engages the shuttle needle 210. This frictional engagement of the tube 204 with the shuttle needle 210 is with forces strong enough, such that when the tube 204 and rod 206, are retracted, by being moved proximally, the shuttle needle 210 is gripped and engaged by the tube 204, with forces sufficient to break the engagement of the shuttle needle 210 by the pocket 224.

In FIG. 9E, the tube 204 and rod 206 are retracted by being moved proximally, with the shuttle needle 210 gripped (engaged) by the tube, for example, by frictional forces, such that the shuttle needle 210, with the suture 212 is retracted. The retraction continues, as the shuttle needle 210, engaged by the tube 204, the tube 204, the rod 206, and optionally the outer tube 202, are moved proximally, as shown in FIG. 9F. The proximal movement of the shuttle needle 210, engaged by the tube 204, the tube 204, the rod 206, and optionally the outer tube 202, is complete, as shown in FIG. 9G, as their elements are now all inside of the shaft 110.

The apparatus 100 may now be returned to the position and orientation of, or similar to that shown in FIG. 7A, to perform a next or subsequent suture.

A sequence of suture stitches performed according to the sequence of FIGS. 7A-9G may be used to form a wide range of suturing patterns, preferably including an even number of suturing (penetration) points. Examples include, but are not limited to, a Purse-String Suture pattern (PSS), preferably with an even number of suturing points, and typically at least 4 suturing points, and most preferably 6 or 8 suturing points. Other running stitch patterns may also be formed, and in particular, a spiral suture, where some or all of the stitches cross between two sides of an incision or wound, or between adjacent edges of two side-by-side materials, and where relative motion between successive stitches advances the device along the edges of the material. One or both ends of a suture may be anchored by performing multiple stiches in overlapping relation by repeated penetration in closely adjacent locations on the material, thereby achieving a self-locking or knotted fixing of the end of the suture. This technique may be used either at the beginning or end of a suture, or both.

Figures 10A, 10B, 10C:
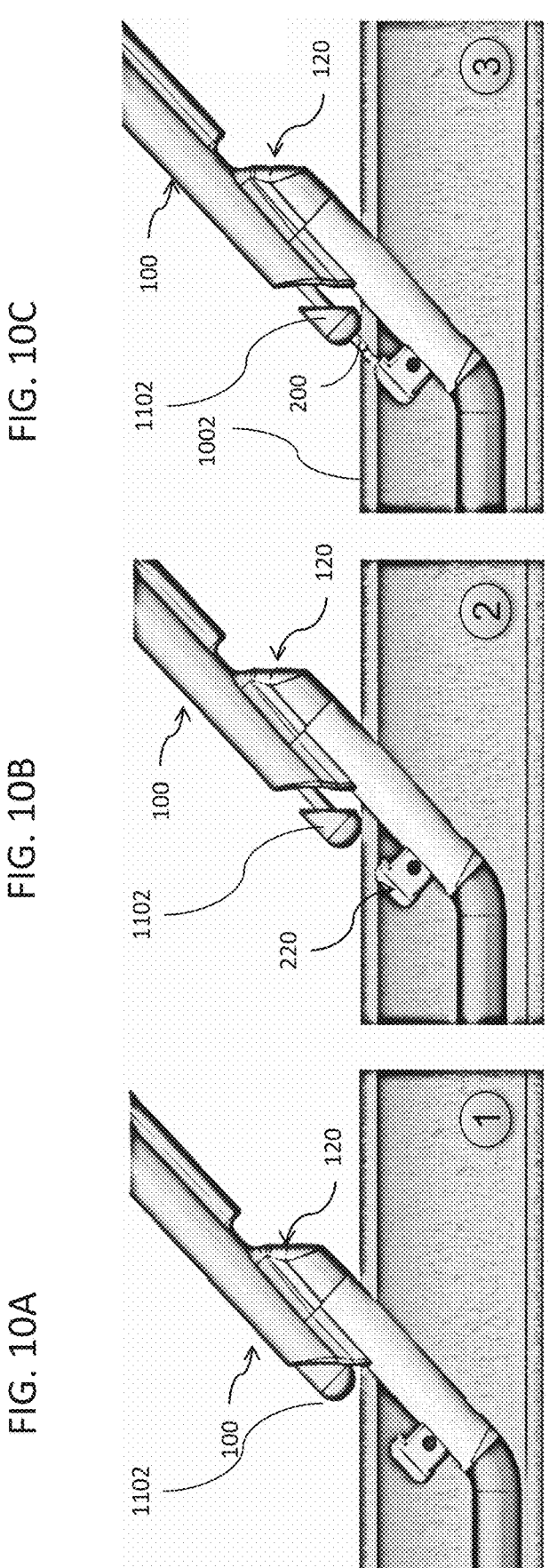
FIG. 10A-10C are diagrams of a preload member for the apparatus of FIG. 1A.

FIGS. 10A-10C show a variant embodiment, where the apparatus 100 includes a preload member 1102 as part of the needle transmitter 200. The preload member 1102 may be activated prior to any needle 210 insertion or retraction through a sutured media. The distal end 1102a of the preload member 1102, for example, has a spherical shape to allow implementation of pinching forces at different angles on tubal surfaces, such as blood vessel walls. In FIG. 10A there is shown a cross section of a blood vessel 1002 with the suturing module in an initial position. In FIG. 10B, the blood vessel 1002 wall is pinched, thereby immobilizing the tissue for clean penetration. In FIG. 10C, a suture is implemented.

Although not limited to such implementations, the suturing device is most preferably implemented as a minimally-invasive suturing device including an elongated body for percutaneous insertion, and wherein a user input and a linkage (to be described below) are implemented as part of a handle associated with a proximal end of the elongated body. The phrase "elongated body" is used herein to refer broadly and collectively to the dilater, bridging portion and shaft of the suturing mechanism described thus far. The shuttle transmitter thus extends along a proximal portion of the elongated body, either internally or externally.

HMI Module Overview and Implementation Options

Figures 11A, 11B, 11C:
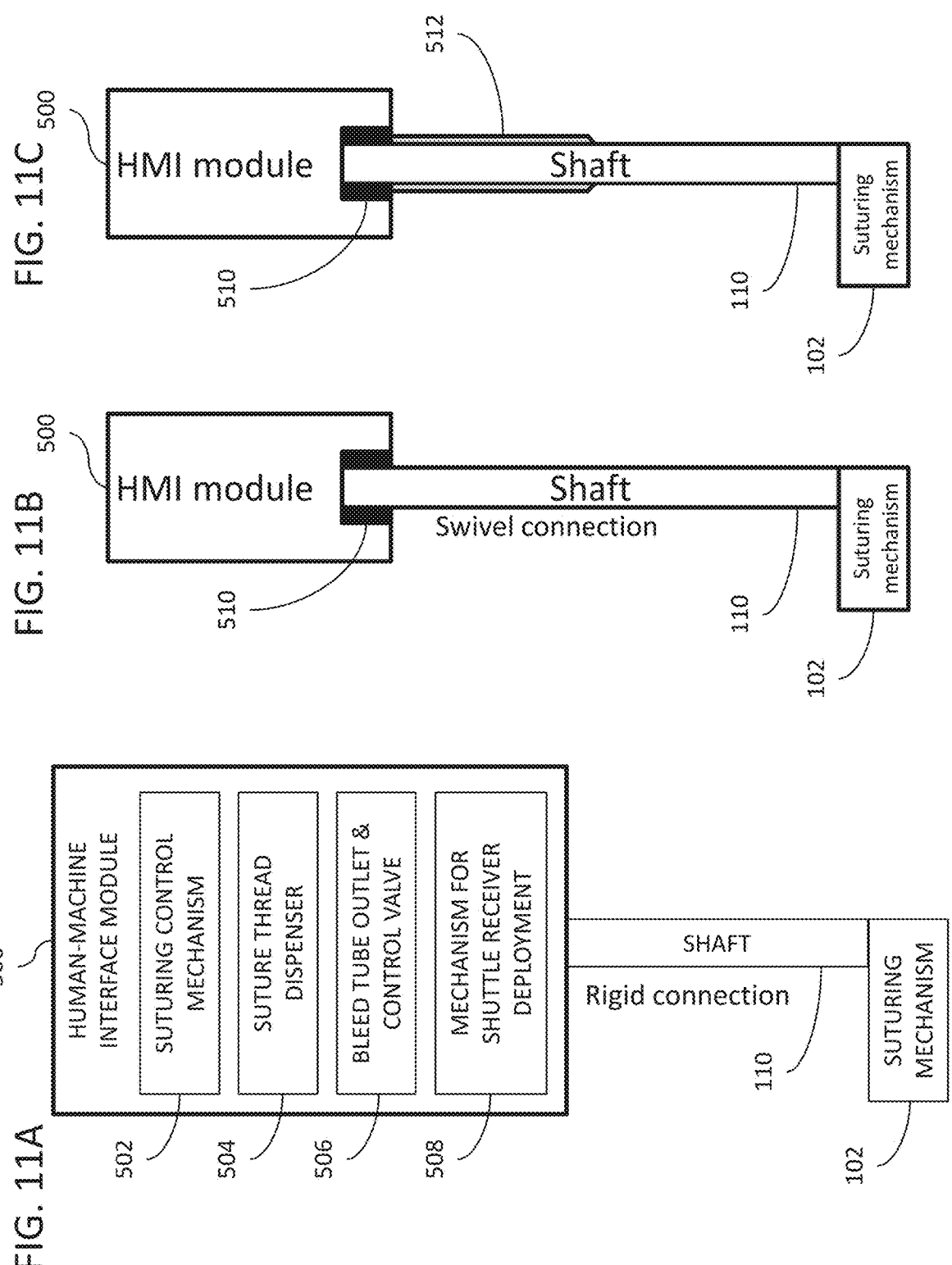
FIG. 11A is a schematic block diagram of a suturing system including a human-machine interface (HMI) module.
FIGS. 11B and 11C are simplified schematic views similar to FIG. 11A illustrating additional options for swivel connection between a device shaft and the HMI module.

Certain aspects of the present invention relate to features of a human-machine interface (HMI) module, typically at least partially integrated with a handle 130 or other user-grippable holder, connected to an elongated body with which the suturing mechanism 102 is associated. A schematic functional representation of the HMI module 500 is illustrated in FIG. 11A, where HMI module 500 is illustrated as including one or more of the following subsystems: a suturing control mechanism 502 for controlling operation of the suturing mechanism 102, a suture thread dispenser 504, a bleed tube outlet and control valve 506, and a mechanism 508 for controlling deployment of shuttle receiver 220. Each of these subsystems will be further elaborated below. For simplicity of presentation, the HMI module 500 is shown schematically in other drawings herein as a simple rectangle without detailing these subsystems, but it should be understood that, in each case, it may include all or some of the subsystems shown in FIG. 11A.

The HMI (and suturing control) module may be implemented in a range of different embodiments. The unit may include mechanical elements such as gear train, cam and cam followers, levers and combinations thereof, electromechanical elements and actuators, such as DC motors, brushless motors, piezo-electrical actuators, etc., and sensors such as force sensors, position sensors, pressure sensors, etc., optionally with connective elements to external power source, preferably to internal power source. In certain embodiments, the HMI module may include electrical circuitry with logical components such as PLC, memory, motion controllers, wire or wireless components. The electrical circuitry may be external to the HMI module. Connections may be provided to facilitate activation and control of the HMI module with the use of an external module, such as by robotic control, and various different interface elements may be employed to provide user inputs to the HMI module, such as mechanical elements such as levers and knobs, and electro-mechanical elements such as switches, touch sensors, force sensors, etc.

Referring to FIGS. 12A-12D, it is noted that various suturing applications of the present invention require motion of the suturing mechanism relative to the sutured material (e.g., tissue) between successive stitches. In a first particularly preferred but non-limiting set of applications, the relative motion is achieved by rotating the suturing mechanism about a longitudinal axis, particularly in the region of bridging portion 120, thereby achieving a pattern of stitches about an opening through which the elongated body is inserted. FIGS. 12A-12D illustrate schematically a number of options regarding how this motion may be generated using different implementations of HMI module 500.

FIG. 12A illustrates a one-unit HMI implementation. In this case, a suture pattern is implemented by repeatable, typically axial, actuation of the suturing mechanism (through controls located on the unit body) followed by rotation of the unit to relocate the suturing mechanism at different piercing points FIG. 12B illustrates a two-unit HMI implementation. In this case, a first stationary unit (optionally the lower unit, as illustrated) allows for locating the HMI module relative to the suturing site, and remains static throughout the suturing procedure. A second unit (optionally the upper unit, as illustrated) is displaceable for implementing typically axial suturing actions (through controls located on the unit body) and second, rotational movement for relocating the suture mechanism at different piercing points. Controls to actuate the suturing mechanism are preferably located at the second unit.

FIG. 12C illustrates schematically a two-unit HMI implementation in which a first unit, preferably the lower one, is rotatable for locating the HMI module relative to the suturing site. This unit may be connected directly to the shaft to rotate the device and relocate the suturing mechanism at different piercing points. A second unit, preferably the upper unit as illustrated here, controls the displacements, typically in the axial direction, preferably through corresponding controls located on the unit body, of the suturing mechanism to effect suturing stitches at each location. A combination of the second unit operation at a sequence of locations selected by the first unit position results in a desired suturing pattern.

FIG. 12D illustrates schematically a single-unit HMI which provides external features to facilitate locating the HMI module relative to the suturing site and includes mechanisms, optionally internal, and preferably with externally accessible input features, for activation of the suturing mechanism to effect suture stitches, and for rotating the suturing mechanism to new piercing points, thereby generating a desired suturing pattern. In this embodiment, the suturing controls may preferably be located on the external unit, or on a remote module (not shown) having an electromechanical interface with the HMI module.

Depending on which of these form-factors is selected, various different types of mechanical interface may be implemented between the HMI module 500 and the shaft 110, as illustrated in FIGS. 11A-11C. In the case of FIG. 12A, the HMI module 500 is advantageously rigidly attached to shaft 110, as illustrated schematically in FIG. 11A, so that rotation of the HMI module/handle rotates the suturing mechanism between target positions. The same may be true of the lower module of FIG. 12C. In other cases, shaft 110 may advantageously be connected to HMI module 500 via a swivelable (rotatable) connection, so that the device shaft can be rotated to the desired suturing position for the next stitch while part or all of the HMI module 500 remains stationary. Connections of this sort are illustrated schematically in FIGS. 11B and 11C, where a bearing 510 provides a swivel connection between shaft 110 and at least part of HMI module 500. Optionally, as illustrated in FIG. 11C, at least part of swivelable shaft 110 may be surrounded by a tubular member (sleeve) 512 which is rigidly connected to the HMI module 500.

The form of interconnections between the various parts of the HMI module 500 will also vary between the different configurations of FIGS. 12A-12D, as will now be explained with reference to FIGS. 13A-16B. Specifically, FIGS. 13A and 13B illustrate the case of a rigid connection between the HMI module and the shaft. In this case, the HMI module is rotated to move the suturing mechanism to a new piercing point while the axial actuation of the suture mechanism is activated by controls located on the HMI module.

FIGS. 14A and 14B illustrate a semi-swivelable connection between the HMI module and the shaft. In this case, the first unit, preferably the lower, may include some of the HMI module control elements, and is connected directly to the shaft for rotating the device and relocate the suturing mechanism at different piercing points. The second unit, preferably upper, used for activation of the suturing mechanism to effect a suturing pattern, may include other controls of the HMI module, as labeled.

FIGS. 15A and 15B illustrate a reversed semi-swivelable connection between the HMI module and the shaft. Here too, a first unit (preferably the lower) is for applying, typically axial, activations of the suturing mechanism (through controls located on the unit body) to effect a suturing pattern. A second unit (preferably upper) is used for rotating (relocating) the suturing mechanism at different piercing points. The upper unit is preferably connected directly to the shaft.

FIGS. 16A and 16B illustrate an implementation with a swivelable connection between the HMI module and the shaft. In this scenario, the HMI module is stationary while the axial and rotational motions of the suturing mechanism, to effect a suture pattern, are performed by controls located on the HMI module or at a remote location. The HMI module may also include a subunit connected to the shaft for allowing the display of shaft rotation.

Figures 17, 18:
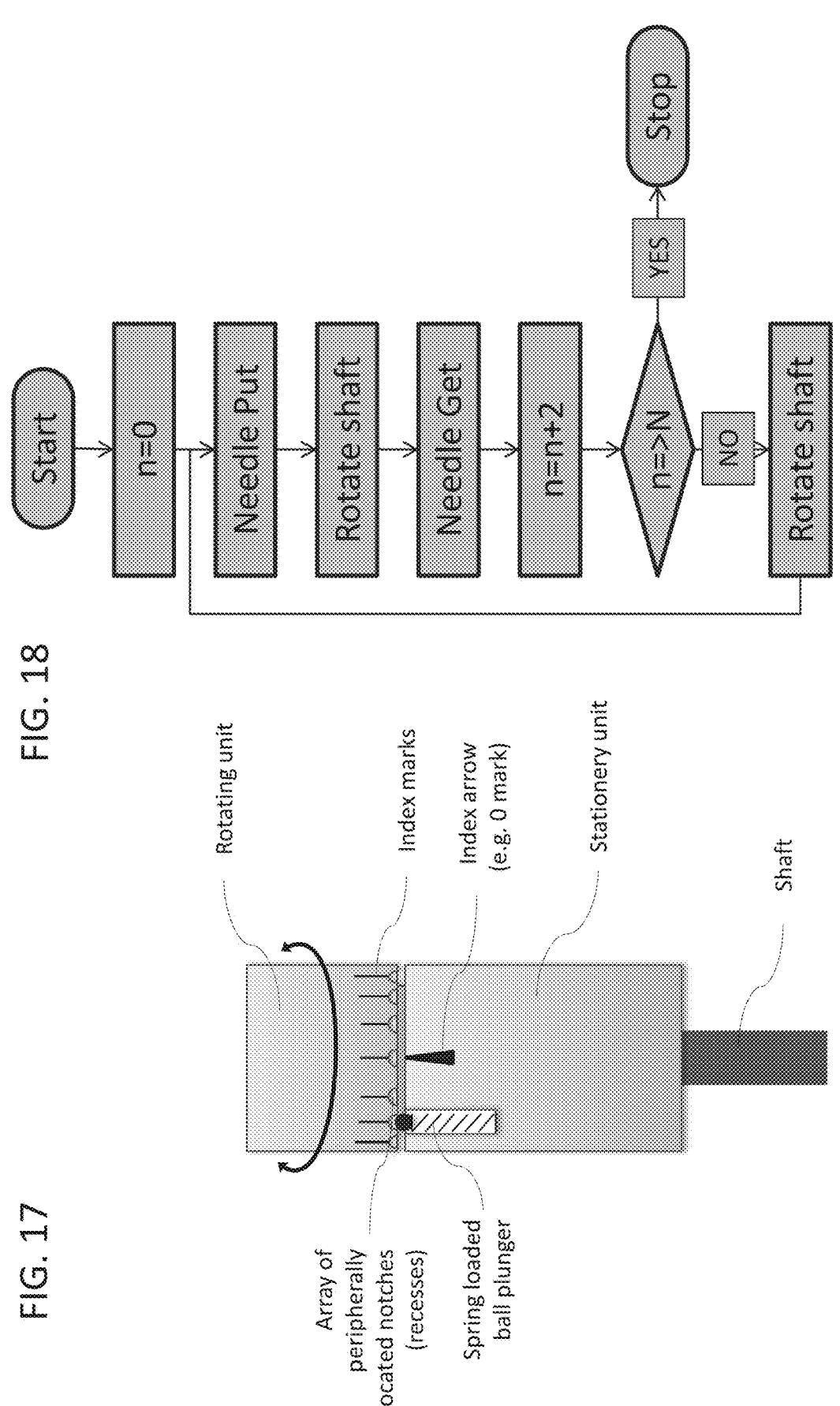
FIG. 17 is a schematic illustration of a notched arrangement for indexing rotations positions of a suturing mechanism.
FIG. 18 is a state diagram representing a mode of operation of a suturing system according to an aspect of the present invention.

Wherever rotational motions between two suturing locations are controlled by relative rotation between a rotatable element (connected to the shaft) and a static (non-rotating) element, it may be advantageous to provide indexing by use of indexing marks and/or positive tactile feedback. This may be achieved using a spring-loaded element, such as a ball bearing, that engages a sequence of corresponding recesses, thereby defining distinct indexing positions at predefined positions or angular intervals. This is illustrated in FIG. 17.

HMI Module Operation Sequence

As detailed above particularly with reference to FIGS. 8A-8E, operation of the suturing mechanism requires a particular sequence of operations of the shuttle transmitter, coordinated with relocations of the device, to perform a sequence of bidirectional suture stitches together forming a running stitch to-and-fro through the tissue (or other sutured material).

Specifically, after initial deployment of the suturing mechanism and positioning for the first suture stitch, the HMI module 500 should generate the following sequence of operations:

First Stitch—Proximal-To-Distal ("PUSH" or "PUT"):
   i. axial displacement of the shuttle transmitter from the withdrawn position to the penetrating position so as to penetrate the material at a first location (referred to below as "penetrate material");
   ii. reconfiguration of the shuttle transmitter from the shuttle holding state to the shuttle releasing state (referred to below as "release shuttle");
   iii. axial displacement of the shuttle transmitter from the penetrating position to the withdrawn position so as to withdraw from the material leaving a first suture stitch at the first location (referred to below as "withdraw");
   iv. as part of the shuttle-release reconfiguration, or as a separate action, forming a penetration configuration of the shuttle transmitter without the shuttle, ready for penetration as part of a subsequent "PULL" stitch cycle (typically included in "release shuttle");
Repositioning 1:
   v. repositioning of the shuttle transmitter and the shuttle aligned at a second or subsequent even-numbered stitch location (referred to below as "displace to next location");
Second Stitch—Distal-To-Proximal ("PULL" or "GET"):
   vi. axial displacement of the shuttle transmitter from the withdrawn position to the penetrating position so as to penetrate the material at the second location (referred to below as "penetrate material");
   vii. reconfiguration of the shuttle transmitter from the shuttle releasing state to the shuttle holding state so as to hold the shuttle (referred to below as "hold shuttle");
   viii. axial displacement of the shuttle transmitter from the penetrating position to the withdrawn position so as to withdraw the shuttle from the material forming a second suture stitch at the second location (referred to below as "withdraw");
   ix. as part of the shuttle-hold reconfiguration, or as a separate action, forming a penetration configuration of the shuttle transmitter together with the shuttle, ready for penetration as part of a subsequent "PUSH" stitch cycle (typically included in "hold shuttle");

Repositioning 2:

x. for all cycles other than the last stitch, repositioning of the shuttle transmitter and the shuttle aligned at a subsequent odd-numbered stitch location (referred to below as "displace to next location").

While it would be possible to implement a number of separate user controls/inputs for performing these different operations, according to one non-limiting aspect of the present invention, a simplified interface is provided in which some or all of these operations are actuated by displacements of a user input unidirectionally or bidirectionally. A suitably designed linkage is used to convert the unidirectional or bidirectional displacements of the user input into the required sequence of operations, optionally including the repositioning, or with the repositioning being performed through a separate operation. A number of non-limiting exemplary mechanisms for providing this functionality will be described herebelow.

The term "linkage" is used herein in the description and claims to refer to any combination of elements that define a causal relationship between the movement of the user input and the various outputs required to achieve the required operations. The "linkage" thus defined may include a number of mechanisms that operate in parallel, and may include purely mechanical components or various electromechanical or otherwise powered or power-assisted components. Most preferably, the linkage is a mechanical linkage.

The user input may be any suitable input. Examples include, but are not limited to, a button, a slider, a lever and a rotatable knob. The actuation of the user input may be unidirectional, such as a button, slider or lever which returns to its original position under spring bias, or a rotatable knob which completes a sequence of operation by returning to its starting position. In the case of a user input which returns under spring bias, the return motion may be a neutral motion which does not perform any operations of the suturing mechanism, or may also be coupled through the linkage to perform one or more additional operation of the suturing mechanism.

Alternatively, the user input may be actuated bidirectionally, such as a slider or lever which is actively displaced linearly, pivotally or otherwise, first in one direction and then in a reverse direction, or a pair of opposing buttons which are depressed alternately to generate motion of a single user input in opposite directions. In the case of two opposing buttons, these are considered herein to be bidirectional operation of a single user input if they act on the same input element of the linkage in opposite directions, as exemplified by the example of FIG. 22, discussed below.

According to a first particularly preferred subset of implementations of the present invention, the user input is a mechanically-operated user input in which the user provides mechanical force which is converted by the linkage to perform the various operations of the suturing mechanism. However, implementations in which the user input force is supplemented or substituted by force from another source when performing one or more of the suture mechanism operations also fall within the scope of this aspect of the present invention. Sources of such forces may be a pretensioned arrangement of one or more spring, or an actuator driven by any suitable source of energy, either onboard or externally provided, such as electrical power or fluid pressure.

In the particular non-limiting but preferred implementation of the suturing mechanism described above, the operations of "release shuttle" and "hold shuttle", as well as the corresponding reconfigurations into first and second penetrating configurations, are achieved by differential axial displacements of a shuttle holder 204 and a shuttle ejector 206. This aspect of the present invention will be exemplified below with reference to linkages which achieve the corresponding required relative axial displacements to operate this exemplary mechanism. It should be noted, however, that alternative implementations of a shuttle transmitter which performs the functions of "release shuttle" and "hold shuttle" by some other mechanism, such as a mechanism employing relative axial rotation between two elements, also fall within the scope of this aspect of the present invention.

It is a particularly preferred feature of certain implementations of this aspect of the present invention that there is provided a drive mechanism for operating a suturing mechanism with suture-carrying shuttle driven bidirectionally through a material by a shuttle transmitter where the drive mechanism includes a user input displaceable through a range of motion and a linkage mechanically associated with the user input and with the shuttle transmitter. The linkage is configured to convert displacements of the user input unidirectionally or bidirectionally into a sequence of operations of the shuttle transmitter including:

A. the operations to perform a first (or odd-numbered) suture stitch, including the operations defined above as: penetrate material (with the shuttle); release shuttle; withdraw (without the shuttle), and then, after repositioning of the shuttle transmitter and the shuttle aligned at a second location, B. the operations to perform a second (or even-numbered) suture stitch, including the operations defined above as: penetrate material (without the shuttle); hold shuttle; withdraw (with the shuttle).

By further repositioning the shuttle transmitter in subsequent positions and repeating the above sequence, it is preferably possible to perform further stitches, typically in pairs, to form a running stitch suture with any desired sequence of penetration locations and a corresponding stitching pattern.

The repositioning may be performed manually, or may also be effected by the linkage as a result of the user input, as will be exemplified below.

The operations to form each suture stitch may be executed by one entire cycle of motion of the user input (e.g., a to-and-fro motion), by a part of a cycle (e.g., a unidirectional displacement without a return motion), or by a plurality of cycles of motion of the user input. In any case, the cycle of motion of at least part of the linkage preferably occurs over a motion corresponding to two suture stitches, since successive stitches are necessarily distinct in the suturing mechanism operations to be performed, with odd stitches performing a shuttle PUT operation and even stitches performing a shuttle GET operation, all as detailed above.

Exemplary Motion Transformations

In the case of to-and-fro motions between end points "A" and "B", such as linear displacements of a button or slider, or angular displacements of a lever, the operations performed by the linkage may be mapped to the motion of the user input in any desired combination and, by way of non-limiting example, may be according to any of the following:

Example 1

| Location | Motion | Shuttle Transmitter Operations |
|---|---|---|
| First/odd locations | A => B | Penetrate material; release shuttle; withdraw; displace to next location |
| | B => A | None |
| | Supplementary | None |
| Second/even locations | A => B | Penetrate material; hold shuttle; withdraw; displace to next location |
| | B => A | None |
| | Supplementary | None |

EXAMPLE 2

| Location | Motion | Shuttle Transmitter Operations |
|---|---|---|
| First/odd locations | A => B | Penetrate material; release shuttle; withdraw |
| | B => A | Displace to next location |
| | Supplementary | None |
| Second/even locations | A => B | Penetrate material; hold shuttle; withdraw |
| | B => A | Displace to next location |
| | Supplementary | None |

Example 3

| Location | Motion | Shuttle Transmitter Operations |
|---|---|---|
| First/odd locations | A => B | Penetrate material; release shuttle; withdraw |
| | B => A | None |
| | Supplementary | Manually displace to next location |
| Second/even locations | A => B | Penetrate material; hold shuttle; withdraw |
| | B => A | None |
| | Supplementary | Manually displace to next location |

Example 4

| Location | Motion | Shuttle Transmitter Operations |
|---|---|---|
| First/odd locations | A => B | Penetrate material; release shuttle; withdraw |
| | Supplementary | Manually displace to next location |
| Second/even locations | B => A | Penetrate material; hold shuttle; withdraw |
| | Supplementary | Manually displace to next location |

Example 5

| Location | Motion | Shuttle Transmitter Operations |
|---|---|---|
| First/odd locations | A => B | Penetrate material; release shuttle |
| | B => A | Withdraw; (displace to next location) |
| | Supplementary | None (or displace to next location) |

-continued

| Location | Motion | Shuttle Transmitter Operations |
|---|---|---|
| Second/even locations | A => B | Penetrate material; hold shuttle |
| | B => A | Withdraw; (displace to next location) |
| | Supplementary | None (or displace to next location) |

Example 6

| Location | Motion | Shuttle Transmitter Operations |
|---|---|---|
| First/odd locations | A => B | Penetrate material |
| | B => A | Release shuttle; withdraw; (displace to next location) |
| | Supplementary | None (or displace to next location) |
| Second/even locations | A => B | Penetrate material |
| | B => A | Hold shuttle; withdraw; (displace to next location) |
| | Supplementary | None (or displace to next location) |

For rotary inputs, such as a rotatable knob, the range of options generally parallel the above examples, with motion from A to B, or the entire cycle A-B-A, typically being mapped to rotation through a full turn or half-a-turn. Two non-limiting examples follow:

Example 7 (Rotary User Input)

| Location | Motion | Shuttle Transmitter Operations |
|---|---|---|
| First/odd locations | 0°-180° | Penetrate material; release shuttle; withdraw |
| | Supplementary | Displace to next location |
| Second/even locations | 180°-360° | Penetrate material; hold shuttle; withdraw |
| | Supplementary | Displace to next location |

Example 8 (Rotary User Input)

| Location | Motion | Shuttle Transmitter Operations |
|---|---|---|
| First/odd locations | 0°-360° | Penetrate material; release shuttle; withdraw |
| | Supplementary | Displace to next location |
| Second/even locations | 0°-360° | Penetrate material; hold shuttle; withdraw |
| | Supplementary | Displace to next location |

Turning now to FIG. 18, in come cases, it may be helpful to describe the operation of the suturing mechanism by the drive mechanism in terms of a logical "state machine" for performing N stitches (typically an even number). FIG. 18 illustrates such a description, where "Needle Put" and "Needle Get" each represent the corresponding sequence of operations of the needle transmitter as detailed above (the shuttle being referred to interchangeably as a "needle" for the example in which the shuttle has a penetrating tip). As per the various examples described above, the "Rotate shaft" operation (an example of displacement to the next stitch location) may be performed by the drive mechanism, or may be a manual operation by the user. The stop condition may be based on a user decision according to the progress of the stitching process, or may be a mechanical "brake". N is typically 6 or 8, although other numbers may be used.

A number of possible implementations of the drive mechanism will now be described on a schematic level with reference to FIGS. 19A-24B. It should be noted that these examples are presented here in schematic terms only, to illustrate operating principles sufficient to allow practical implementation of the invention, but without regard to scale, details of gear teeth or numerous other details that will be readily determined by one ordinarily skilled in the art when implementing such mechanisms.

Figure 19A:
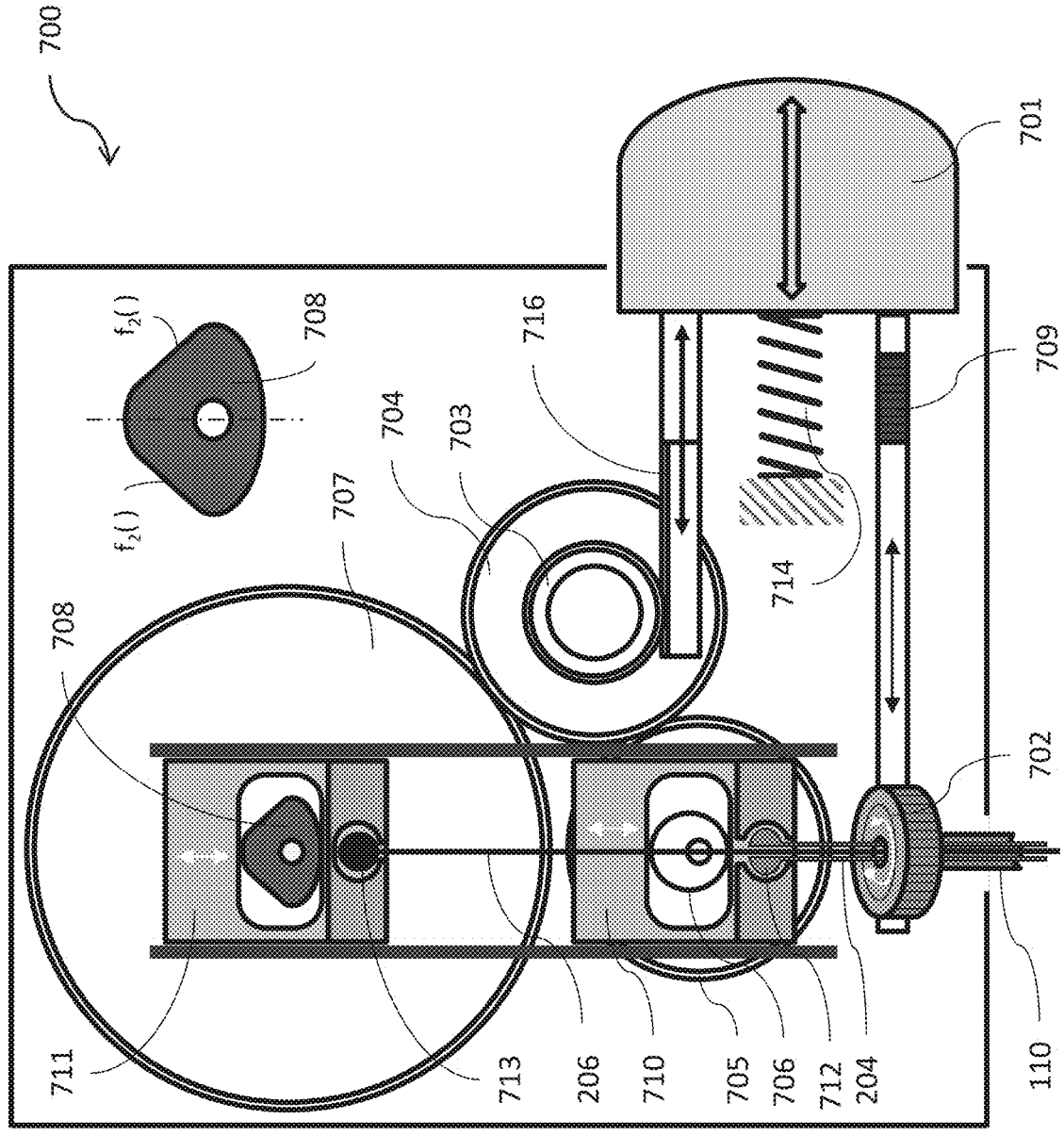
FIG. 19A is a schematic representation of a drive mechanism for operating a suturing mechanism according to an aspect of the present invention.

Turning now to FIG. 19A, this illustrates a drive mechanism 700 for synchronizing operation of a suturing mechanism such as that described above based on unidirectional displacement of a user input in the form of push button 701. Dimensions of the different gear wheels, cams and other elements are not to scale and do not present actual gearing ratios.

Each press on push button 701 activates either a PUT needle action or a GET needle action per FIG. 18, followed by the device shaft and suture mechanism axial rotation through a predefined angle to a new piercing point (e.g. by 60 degrees for 6 stitches encircling an opening). One-way bearings 702,703 activate the mechanism only during button pressing. Each bearing is interlocked with an external gear wheel. Activation of the one-way bearing is effected by gear racks 202 and 709, respectively.

A gear ratio between gear wheels 704 and 705 rotates cam 706 by 360 degrees while at the same time the gear ratio between gear wheels 704 and 707 rotates cam 708 by only 180 deg. per depression of button 701.

Cam 706 may have a simple eccentric profile with eccentric amplitude per a motion function $f_1(\ )$ corresponding to the required to-and-fro motion of the shuttle holder. Cam 706 is engaged in an opening in a slider 710, acting as double-sided flat cam follower. Cam 708 may have a profile of a function $f_2(\ )$ corresponding to the required motion of the shuttle ejector, projected (and mirrored) over 180 deg. of the cam profile. Slider 711 has a similar opening for cam 708.

An additional gear rack 709, also connected to button 701, has a position and length designed to rotate one-way bearings 702 only after cam 706 has rotated 360 degrees and cam 708 has rotated 180 degrees. One way bearing 702 preferably rotates both device shaft 110 together with the suturing mechanism needle transmitter tube and rod members 204 and 206. Cam 706 activates axial motion of slider 710 while cam 708 activates axial motion of slider 711. Advantageously, slider 710 is connected to the tubular member 204 through a swivel joint 712 while slider 711 is connected to the ejector (rod) member 206 through a swivel joint 713. A spring 714 returns button 701 to its initial position without generating any further motion, as a result of the one-way bearings 702 and 703.

Figure 19B:
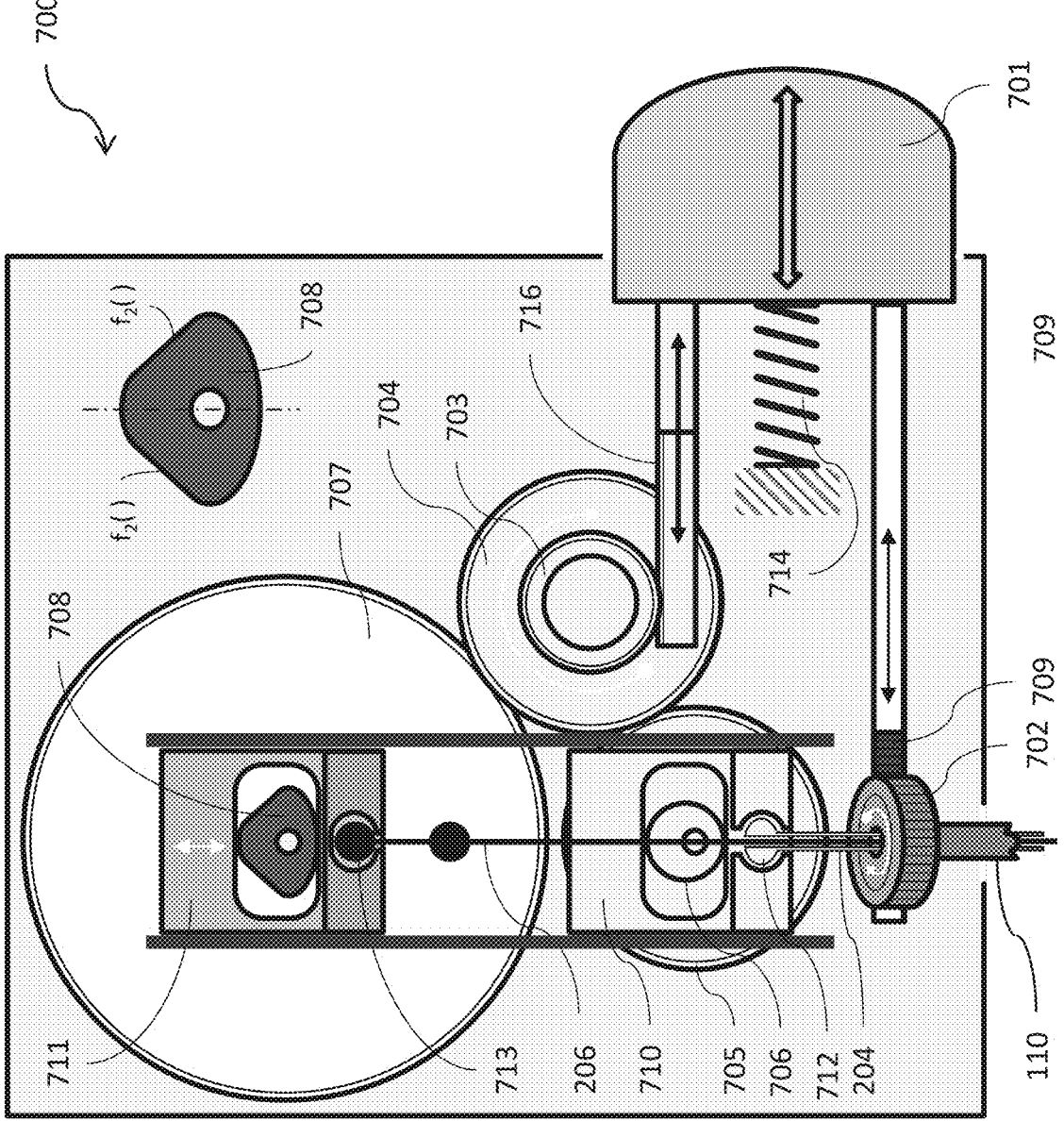
FIG. 19B is a schematic representation of a variant of the drive mechanism of FIG. 19A.

FIG. 19B illustrates a variant implementation of drive mechanism 700 which is generally similar to that of FIG. 19A, with equivalent elements labeled similarly. This implementation differs from FIG. 19A in that the location of the gearing section on rack 709 is here located near the distal end of the rack and the direction of rotation of the one way bearing 702 is reversed. In this case, rotation of the device shaft 110, together with the suturing mechanism, will occur during the return motion of button 701, after completion of a needle PUT or GET sequence during the inward depression of button 701.

Figure 20:
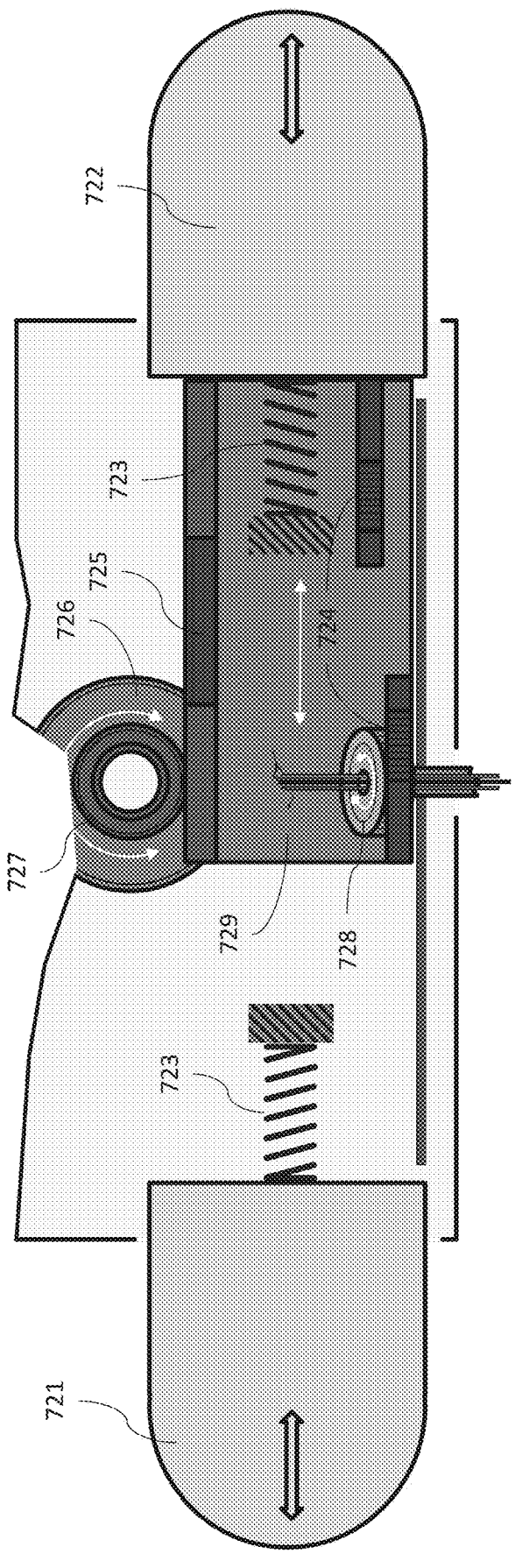
FIG. 20 is a schematic representation of a further variant of the drive mechanism of FIG. 19A.

Turning now to FIG. 20, this is a partial illustration of a further variant implementation of the drive mechanism of the present invention in which the HMI module is implemented with a pair of opposing buttons 721 and 722 which are alternately depressed to actuate a PUT needle action and a GET needle action, respectively. The buttons may be arranged and used in several, non-limiting embodiments such as:

Two separate buttons, each preloaded with a spring 723, and each having its own gear racks 724 and 725, and optionally separate linkage elements such as gear wheels 726, 727 and 728.

Two buttons connected together by gear racks 725 and 724 working together as a single bidirectional shuttle-member carrying the gear racks.

Two separate buttons, each preloaded with a spring 723, where both buttons act on a single, separate shuttle slider 729, combining both gear rack 724 and gear rack 725 as a single element.

The device may be supplied with the shuttle slider 729 arranged as to internally press the first button while disengaged from second button. Motion of the shuttle slider from side to side by the user, from one button to the other, will typically effect a PUT or GET needle action.

Optionally, two shuttle sliders 729 may be arranged on opposite sides of the one-way bearings 728 in order to rotate the suture mechanism only when the PUT or GET needle actions are complete. A gap between the racks may advantageously be longer than the rack section length. A gear wheel 727 may advantageously transfer motion to gear wheel 726 in both directions, depending on the implementation of the mechanism. The remainder of the linkage is not illustrated in FIG. 20, but may be generally similar to the linkage described with reference to FIG. 19A, or to that described below with reference to FIG. 21A, where gear wheel 727 of FIG. 20 may be regarded as gear wheel 704 of FIG. 19A or gear wheel 733 of FIG. 21A. The other elements not shown in this figure may be similar to elements described in FIG. 19A or FIG. 21A.

It will be noted that the linkage in the drive mechanisms of FIGS. 19A and 19B includes a first transmission (gear wheels 704 and 705, eccentric cam 706 and slide 710) defining a first timing profile for motion of the shuttle holder 204 as a function of displacement of the user input 701 and a second transmission (gear wheels 704 and 707, shaped timing cam 708 and slide 711) defining a second timing profile for motion of the shuttle ejector 206 as a function of displacement of the user input 701. At least the second timing profile defines motion of the shuttle ejector 206 as a function of displacement of the user input 701 over two cycles of displacement of the shuttle transmitter from the withdrawn position to the penetrating position and back to the withdrawn position, and the motion over a first of the two cycles is non-identical to the motion over a second of the two cycles.

Figures 21A, 21B:
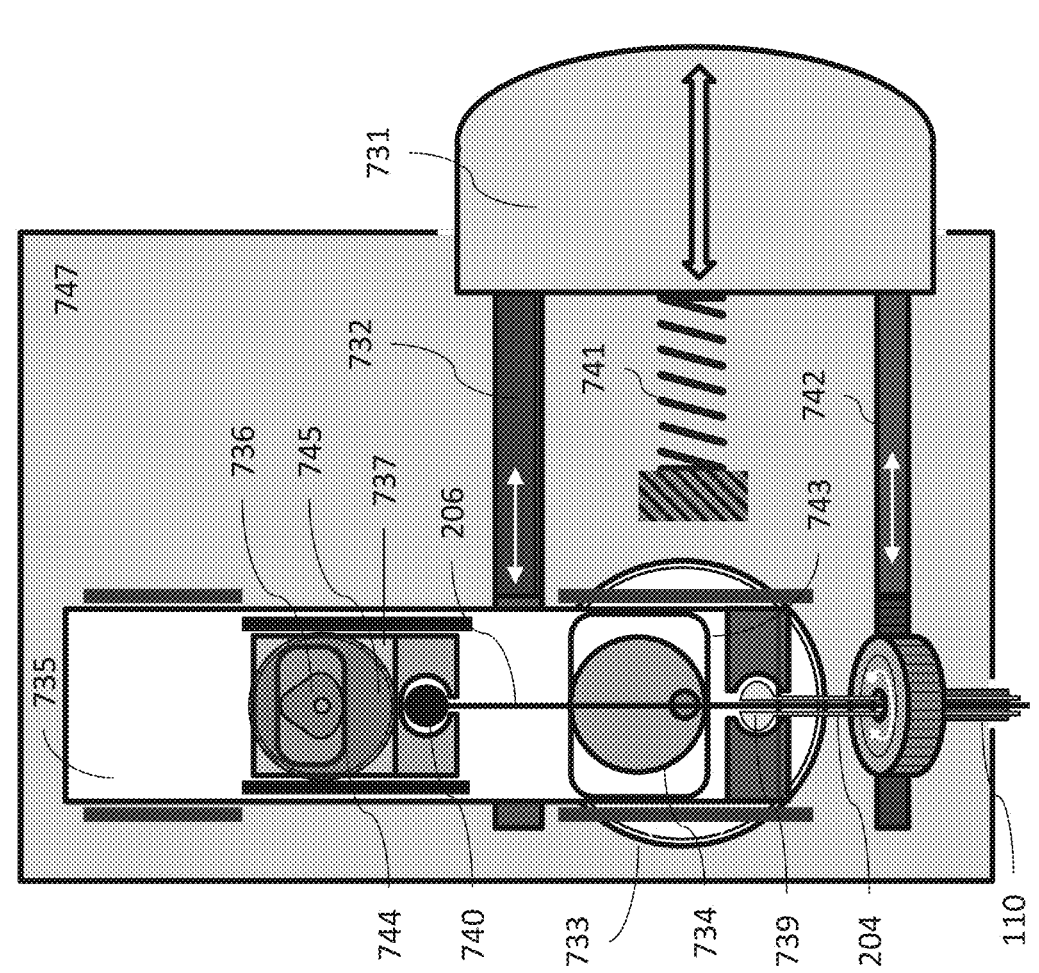
FIG. 21A is a schematic representation of a further variant of the drive mechanism of FIG. 19A.
FIG. 21B is an enlarged view of a shaped cam element from the drive mechanism of FIG. 21A.

Turning now to FIGS. 21A and 21B, this illustrates an alternative approach for implementation of the linkage in which the shuttle ejector 206 and the shuttle holder 204 are mounted on a common slide, main slider 735. In this case, the linkage preferably includes a first transmission defining a first timing profile for motion of the slide as a function of displacement of the user input and a second transmission defining a second timing profile for motion of the shuttle ejector and/or the shuttle holder as a function of displacement of the slide. The overall motion of the shuttle ejector is then the sum of the motion of the main slider and the differential motion of the shuttle ejector relative to the main slider. At least this differential motion, defined by the second timing profile, defines motion of the shuttle ejector and/or the shuttle holder as a function of displacement of the user input over two cycles of displacement of the shuttle transmitter from the withdrawn position to the penetrating position and back to the withdrawn position, wherein the motion over a first of the two cycles (e.g., a "PUT" process) is non-identical to the motion over a second of the two cycles (e.g., a "GET" process).

Preferably, each press (and release) of push button 731 activates either a PUT needle action or a GET needle action, followed by the device shaft and suture mechanism rotation to a new piercing point (e.g. 60 deg./step).

Pressing button 731 displaces gear rack 732 which, in turn, rotates gear wheel 733 by 180 deg. together with eccentric cam 734. Cam 734 may have a simple eccentric profile with eccentric amplitude per motion function $f_1$ per one push and release actions forcing linear motion of main slider 735 through engagement in an opening 743 in the main slider 735, acting as double side flat cam follower. Similar opening 744 in the secondary slider 737 is engaged with a piggyback secondary cam 736. A preferred exemplary form of cam 736 is shown enlarged in FIG. 21B.

Cam 736 has an axis connected to the main slider so as to move together with slider 735. A gear wheel 745 is axially interconnected with cam 736 so as to rotate together. A gear rack 742, also connected to button 731, has a position and length chosen to operate one-way bearings 738 only after cam 734 has rotated 180 deg. back and forth (completing a needle PUT or GET action). The one way bearing 738 rotates both device shaft 110 and the suturing mechanism needle transmitter tube 204 and rod 206.

The main slider 735 is connected to the tube 204 through a swivel joint 739 while the secondary slider 737 is connected to the ejector (rod) member 206 through a swivel joint 740. A spring 741 pushes back button 731 to its initial position.

Figures 22A, 22B:
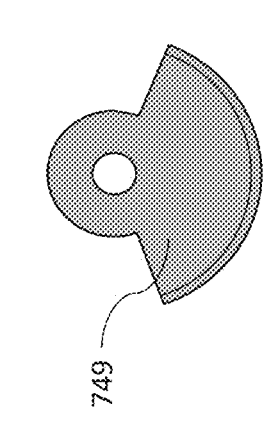
FIG. 22A is a schematic representation of a partial view of additional components of the mechanism of FIG. 21A.
FIG. 22B is an enlarged view of a sector gear element from FIG. 22A.

FIG. 22A illustrates the same structure as FIG. 21A but showing additional components according to one preferred implementation which lie in an additional layer of the mechanism not visible in FIG. 21A. Specifically, there is shown a slotted frame 750 having two gear racks 746, one on each side, axially centered relative to main slider 735 and aligned along the direction of motion. Slotted frame 750 is rigidly connected to the suturing drive mechanism enclosure (housing) 747. Each of the gear racks may have one, optionally slightly longer (protruding), tooth 748 on one rack end, arranged on opposite sides.

A sector gear wheel 749 is shaped to fully engage at any angular position to only one of the gear racks 746 and when the geared section of the wheel is perpendicular to both side gear rakes (FIG. 23A or 34B), its teeth ends will lie just outside the line defining the ends of the side gear teeth. In this position only the projecting end teeth 748 can mesh with the sector gear teeth.

The sector gear wheel 749 (FIG. 22B) is axially interconnected so as to rotate together with gear wheel 751, with their common axis of rotation being mounted to main slide 735. Gear wheel 751 typically meshes with gear wheel 745 with a gear ratio 2:1 (one rotation of wheel 751 will typically rotate wheel 745 by 180 deg.).

Figures 23A, 23B, 23C, 23D, 23E:
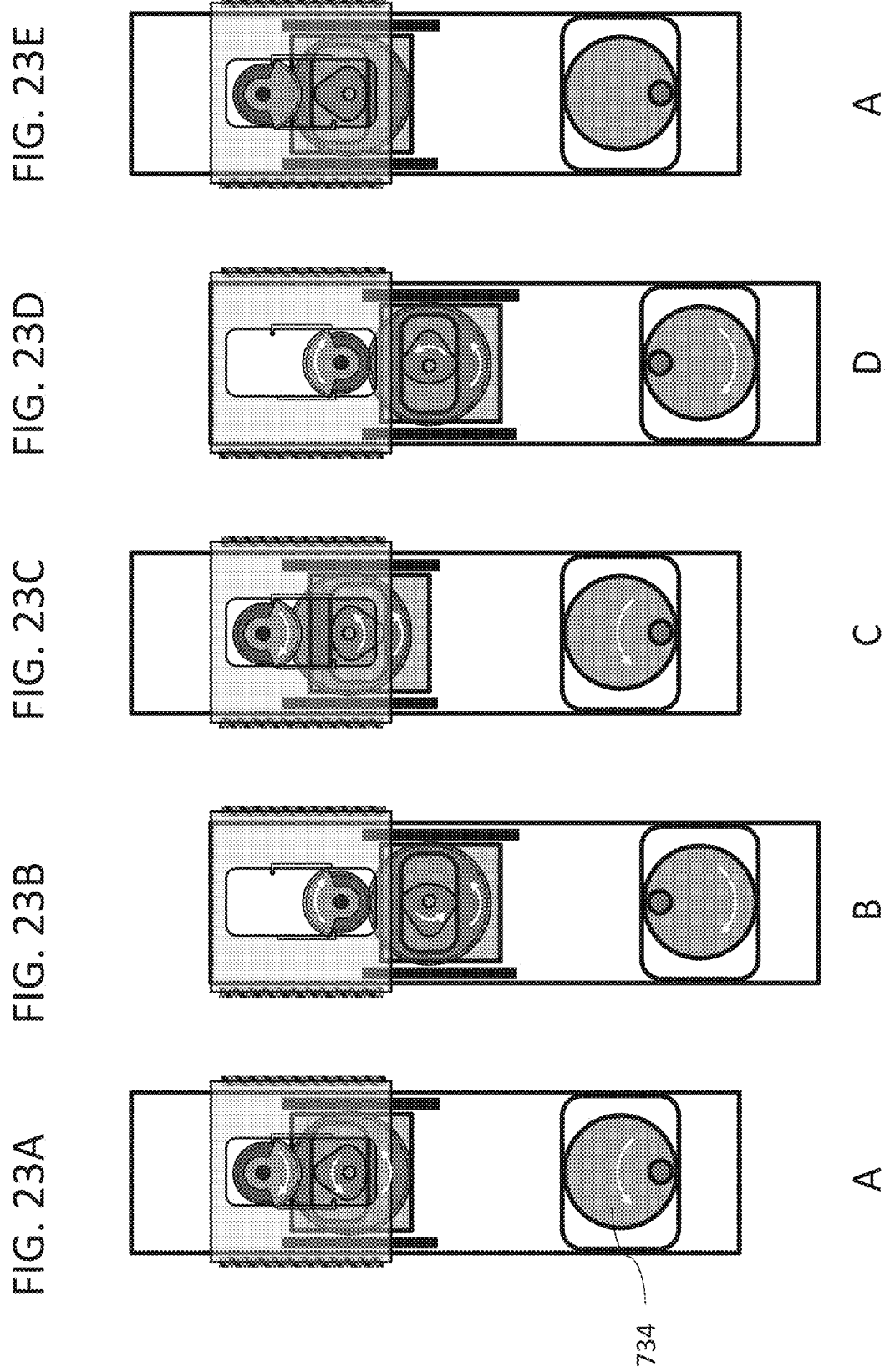
FIGS. 23A-23E are a sequence of states of a main slider from the mechanism of FIG. 21A showing a sequence of operation of the mechanism.

When the apex of cam 734 and cam apex 752 are aligned upwards with the motion line of main slider 735, the sector gear wheel 749 is typically positioned to be driven by the side gear racks 746, in the position of FIG. 23A.

The size of cam 734, sector gear wheel 749, gear wheels 751 and 745 may be tuned to rotate cam 736 from the position of FIG. 23A to the position of FIG. 23C or vice versa (back to FIG. 23A) during the rotation of cam 734 by 360 deg. (or two 180 deg. back and forth rotations).

The profile of cam 736 is typically a symmetrical combination of surfaces 755 (FIG. 21B) that correspond to the required differential motion of shuttle ejector 206 relative to the motion of shuttle holder 204, which itself corresponds to the motion of the main slider 735 as determined by cam 734. The overall sequence of motion of the drive mechanism is illustrated in FIGS. 23A-23E.

As before, in a variant implementation (not shown), displacement of the main cam 734 may be generated by two opposing buttons, similar to that described above with reference to FIG. 20.

Figures 24A, 24B:
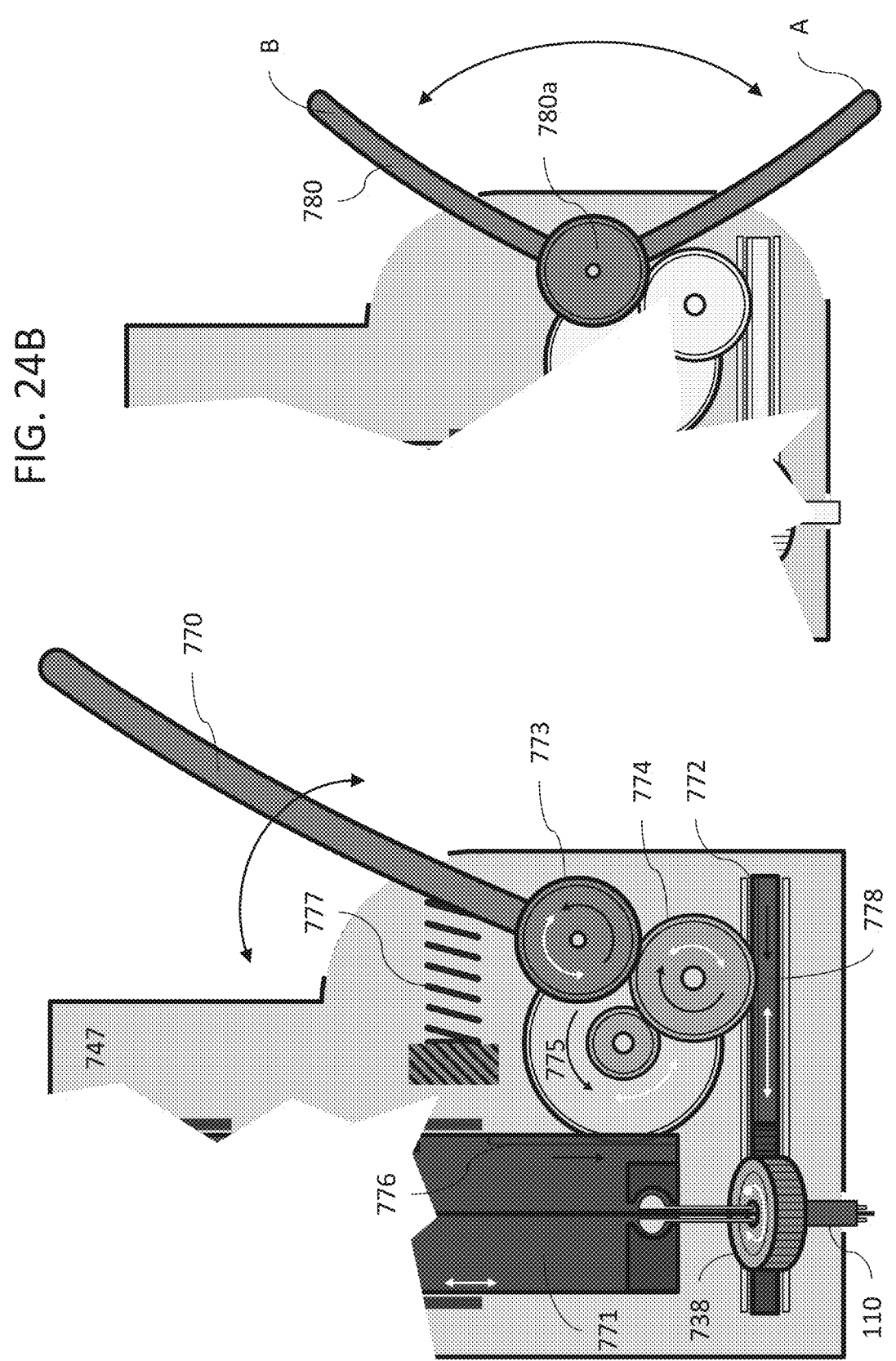
FIGS. 24A and 24B are schematic representations of further variants of the drive mechanism of FIG. 19A employing levers as a user input.

Turning now to FIG. 24A, it should be noted that the user input of the present invention may employ a linear motion, a rotary motion, or any other desired motion. By way of one further non-limiting example, FIG. 24A illustrates a drive mechanism in which a PUT needle action or a GET needle action is effected by operation of a lever input 770 acting against bias of a spring 777. The lever input may be connected to both main slider 771 and a gear rack 772 that is part of a member 778, via a gear train combining gear wheels such as gear wheel 773, 774 and double gear wheel 775. Main slider 771 may include a gear rack 776, preferably on its side, for engagement with the gear train. Member 778 may include a second gear rack 779 to rotate a geared, one-way bearing 738, connected to the device shaft 110, together with the suturing mechanism. Typically, the rotation action will be effected on the return of the lever and after the completion of a needle GET or PUT action.

Other aspects of the suturing control mechanism may be similar to those described above with reference to and of FIGS. 19A-23E.

FIG. 24B illustrates a further variant implementation of a user input employing a double-lever input 780. In this case, a PUT needle action and a GET needle action may each be effected by operation of the double lever 780, optionally without return springs.

A gear train connecting the double-lever input to the linkage may be adjusted to allow effecting a "full" GET or PUT needle operation followed by rotation of the device shaft and suturing mechanism to a new piercing point. For example, pressing on lever end A may effect a PUT needle action, and then pressing on lever end B will effect a GET needle action. The device may be supplied with the double lever button already pressed on one side, typically side B. The lever gear 780a may be meshed directly to the main slider presented in previous figures, such as FIG. 24A.

Location of Needle Receiver Actuator

A feature of the preferred examples of the suturing mechanism described herein, as well as a number of other suturing mechanisms otherwise known in the art, is the use of a selectively deployable shuttle receiver for receiving and/or holding the shuttle on the distal side of the material to be sutured at one or more stages of the suturing process. The shuttle receiver is preferably retractable to a retracted position relative to the elongated body and selectively deployable to a deployed position for receiving the shuttle. A further aspect of the present invention, not necessarily limited to the particular details of the suturing mechanism sequence or of the drive mechanism for the suturing process, relates to positioning of an actuator 781, linked to the shuttle receiver, for deploying the shuttle receiver from a retracted position to its deployed position. Specifically, according to an aspect of the present invention, the actuator 781 is associated with the handle 130 at a location distal to the user input for the suturing operations, such as is shown in FIG.

27
28

1. This distal positioning ensures that the mechanism does not obstruct user access to the suturing control mechanism during the subsequent suturing sequence.

Figure 25:
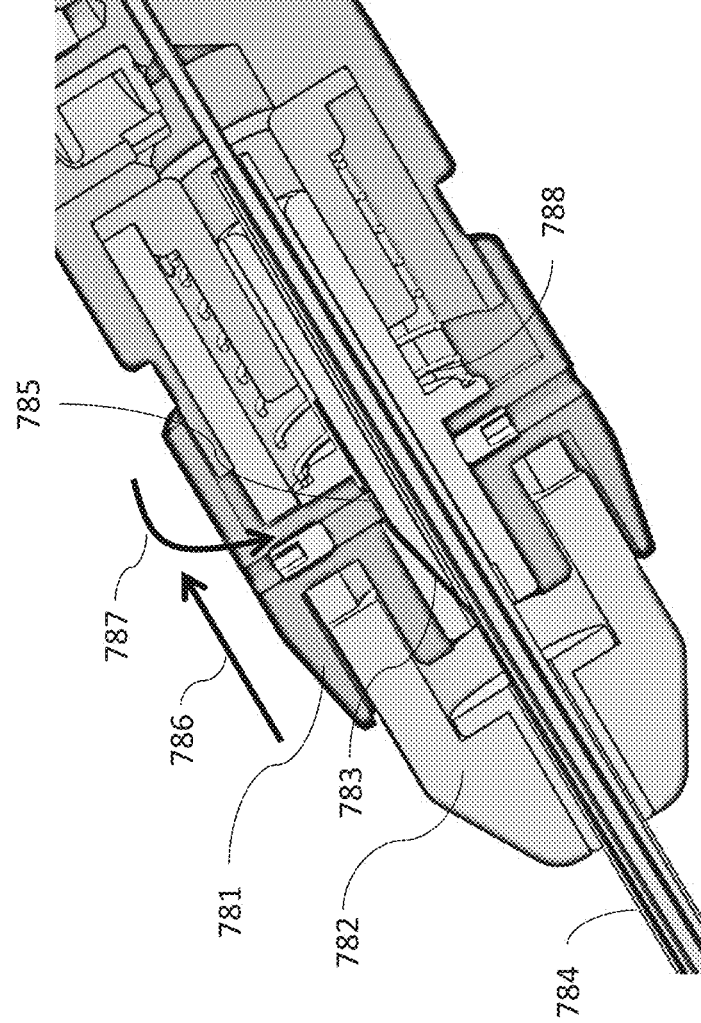
FIG. 25 is a partial axial cross-sectional view taken through a handle of the suturing system of FIG. 1 illustrating an actuator for selective deployment of a shuttle receiver according to a further aspect of the present invention.

A non-limiting example of an actuator for deploying the shuttle receiver is illustrated here in FIGS. 25 and 26A-26C. Specifically, FIG. 25 illustrates in axial cross-section the lower end of an HMI module (handle) showing components of a rotary mechanism and grip for deployment of the needle receiver.

As illustrated here, a rotary grip 781 at the lower end of an HMI handle 782 engages with an internal space used as a partly linear, partly rotary track or slot for the rotary grip. A connective member 783, preferably made of super elastic alloy such as Nitinol, preferably concealed inside the device shaft 784, is engaged at 785 with the rotary grip. To deploy the needle receiver the rotary grip is pulled proximally (arrow 786), and then the grip is rotated to be locked (arrow 787). The locking motion may be configured to be a clockwise or anticlockwise rotation.

To release the needle receiver at the end of a procedure, the rotary grip is unlocked by rotating it in the opposite direction of locking. Optionally, a spring 788 may then force the rotary grip to return to its initial position, releasing the tension and pushing distally the connective member 783. By releasing the tension on the connective member, the needle receiver is allowed to retract to its undeployed position.

Figures 27A, 27B, 27C:
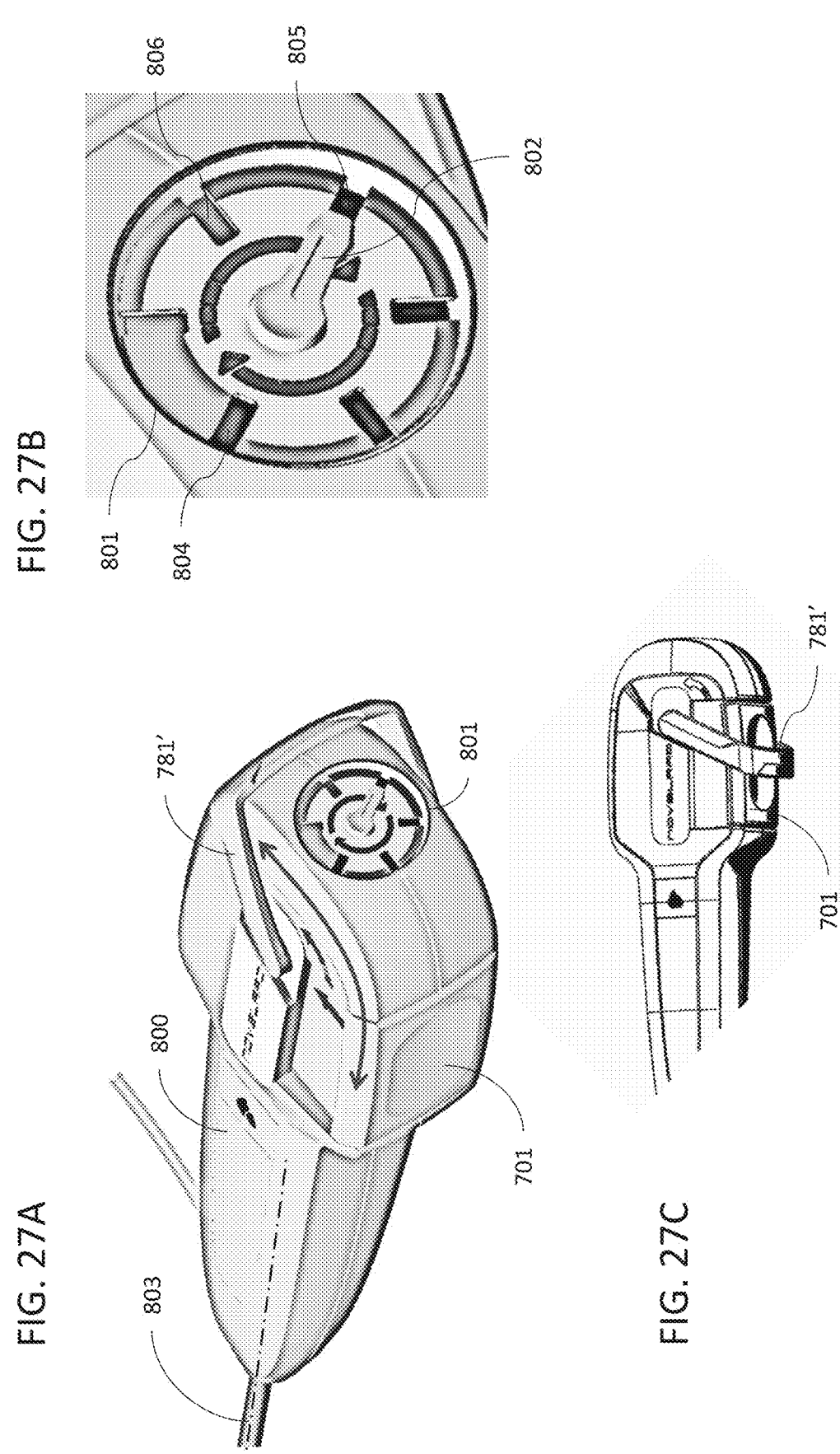
FIGS. 27A-27C are an isometric view, and enlarged view and a side view, respectively, of an HMI module according to a further aspect of the present invention, illustrating a progress indicator for showing a position and operating state of the suturing mechanism during a sequence of suture stitches.
Figures 28A, 28B, 28C, 28D:
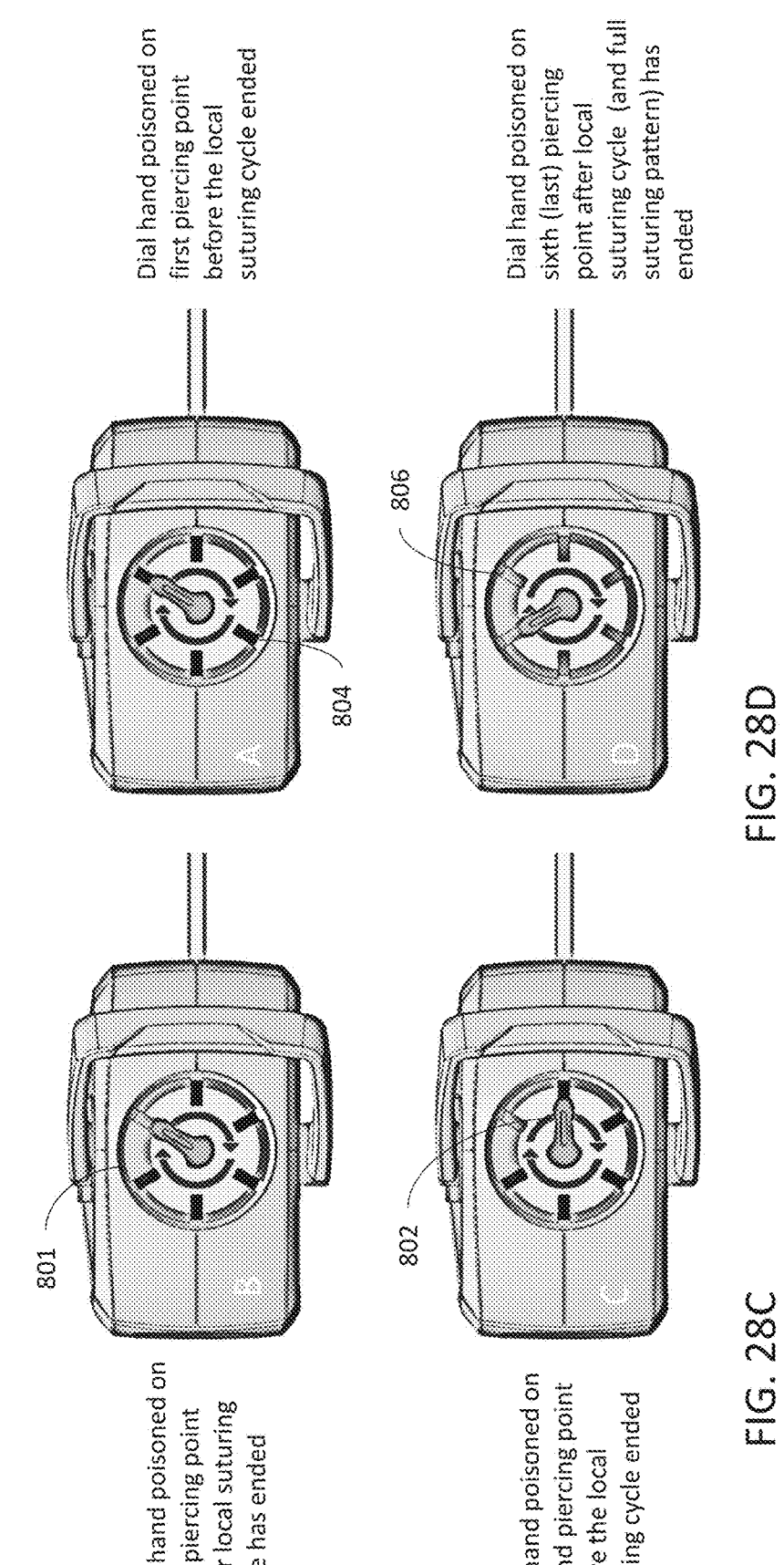
FIGS. 28A-28D are end views of the HMI module of FIG. 27A illustrating a sequence of states of the indicator.

Although the distal positioning of actuator 781 is believed to have particular advantages in certain implementations, it should be noted that additional considerations may in some cases lead to alternative preferred implementations of the actuator for the shuttle receiver. For example, in an alternative embodiment illustrated in FIG. 27A, deployment of the shuttle receiver is controlled by a lever 781' which is configured to mechanically obstruct operation of the suturing mechanism user input 701 when the shuttle receiver is in its retracted position (FIG. 27C). This prevents inadvertent reversal of the required order of operations when using the device.

Suturing Progress Indicator

A further aspect of the present invention, not necessarily limited to the particular details of the suturing mechanism described above, is provision of an indicator which provides a visual indication of a current position and/or status of a suturing device for performing a sequence of running stitches. A non-limiting example of an implementation of this feature is illustrated herein with reference to FIGS. 27A-29B.

Referring to FIG. 27A and 27B, wherever rotation of the suturing mechanism between stitches occurs relative to at least part of the HMI module (such as according to the options of FIGS. 12B, 12C and 12D), the non-rotating part of the HMI module may advantageously include an indicator, illustrated here as a suturing progress dial 801.

The dial 800 preferably includes a dial hand 802 showing the current angular location of piercing, which may be an angular position relative to a first initial piercing point about an axis of the device insertion 803.

Most preferably, the dial also provides a visual indication of suturing (piercing) progress at the current location. For example, all dial marks may have an initial color 804 which, after completion of a local suture (piercing) cycle at the "active mark" 805 (current position), changes its color to color B (as illustrated at 806). Thus, at the completion of the suturing procedure, all dial marks are changed to color B. FIGS. 28A-28D illustrate a number of stages during progress of a suturing procedure using a device designed to perform 6 successive stitches. At each stage, the operator can immediately see where the suturing device is currently deployed, and whether the suture stitch has yet been completed at that location.

The indicator may be mechanical, electromechanical or any combination thereof. The indicator may be located directly on the device or at a remote location with wired or wireless connection to the device. Dial marks or displayed information may be alphanumeric. Suture progress and status, such as a dial hand, and colors 804 or 806, may be displayed through the use of LEDs or LCDs. The indicator may advantageously include the display of further indicators such as blood pressure, suture thread progress during suturing, barcode, etc.

Embodiments of a mechanical dial may include direct or geared connection of the dial hand to the device shaft, such that rotation of the shaft will rotate the dial hand. The dial marks color may change by the end motion of the user input.

Figures 29A, 29B:
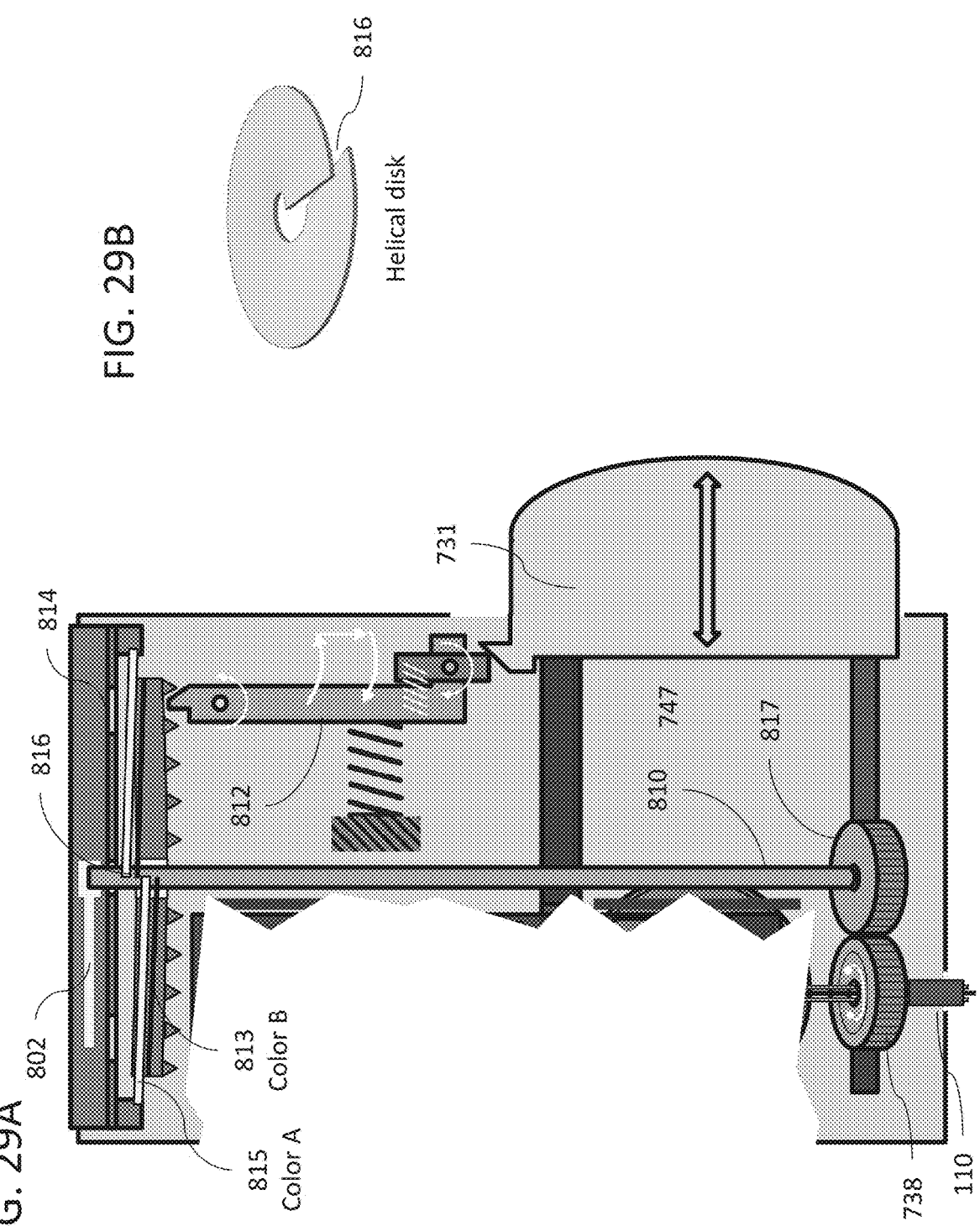
FIG. 29A is a partial schematic representation of a mechanism for actuating the indicator of FIG. 27A.
FIG. 29B is an isometric view of a helical split disk for use in the indicator of FIG. 29A.

FIGS. 29A and 29B illustrate schematically a possible implementation of a mechanism for providing a dial display with the properties described above. The device employs an indicator arm to show the current rotational state of the suturing mechanism, and a helical split disk to progressively switch the apparent color of the colored status-indicator at each position.

After pressing and releasing suturing button 731, one-way bearing 738 rotates both the device shaft 110 and the gear wheel 817, and thus also the dial shaft 810 and the dial hand 802 to the next piercing point and dial mark.

One-way rotational lever 812 is deployed to rotate a second color B helical disk 813 by one angular step per motion of button 731, thereby changing the apparent color of the current piercing point indicator from color A to color B. The disks colors may be visible through mark slots on the dial floor 814.

Both helical disks 813 and 815 have radial slots 816, allowing them to overlap one over the other during the rotation of disk 813.

Suture Feeder with Feedback

A further aspect of the present invention, not necessarily limited to the particular details of the suturing mechanism described above, provides audible and/or tactile feedback to indicate dispensing of suture thread from a dispenser. When operating a suturing system that is capable of performing a sequence of suture stitches, each successive stitch requires dispensing of an additional length of suture thread. By generating a series of "clicks" or other audible, tactile and/or visual feedback as the suture thread is dispensed, the operator is provided with intuitive feedback that the successive suture stitches (performed percutaneously and therefore not visible to the eye) are progressing successfully.

Figures 30A, 30B:
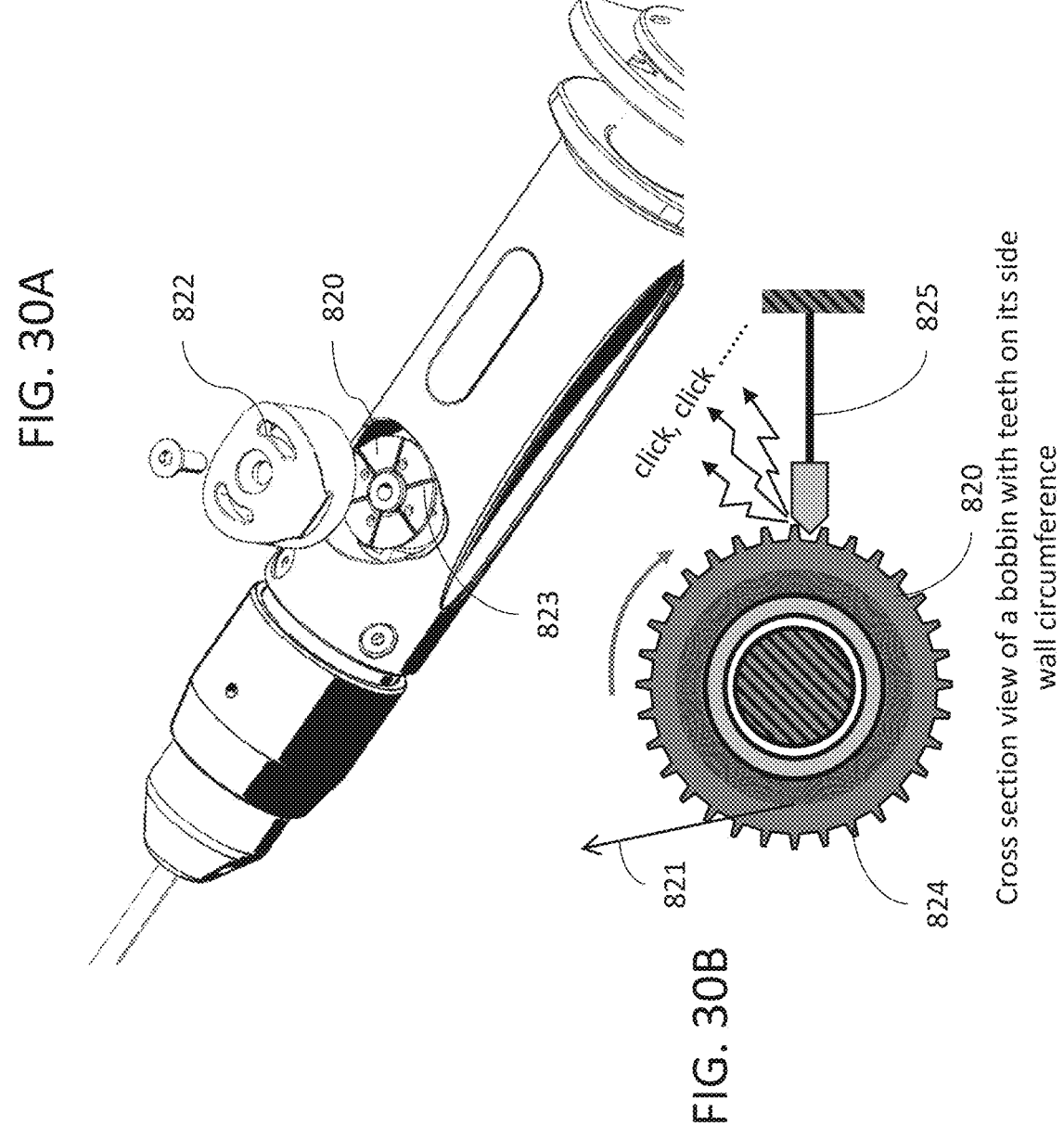
FIG. 30A is an exploded isometric view of an HMI module according to a further aspect of the present invention including a suture filament dispenser providing feedback during dispensing of suture filament.
FIG. 30B is a schematic plan view of a bobbin from the dispenser of FIG. 30A.

An example of a suture thread dispenser according to this aspect of the present invention is illustrated in FIGS. 30A and 30B. In this case, a bobbin 820 may be incorporated into the HMI module, optionally part of a disposable cassette. A supply of suture filament 821 is provided, wound around the bobbin.

The bobbin cover may include one or more openings 822, to view the rotation of the bobbin as filament is fed to the suture mechanism. The bobbin side walls may include marks 823. When the bobbin rotates, movement of the marks is visible through the openings 822, providing visual confirmation of the dispensing of the filament.

Additionally, or alternatively, one or more of the bobbin side walls is implemented with plurality of peripheral projections or recesses, optionally like teeth 824, on an external or lower side of the wall. The teeth preferably engage a flexible member 825. The flexible member may prevent unwanted free rotation of the bobbin when filament is not being fed to the suture mechanism. It preferably also generates a clicking sound and tactile vibration during rotation of the bobbin.

Bleeder Tube Management

A further aspect of the present invention, not necessarily limited to the particular details of the suturing mechanism described above, provides for management of a bleeder tube to accommodate relative rotation between the shaft and part of the HMI module, and to allow selective closure and reopening of the bleeder tube.

As mentioned earlier, a bleeder tube is advantageously provided extending from a bleeder inlet 132 along the elongated body to an outlet associated with the handle, to allow verification of correct positioning of the device within a blood vessel.

Figures 31A, 31B, 31C:
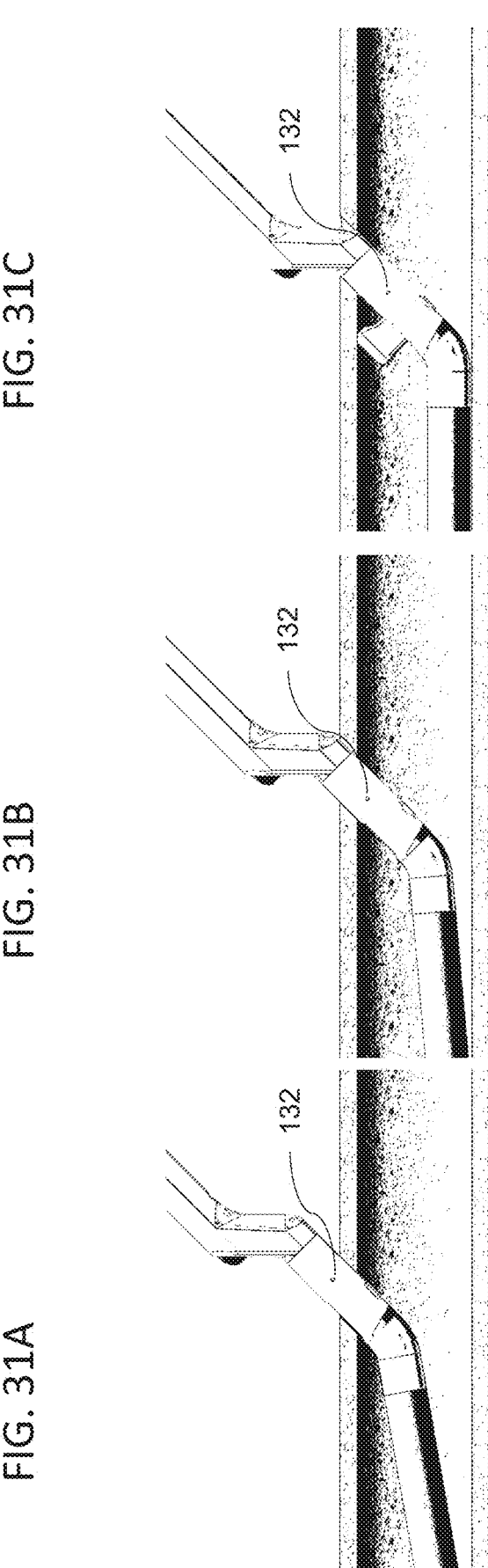
FIGS. 31A-31C are schematic views of various positioning of the suturing device of the present invention relative to a blood vessel indicating the function of a bleeder tube.

The principle of operation of the bleeder tube is illustrated in FIGS. 31A-31C. In FIG. 31A, the inlet access hole 132 is outside the blood vessel 131 and blood flow is not enabled. In FIG. 31B, the device is further inserted into the blood vessel, to a point where the access hole is exposed to blood flow 135, enabling the flow to reached the device HMI module through conduit in the device shaft 133. Correct positioning of the device is thus confirmed by drops of blood released from the bleeder tube outlet. In FIG. 31C, the suturing mechanism needle receiver 134 was deployed. Blood may still flow to the HMI module.

Figures 32A, 32B:
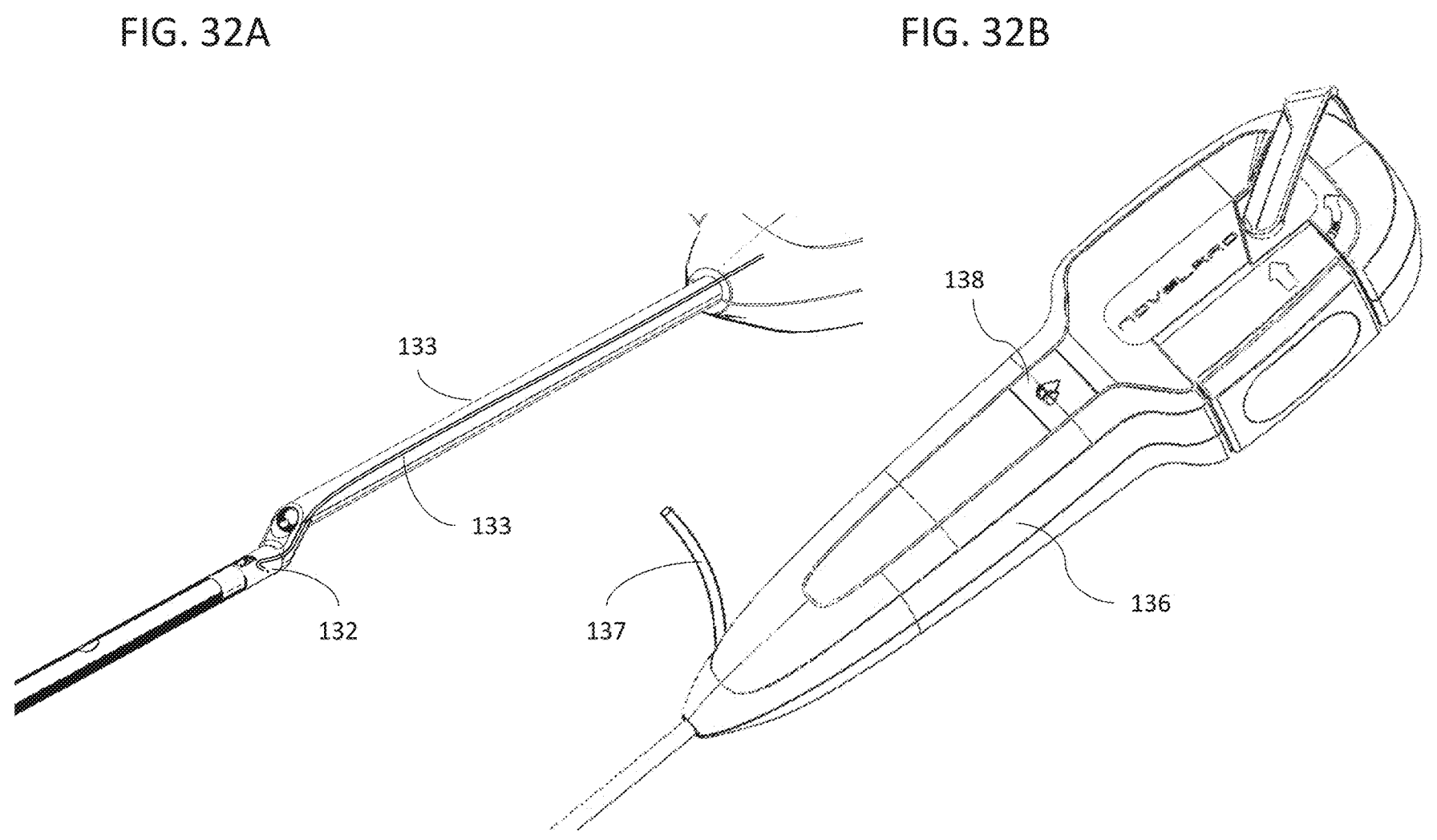

The bleeder tube may be implemented either externally to the device shaft (FIG. 32A) or internally (FIG. 32B). In either case, the bleeder conduit is most preferably implemented as a continuous tube without any connectors or junctions.

In the case of an elongated body that is rotatable about its longitudinal axis relative to the handle for performing stitches in successive angular positions about the elongated body, the connection of the bleeder tube preferably accommodates relative rotation of the shaft relative to the handle without kinking of the bleeder tube.

In order to avoid the complexity of any type of swivel-connector incorporated into the bleeder tube, an aspect of the present invention provides a particularly elegant and simple solution for accommodating this relative rotation. Specifically, for the range of rotation typically required for the suturing devices of the present invention (typically no more than 360 degrees), it has been found sufficient to provide an unsupported loop of tube located so as to accommodate relative rotation between the elongated body and the handle. Optionally, the unsupported loop may be provided with a braided or otherwise bend-resistant sleeve or other reinforcement to further inhibit kinking of the tube during rotation.

Figures 33A, 33B:
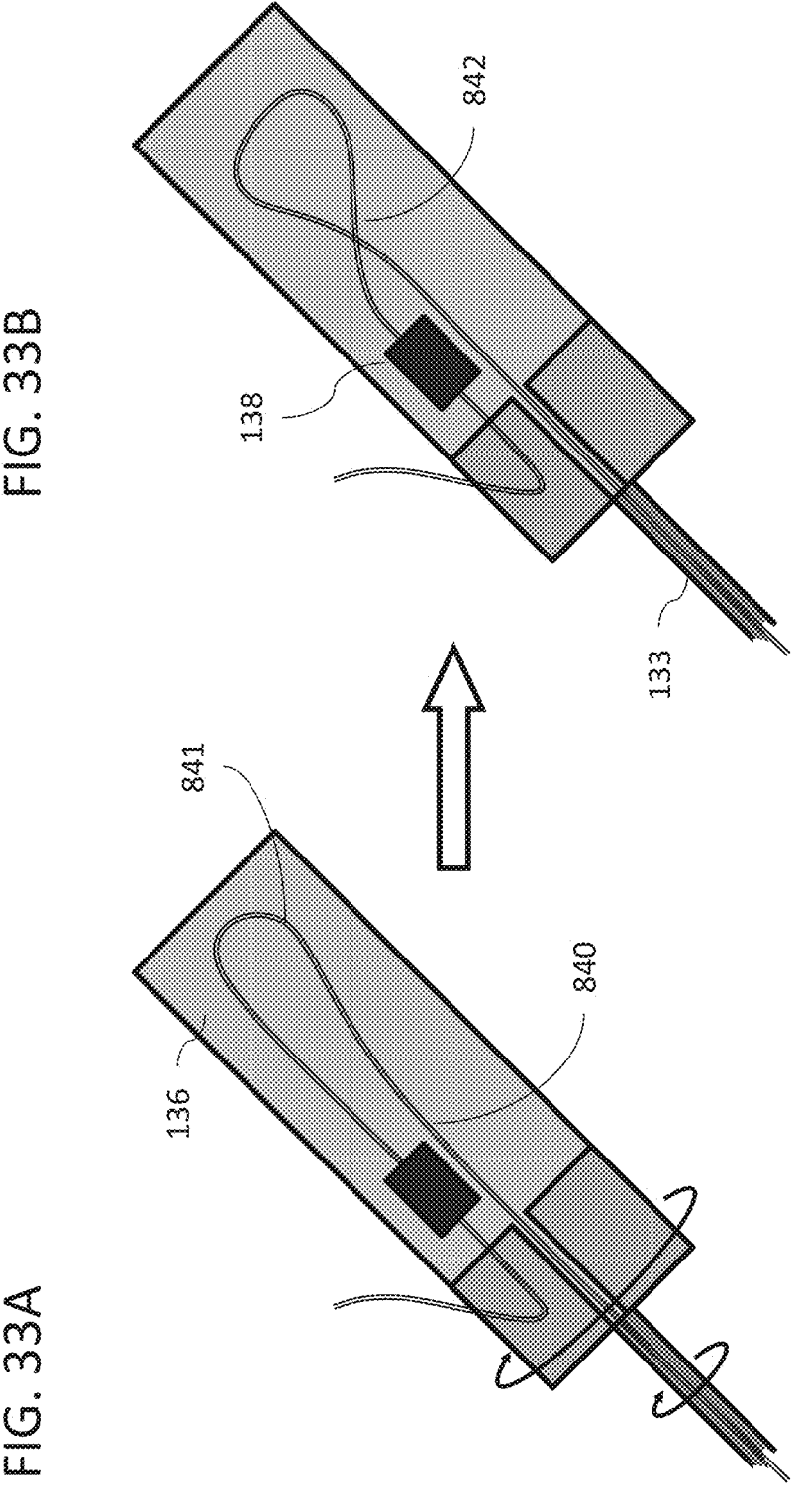
FIGS. 33A and 33B illustrate schematically a form of connection of a bleeder tube for kink-free accommodating of relative rotation between the shaft and the HMI module according to a further aspect of the present invention.

This aspect of the invention is illustrated in FIGS. 33A and 33B, where bleeder conduit 840, preferably a flexible micro tube, optionally made of flexible material such as silicone may be routed inside the HMI module 136 in order allow the device shaft 133 and suture mechanism to rotate at least 360 deg. relative to the HMI module without kinking. Tube routing preferably includes a loop 841 of the tube to provide rotational flexibility 842.

Figure 34:
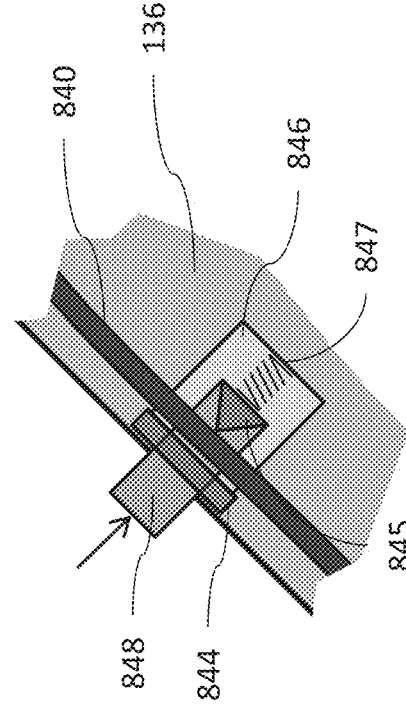
FIG. 34 is a schematic representation of a pinch valve configuration for selectively blocking the bleed tube of the suturing device according to a further aspect of the present invention.

Additionally, or alternatively, a pinch valve is preferably associated with the handle and deployed to selectively obstruct the bleeder tube. This option is illustrated in FIG. 34 where a normally close pinch valve is shown. Alternatively, the valve may be implemented as a toggle valve where the device is preferably delivered with the valve set to OPEN— allowing flow. Alternatively, an electromechanical valve may be used.

In the example illustrated here, a pinch valve is encapsulated inside the HMI module 136. The flexible blood conduit 840 passes through the valve body 843. The tube is pinched between a valve anvil 844 and a pinching element 845, optionally part of a valve spool 846. The spool is acted upon by a flexible element 847, typically a spring, to pinch the tube, stopping flow, as long as the protruding end of the spool 848 is not pressed.

Pinching Member with Sensor

As already described above with reference to FIGS. 10A-10C, certain particularly preferred implementations of the suturing device of the present invention employ a preload member (or pinching member or depresser) 1102 to press against the tissue prior to penetration, thereby stabilizing the tissue. According to a further feature of certain particularly preferred implementations of the present invention, at least one sensor is associated with the depresser and generating an output that is indicative of a thickness of the material between the depresser and the shuttle receiver, and/or in some cases provides other important information regarding the properties of the tissue encountered by the depresser.

Figures 35A, 35B, 35C:
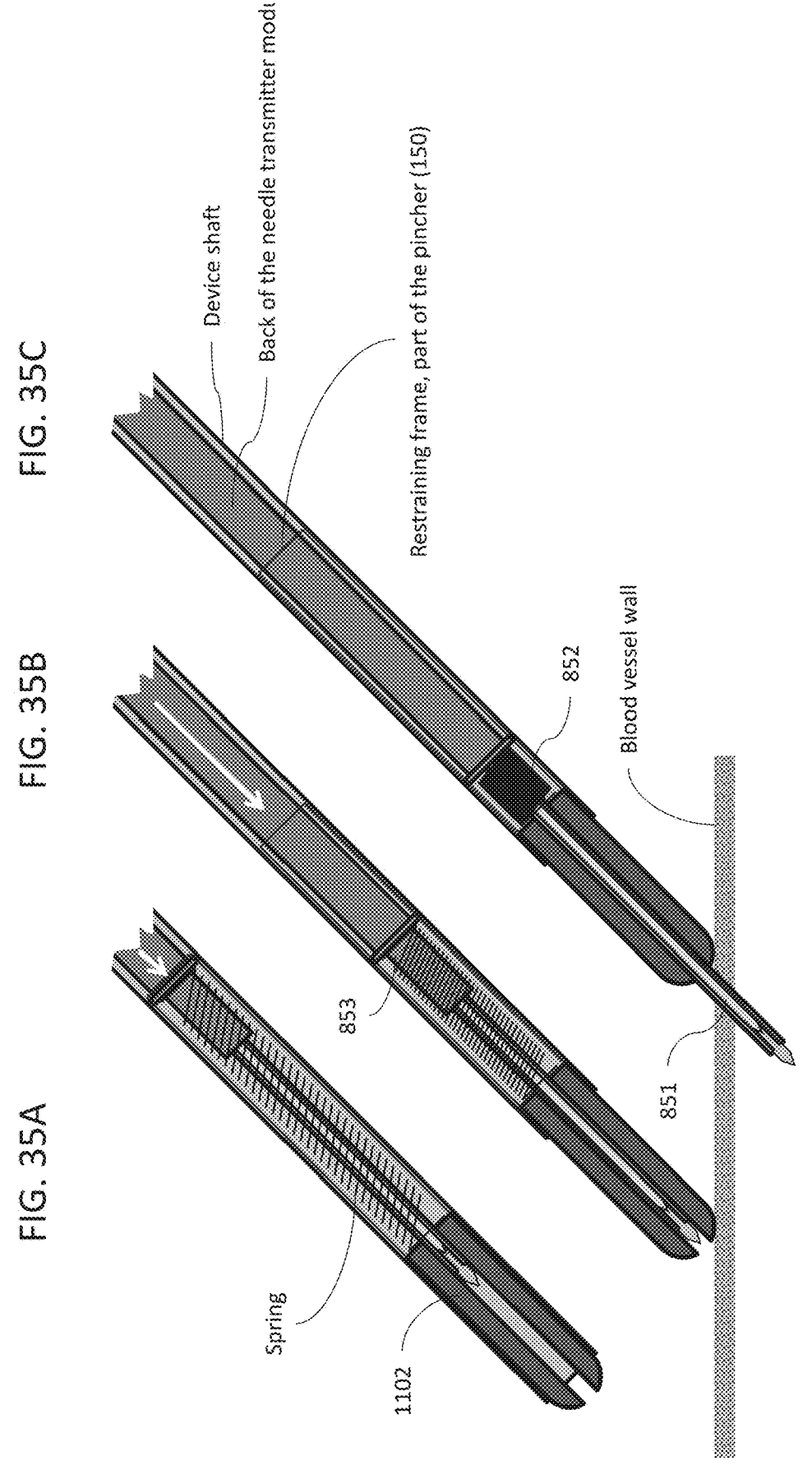
FIGS. 35A-35C are schematic cross-sectional views illustrating a series of states of a preload member for bearing on a region of tissue to be pierced.

FIGS. 35A-35C are cross-sectional views of the needle transmitter including the preload member corresponding to the positions of FIGS. 10A-10C, respectively.

At full stock, force on the pincher 1102 may be implemented directly through a squeezed spring 852 or by a "step" 853 in the needle transmitter shaft.

Figures 36A, 36B:
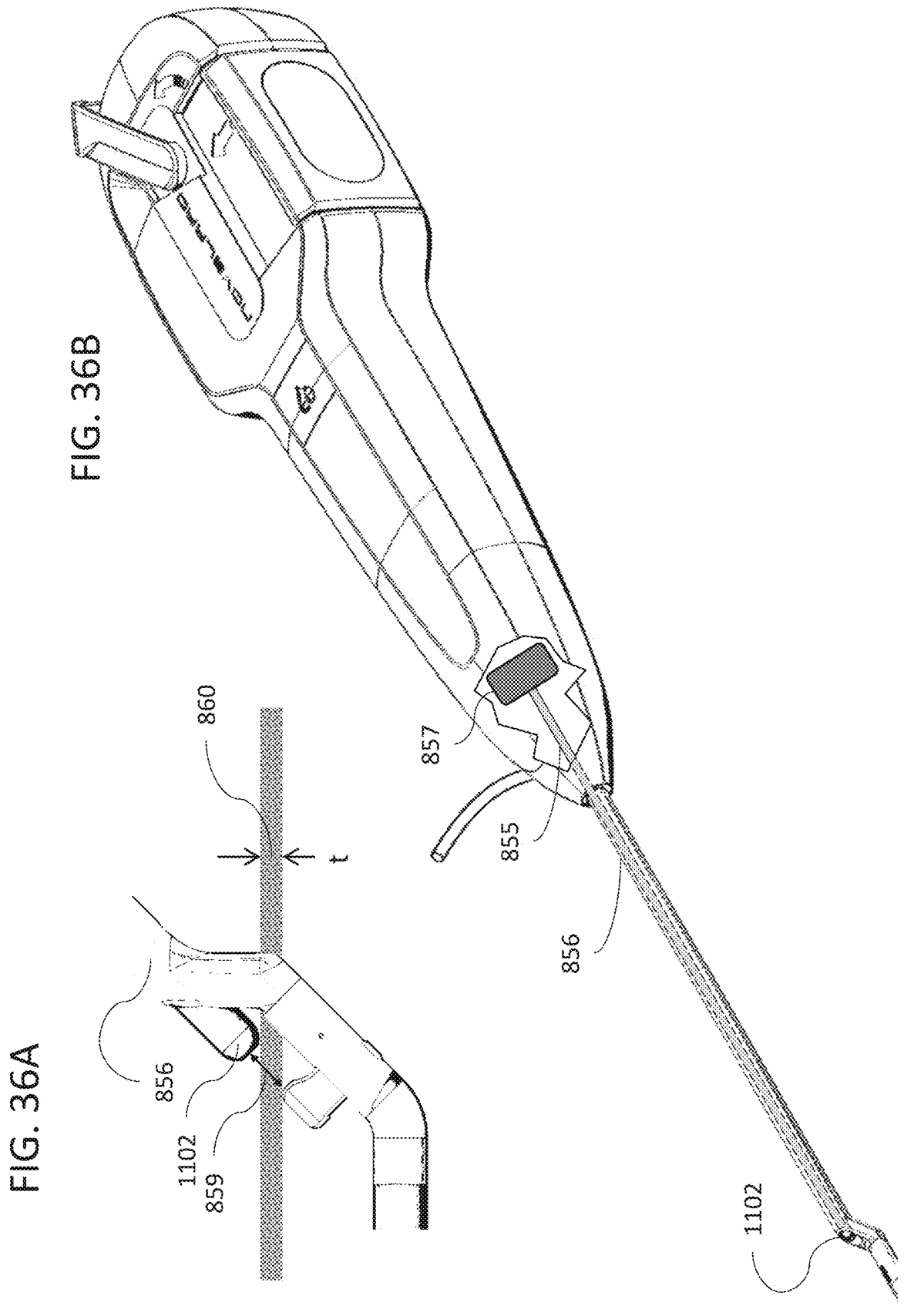
FIG. 36A is a schematic side view illustrating measurement of a vessel wall thickness by use of the preload member.
FIG. 36B is a schematic isometric view illustrating a possible deployment of a sensor associated with the preload member.

According to an implementation illustrated in FIGS. 36A and 36B, the pinch member 1102 may be directly incorporated with an optionally tubular element 855, extending along the device shaft 856 to a sensor 857, preferably in the HMI module 858.

The sensor, which may be mechanical or electromechanical, may obtain a measurement, such as 859, from which the blood vessel wall thickness 860 can be derived, and may advantageously also provide additional information, such as an indication of vessel wall stiffness derived during the pinching motion.

Tactile Feedback Using Magnetic Elements

A further aspect of the present invention, not necessarily limited to the particular details of the suturing mechanism described above, employs magnetic elements to provide tactile and/or audible feedback. Thus, in one implementation, a user input 876 includes a first part of a magnetic snap and wherein the handle includes a second part of the magnetic snap. The first and second parts of the magnetic snap are deployed such that, when the user input reaches a fully-displaced position, the first and second parts of the magnetic snap close together abruptly to generate tactile and/or audible feedback. This feature may be implemented with any of the buttons and/or levers of an HMI module for any suturing system.

Figures 37A, 37B, 37C:
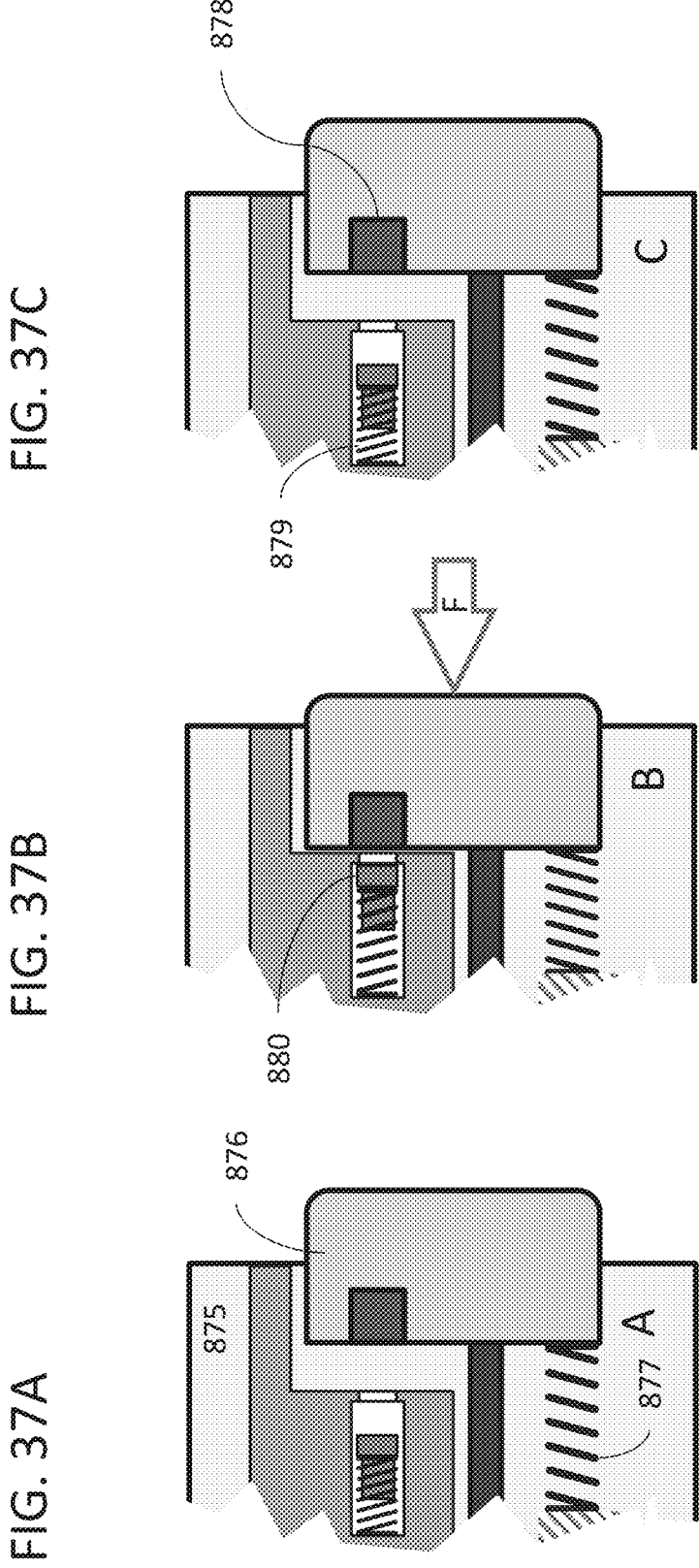
FIGS. 37A-37C are schematic cross-sectional views illustrating operation of a magnet-based arrangement for providing tactile and/or audible feedback for the movement of user inputs according to a further aspect of the present invention.

Referring now to FIGS. 37A-37C, these illustrate an HMI module 875 having a button 876 preloaded outwards by spring 877, and a tactile feedback module comprising a magnet 878 incorporated in the button, a spring 879 and a shuttling member 880 firmly connected to the spring, or other flexible member. Shuttling member 880 is a complementary part of a "magnetic snap" to operate with magnet 878, and may itself be a magnet, or more preferably, is made of ferritic material or alloy. Both members 879 and 880 may move in a limited, predefined manner, in this case axially, in the direction of magnet 878 in the button.

As illustrated in FIG. 37B, when button 876 is pushed inward, the ferritic member 880 is pulled by the magnetic force effected by magnet 876, resulting in spring 879 being stretched. The magnetic force applied by magnet 876 on the ferritic member 880 is non linear relative to the distance between them. As a result, ferritic member 880 accelerates as it moves towards magnet 876 until its motion is stopped by its surrounding. The stop of the accelerated motion results in noise and vibration.

As shown in FIG. 37C, when button 876 is released, the larger push force created by spring 877 will return the button, and this will release the ferritic member 880. Spring 879 then pulls it backwards to its initial position. The strength of spring 879 and ferritic member 880 may optionally be chosen to also create vibration and noise during the backward motion of the ferritic member.

The described structure may also be used as a toggle mechanism. If the magnet forces are strong enough to overcome spring 877 forces, the button will be locked in its depressed position until another element, such as an internal member or an opposite button, will positively push it back outwards.

Although illustrated above in the context of a vascular closure device, it should be noted that the suturing mechanism of the present invention may readily be implemented in other contexts and for other procedures, including but not limited to: closure of incisions, wounds or defects in a single material; modification of a shape or other properties of a single material; attachment of two or more materials arranged in overlapping relation by suturing through both layers; bringing together of two edges of two regions of material which may be of the same type or bodies of different materials; and anchoring of a suture in a material by forming stitches in overlapping relation by repeated closely-adjacent passes through the material. The material in question for any and all of the above may be a natural biological tissue or any other material. The device and method may also perform suturing to interconnect a prosthetic device or material with natural tissue.

One additional set of procedures suitable for implementation using the suturing devices of the present invention are coronary procedures including, but not limited to, (PFO) Patent foramen ovale, (ASD) Atrial septal defect and other sorts of structural heart disease.

The disclosed subject matter is also applicable to a range of cardiovascular procedures including but not limited to, Left atrial appendage occlusion (LAAO), Left atrial appendage closure (LAAC), (AAA or EVAR) Aneurysm repairs and more generally in transcatheter valve repairs, and as a minimally invasive heart apex closure or a minimally invasive repair of left ventricular.

The disclosed subject matter is also applicable to a wide range of minimally invasive procedures including, but not limited to, suturing operations during endoscopic procedures, laparoscopic procedures, gastroscopic procedures, otoscopic procedures and minimally invasive gynecologic procedures.

It will be appreciated that the above descriptions are intended only to serve as examples, and that many other embodiments are possible within the scope of the present invention as defined in the appended claims.

What is claimed is:

1. A suturing device comprising:
a suturing mechanism comprising:
   a shuttle for holding a suture, and
   a shuttle transmitter for controlling motion of said shuttle, said shuttle transmitter being displaceable along a longitudinal axis between a withdrawn position and a penetrating position, said shuttle transmitter being reconfigurable between a shuttle holding state configured to retain said shuttle in an engaged position engaged with said shuttle transmitter and a shuttle releasing state configured to release said shuttle from said engaged position; and
a drive mechanism for operating said suturing mechanism, said drive mechanism comprising:
  (a) a user input displaceable through a range of motion between a position A and a position B; and
  (b) a linkage mechanically associated with said user input and with said shuttle transmitter, said linkage configured to be actuated solely by displacements of said user input such that, when actuated by one or more unidirectional or bidirectionally displacements of said user input through said range of motion between positions A and B, said linkage generates a sequence of operations of said shuttle transmitter, said sequence of operations comprising:
    (i) displacement of said shuttle transmitter while engaged with said shuttle along said longitudinal axis from said withdrawn position to said penetrating position so as to penetrate the material at a first location;
    (ii) reconfiguration of said shuttle transmitter from said shuttle holding state to said shuttle releasing state; and
    (iii) displacement of said shuttle transmitter in said shuttle releasing state along said longitudinal axis from said penetrating position to said withdrawn position so as to withdraw from the material leaving a first suture stitch at the first location;
  said linkage further configured to be actuated solely by said user input such that, after repositioning of said shuttle transmitter and said shuttle aligned at a second location, when actuated by one or more unidirectional or bidirectional displacements of said user input through said range of motion between positions A and B, said linkage generates a further sequence of operations of said shuttle transmitter, said further sequence of operations comprising:
    (iv) displacement of said shuttle transmitter in said shuttle releasing state along said longitudinal axis from said withdrawn position to said penetrating position so as to penetrate the material at the second location;
    (v) reconfiguration of said shuttle transmitter from said shuttle releasing state to said shuttle holding state so as to hold said shuttle; and
    (vi) displacement of said shuttle transmitter along said longitudinal axis from said penetrating position to said withdrawn position so as to withdraw said shuttle from said material forming a second suture stitch at the second location,
wherein said reconfiguration of said shuttle transmitter from said shuttle holding state to said shuttle releasing state generates a tissue penetrating configuration of said shuttle transmitter without said shuttle, and wherein said reconfiguration of said shuttle transmitter from said shuttle releasing state to said shuttle holding state generates a tissue penetrating configuration of said shuttle transmitter together with said shuttle,
and wherein said shuttle transmitter comprises a shuttle holder and a shuttle ejector, and wherein reconfiguration of said shuttle transmitter between said shuttle holding state and said shuttle releasing state is effected by motion of said shuttle ejector relative to said shuttle holder along said longitudinal axis.

2. The suturing device of claim 1, wherein said repositioning of said shuttle transmitter is also performed by said linkage driven by displacements of said user input unidirectionally or bidirectionally.

3. The suturing device of claim 1, wherein said linkage is configured to convert further displacements of said user input unidirectionally or bidirectionally into repetition of said sequence of operations of said shuttle transmitter when aligned with a third and a fourth location so as to form a running stitch suture in the material.

4. The suturing device of claim 1, wherein said user input is manually displaceable in a first direction, and is spring-biased to return in a reverse direction when released.

5. The suturing device of claim 1, wherein said linkage includes a first transmission defining a first timing profile for motion of said shuttle holder as a function of displacement of said user input and a second transmission defining a second timing profile for motion of said shuttle ejector as a function of displacement of said user input.

6. The suturing device of claim 5, wherein said second timing profile defines motion of said shuttle ejector as a function of displacement of said user input over two cycles of displacement of said shuttle transmitter from said withdrawn position to said penetrating position and back to said withdrawn position, wherein the motion over a first of said two cycles is non-identical to the motion over a second of said two cycles.

7. The suturing device of claim 1, wherein said shuttle ejector and said shuttle holder are mounted on a common slide, and wherein said linkage includes a first transmission defining a first timing profile for motion of said slide as a function of displacement of said user input and a second transmission defining a second timing profile for motion of said shuttle ejector and/or said shuttle holder as a function of displacement of said slide.

8. The suturing device of claim 7, wherein said second timing profile defines motion of said shuttle ejector and/or said shuttle holder as a function of displacement of said user input over two cycles of displacement of said shuttle transmitter from said withdrawn position to said penetrating position and back to said withdrawn position, wherein the motion over a first of said two cycles is non- identical to the motion over a second of said two cycles.

9. The suturing device of claim 1, wherein the suturing device is a minimally-invasive suturing device including an elongated body for percutaneous insertion, and wherein said user input and said linkage are implemented as part of a handle associated with a proximal end of said elongated body.

10. The suturing device of claim 9, wherein the suturing device further comprises a shuttle receiver for receiving said shuttle on the second side of the material, said shuttle receiver being retractable to a retracted position relative to said elongated body and selectively deployable to a deployed position for receiving said shuttle, said drive mechanism further comprising a manually-operated actuator linked to said shuttle receiver for deploying said shuttle receiver from said retracted position to said deployed position, said actuator being associated with said handle at a location distal to said user input.

11. The suturing device of claim 9, wherein said elongated body is rotatable about its longitudinal axis relative to said handle for performing stitches in successive angular positions about said elongated body, and wherein said handle further comprises a mechanical indicator linked to said elongated body and configured to provide a visual indication of a current rotational position of said elongated body relative to said handle.

12. The suturing device of claim 11, wherein said mechanical indicator is additionally associated with said linkage and configured to provide a visual indication when the passing of said suture through the material has been completed at the current rotational position.

13. The suturing device of claim 9, further comprising a suture feeder associated with said handle for feeding suture along said elongated body to said shuttle, wherein said suture feeder is configured to provide tactile and/or audible feedback to a user as said suture is dispensed.

14. The suturing device of claim 9, further comprising:
(a) a shuttle receiver for receiving said shuttle on the second side of the material;
(b) a depresser associated with said shuttle transmitter, said depresser at least partially encompassing said shuttle transmitter and deployable to press the material between said depresser and said shuttle receiver; and
(c) at least one sensor associated with said depresser and generating an output indicative of a thickness of the material between said depresser and said shuttle receiver.

15. The suturing device of claim 1, wherein said suturing mechanism further comprises a distal pocket aligned with said longitudinal axis for releasably receiving said shuttle, said distal pocket being passive during said sequence of operations.

16. A suturing device comprising:
a suturing mechanism comprising:
a shuttle for holding a suture, and
a shuttle transmitter for controlling motion of said shuttle, said shuttle transmitter being displaceable along a longitudinal axis between a withdrawn position and a penetrating position, said shuttle transmitter being reconfigurable between a shuttle holding state and a shuttle releasing state; and
a drive mechanism for operating said suturing mechanism, said drive mechanism comprising:
(a) a user input displaceable through a range of motion; and
(b) a linkage mechanically associated with said user input and with said shuttle transmitter, said linkage configured to convert displacements of said user input unidirectionally or bidirectionally into a sequence of operations of said shuttle transmitter including:
(i) axial displacement of said shuttle transmitter from said withdrawn position to said penetrating position so as to penetrate the material at a first location;
(ii) reconfiguration of said shuttle transmitter from said shuttle holding state to said shuttle releasing state; and
(iii) axial displacement of said shuttle transmitter from said penetrating position to said withdrawn position so as to withdraw from the material leaving a first suture stitch at the first location;
and, after repositioning of said shuttle transmitter and said shuttle aligned at a second location:
(iv) axial displacement of said shuttle transmitter from said withdrawn position to said penetrating position so as to penetrate the material at the second location;

(v) reconfiguration of said shuttle transmitter from said shuttle releasing state to said shuttle holding state so as to hold said shuttle; and (vi) axial displacement of said shuttle transmitter from said penetrating position to said withdrawn position so as to withdraw said shuttle from the material forming a second suture stitch at the second location, wherein said reconfiguration of said shuttle transmitter from said shuttle holding state to said shuttle releasing state generates a tissue penetrating configuration of said shuttle transmitter without said shuttle, and wherein said reconfiguration of said shuttle transmitter from said shuttle releasing state to said shuttle holding state generates a tissue penetrating configuration of said shuttle transmitter together with said shuttle, and wherein said elongated body is rotatable about its longitudinal axis relative to said handle for performing stitches in successive angular positions about said elongated body, further comprising a bleeder tube extending from a bleeder inlet along said elongated body to an outlet associated with said handle, wherein said bleeder tube includes an unsupported loop of tube located to accommodate relative rotation between said elongated body and said handle.

17. The suturing device of claim 16, further comprising a pinch valve associated with said handle and deployed to selectively obstruct said bleeder tube.

18. A suturing device comprising:

a suturing mechanism comprising:

a shuttle for holding a suture, and a shuttle transmitter for controlling motion of said shuttle, said shuttle transmitter being displaceable along a longitudinal axis between a withdrawn position and a penetrating position, said shuttle transmitter being reconfigurable between a shuttle holding state and a shuttle releasing state; and a drive mechanism for operating said suturing mechanism, said drive mechanism comprising:

(a) a user input displaceable through a range of motion; and (b) a linkage mechanically associated with said user input and with said shuttle transmitter, said linkage configured to convert displacements of said user input unidirectionally or bidirectionally into a sequence of operations of said shuttle transmitter including:

(i) axial displacement of said shuttle transmitter from said withdrawn position to said penetrating position so as to penetrate the material at a first location;

(ii) reconfiguration of said shuttle transmitter from said shuttle holding state to said shuttle releasing state; and (iii) axial displacement of said shuttle transmitter from said penetrating position to said withdrawn position so as to withdraw from the material leaving a first suture stitch at the first location;

and, after repositioning of said shuttle transmitter and said shuttle aligned at a second location:

(iv) axial displacement of said shuttle transmitter from said withdrawn position to said penetrating position so as to penetrate the material at the second location;

(v) reconfiguration of said shuttle transmitter from said shuttle releasing state to said shuttle holding state so as to hold said shuttle; and (vi) axial displacement of said shuttle transmitter from said penetrating position to said withdrawn position so as to withdraw said shuttle from the material forming a second suture stitch at the second location, wherein said reconfiguration of said shuttle transmitter from said shuttle holding state to said shuttle releasing state generates a tissue penetrating configuration of said shuttle transmitter without said shuttle, and wherein said reconfiguration of said shuttle transmitter from said shuttle releasing state to said shuttle holding state generates a tissue penetrating configuration of said shuttle transmitter together with said shuttle, and wherein said user input includes a first part of a magnetic snap and wherein said handle includes a second part of said magnetic snap, said first and second parts of said magnetic snap being deployed such that, when said user input reaches a fully-displaced position, said first and second parts of said magnetic snap close together abruptly to generate tactile and/or audible feedback.

19. The suturing device of claim 18, wherein said user input is resiliently biased to return from said fully-displaced position to an initial position, and wherein said magnetic snap has a retention force which is insufficient to retain said user input in said fully-displaced position against said resilient bias.

20. The suturing device of claim 18, wherein said magnetic snap has a retention force sufficient to retain said user input in said fully-displaced position until positively displaced by the user back towards said initial position.

* * * * *